(12) United States Patent
Hu et al.

(10) Patent No.: US 12,421,286 B2
(45) Date of Patent: Sep. 23, 2025

(54) IL-2 MUTANT AND APPLICATION THEREOF

(71) Applicant: SHANDONG SIMCERE BIOPHARMACEUTICAL CO., LTD., Shandong (CN)

(72) Inventors: Yingying Hu, Shanghai (CN); Zhuoxiao Cao, Shanghai (CN); Renhong Tang, Jiangsu (CN); Hu Ge, Shanghai (CN); Yayuan Fu, Shanghai (CN); Jinsheng Ren, Jiangsu (CN)

(73) Assignee: SHANDONG SIMCERE BIOPHARMACEUTICAL CO., LTD., Shandong (CN)

( * ) Notice: Subject to any disclaimer, the term of this patent is extended or adjusted under 35 U.S.C. 154(b) by 0 days.

(21) Appl. No.: 18/024,151

(22) PCT Filed: Sep. 3, 2021

(86) PCT No.: PCT/CN2021/116463
§ 371 (c)(1),
(2) Date: Mar. 1, 2023

(87) PCT Pub. No.: WO2022/048640
PCT Pub. Date: Mar. 10, 2022

(65) Prior Publication Data
US 2023/0265148 A1 Aug. 24, 2023

(30) Foreign Application Priority Data

Sep. 4, 2020 (CN) .......................... 202010918842.0
Aug. 13, 2021 (CN) .......................... 202110932286.7

(51) Int. Cl.
*C07K 14/55* (2006.01)
*A61P 37/02* (2006.01)
*C12N 15/63* (2006.01)

(52) U.S. Cl.
CPC .............. *C07K 14/55* (2013.01); *A61P 37/02* (2018.01); *C12N 15/63* (2013.01); *C07K 2319/31* (2013.01)

(58) Field of Classification Search
CPC .................................................. A61K 38/2013
See application file for complete search history.

(56) References Cited

U.S. PATENT DOCUMENTS

| | | |
|---|---|---|
| 2005/0142106 A1 | 6/2005 | Wittrup et al. |
| 2018/0125941 A1 | 5/2018 | Greve |

FOREIGN PATENT DOCUMENTS

| | | |
|---|---|---|
| CN | 1442427 A | 9/2003 |
| CN | 102665754 A | 9/2012 |
| CN | 104231068 A | 12/2014 |
| CN | 110642934 A | 1/2020 |
| TW | I687435 B | 3/2020 |
| WO | 2014023679 A1 | 2/2014 |
| WO | 2019028425 A1 | 2/2019 |
| WO | WO-2019173832 A2 | 9/2019 |
| WO | 2020069398 A1 | 4/2020 |
| WO | 2020125743 A1 | 6/2020 |

OTHER PUBLICATIONS

Office Action from Taiwan Application No. 110132852 dated Feb. 21, 2024.
Office Action from Eurasian Application No. 202390721 dated Mar. 26, 2024.
Office Action from Japanese Application No. 2023-515158 dated Apr. 23, 2024.
Extended Search Report from European Application No. 21863702.3 dated Jul. 19, 2024.
Sprent, J., & Boyman, O. (2024). Optimising IL-2 for Cancer Immunotherapy. Immune network, 24(1).
Mei, L., et al., "Site-Mutation of Hydrophobic Core Residues Synchronically Poise Super Interleukin 2 for Signaling: Identifying Distant Structural Effects through Affordable Computations," Int. J. Mol. Sci., 19(916): 1-23 (2008).
Ghelani, A., et al., "Defining the Threshold IL-2 Signal Required for Induction of Selective Treg Cell Responses Using Engineered IL-2 Muteins," Frontiers in Immunology, 11(1106): 1-19 (2020).
Rao, B.M., et al., "Interleukin-2 mutants with enhanced α-receptor subunit binding affinity," Protein Engineering, 16(12): 1081-1087 (2003).
Levin, A.M., et al., "Exploiting a natural conformational switch to engineer an Interleukin-2 superkine," Nature, 484(7395): 529-533 (2012).
Emerson, S.D., et al., "NMR characterization of interleukin-2 in complexes with the IL-2Rα receptor component, and with low molecular weight compounds that inhibit the IL-2/IL-Rα interaction," Protein Science, 12: 811-822 (2003).
Silva, DA. et al. (2019). De novo design of potent and selective mimics of IL-2 and IL-15. Nature. 565: 186-191.
Office Action from Chilean Application No. 202300631 dated Dec. 23, 2024.
Search Report from Chilean Application No. 202300631 dated Dec. 23, 2024.

*Primary Examiner* — Prema M Mertz
(74) *Attorney, Agent, or Firm* — Harness Dickey & Pierce P.L.C.

(57) ABSTRACT

The present disclosure discloses IL-2 mutants and uses thereof. More specifically, the disclosure provides IL-2 mutants and corresponding fusion proteins, conjugates, nucleic acid fragments, vectors, host cells, methods for preparing the mutants or fusion proteins, IL-2 mutants or fusion proteins prepared according to the methods, pharmaceutical compositions, pharmaceutical uses, methods for treating diseases, and methods for preferentially stimulating regulatory T cells. Compared to wild-type IL-2, the IL-2 mutants of the present disclosure have higher Tm values and improved stability; alternatively, the IL-2 mutants of the present disclosure have an increased yield or changed binding activity to the IL-2Rβγ complexes compared to wild-type IL-2.

14 Claims, 22 Drawing Sheets
Specification includes a Sequence Listing.

SEQUENCE LISTING

<160> NUMBER OF SEQ ID NOS: 60

<210> SEQ ID NO 1
<211> LENGTH: 133
<212> TYPE: PRT
<213> ORGANISM: Homo sapiens

<400> SEQUENCE: 1

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
        130

<210> SEQ ID NO 2
<211> LENGTH: 133
<212> TYPE: PRT
<213> ORGANISM: Artificial Sequence
<220> FEATURE:
<223> OTHER INFORMATION: synthetic polypeptide

<400> SEQUENCE: 2

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Val Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Leu Gln Ser Lys Asn Phe Gln Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
        130

<210> SEQ ID NO 3
<211> LENGTH: 133
<212> TYPE: PRT
<213> ORGANISM: Artificial Sequence

```
<220> FEATURE:
<223> OTHER INFORMATION: synthetic polypeptide

<400> SEQUENCE: 3

Ala Pro Thr Ser Ser Thr Lys Lys Thr Gln Leu Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ala Gln Ser Ile
            115                 120                 125

Ile Ser Thr Leu Thr
            130

<210> SEQ ID NO 4
<211> LENGTH: 133
<212> TYPE: PRT
<213> ORGANISM: Artificial Sequence
<220> FEATURE:
<223> OTHER INFORMATION: synthetic polypeptide

<400> SEQUENCE: 4

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Phe Trp Ile Thr Phe Ala Gln Ser Ile
            115                 120                 125

Ile Ser Thr Leu Thr
            130

<210> SEQ ID NO 5
<211> LENGTH: 133
<212> TYPE: PRT
<213> ORGANISM: Artificial Sequence
<220> FEATURE:
<223> OTHER INFORMATION: synthetic polypeptide

<400> SEQUENCE: 5
```

```
Ala Pro Thr Ser Ser Ser Thr Lys Lys Thr Gln Leu Gln Leu Glu His
1               5                   10                  15

Leu Ile Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Ala Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Trp Leu Asn Arg Trp Ile Thr Phe Ala Gln Ser Ile
            115                 120                 125

Ile Ser Thr Leu Thr
        130

<210> SEQ ID NO 6
<211> LENGTH: 133
<212> TYPE: PRT
<213> ORGANISM: Artificial Sequence
<220> FEATURE:
<223> OTHER INFORMATION: synthetic polypeptide

<400> SEQUENCE: 6

Ala Pro Thr Ser Ser Ser Thr Lys Lys Thr Gln Leu Gln Leu Glu His
1               5                   10                  15

Leu Ile Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Leu Asn Val Ile Ile Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ala Gln Ser Ile
            115                 120                 125

Ile Ser Thr Leu Thr
        130

<210> SEQ ID NO 7
<211> LENGTH: 133
<212> TYPE: PRT
<213> ORGANISM: Artificial Sequence
<220> FEATURE:
<223> OTHER INFORMATION: synthetic polypeptide

<400> SEQUENCE: 7

Ala Pro Thr Ser Ser Ser Thr Lys Lys Thr Gln Leu Gln Leu Glu His
1               5                   10                  15

Leu Leu Leu Asp Leu Gln Met Ile Leu Asn Trp Ile Asn Asn Tyr Lys
            20                  25                  30
```

```
Asn Pro Lys Leu Thr Arg Met Leu Thr Phe Lys Phe Tyr Met Pro Lys
         35                  40                  45

Lys Ala Thr Glu Leu Lys His Leu Gln Cys Leu Glu Glu Glu Leu Lys
     50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Phe Trp Ile Thr Phe Ala Gln Ser Ile
            115                 120                 125

Ile Ser Thr Leu Thr
            130

<210> SEQ ID NO 8
<211> LENGTH: 133
<212> TYPE: PRT
<213> ORGANISM: Artificial Sequence
<220> FEATURE:
<223> OTHER INFORMATION: synthetic polypeptide

<400> SEQUENCE: 8

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                 20                  25                  30

Asn Pro Lys Leu Thr Arg Met Leu Thr Phe Lys Phe Tyr Met Pro Lys
             35                  40                  45

Lys Ala Thr Glu Leu Lys His Leu Gln Cys Leu Glu Glu Glu Leu Lys
     50                  55                  60

Pro Leu Glu Glu Val Leu Asn Leu Ala Gln Ser Lys Asn Phe His Leu
 65                  70                  75                  80

Arg Leu Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Phe Trp Ile Thr Phe Ala Gln Ser Ile
            115                 120                 125

Ile Ser Thr Leu Thr
            130

<210> SEQ ID NO 9
<211> LENGTH: 133
<212> TYPE: PRT
<213> ORGANISM: Artificial Sequence
<220> FEATURE:
<223> OTHER INFORMATION: synthetic polypeptide

<400> SEQUENCE: 9

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                 20                  25                  30

Asn Pro Lys Leu Thr Arg Met Leu Thr Phe Lys Phe Tyr Met Pro Lys
             35                  40                  45

Lys Ala Thr Glu Leu Lys His Leu Gln Cys Leu Glu Glu Glu Leu Lys
```

```
                    50                  55                  60
Pro Leu Glu Glu Val Leu Asn Leu Ala Gln Ser Lys Asn Phe His Leu
 65                  70                  75                  80

Arg Pro Arg Asp Leu Ile Ser Asn Ile Tyr Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Phe Trp Ile Thr Phe Ala Gln Ser Ile
        115                 120                 125

Ile Ser Thr Leu Thr
        130

<210> SEQ ID NO 10
<211> LENGTH: 15
<212> TYPE: PRT
<213> ORGANISM: Artificial Sequence
<220> FEATURE:
<223> OTHER INFORMATION: synthetic polypeptide

<400> SEQUENCE: 10

Gly Gly Gly Gly Ser Gly Gly Gly Gly Ser Gly Gly Gly Gly Ser
 1               5                  10                  15

<210> SEQ ID NO 11
<211> LENGTH: 232
<212> TYPE: PRT
<213> ORGANISM: Artificial Sequence
<220> FEATURE:
<223> OTHER INFORMATION: synthetic polypeptide

<400> SEQUENCE: 11

Glu Pro Lys Ser Ser Asp Lys Thr His Thr Cys Pro Pro Cys Pro Ala
 1               5                  10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Gly Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205
```

Ser Cys Ser Val Met His Glu Ala Leu His Asn His Tyr Thr Gln Lys
            210                 215                 220
Ser Leu Ser Leu Ser Pro Gly Lys
225                 230

<210> SEQ ID NO 12
<211> LENGTH: 380
<212> TYPE: PRT
<213> ORGANISM: Artificial Sequence
<220> FEATURE:
<223> OTHER INFORMATION: synthetic polypeptide

<400> SEQUENCE: 12

Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
            20                  25                  30
Asn Pro Lys Leu Thr Arg Met Leu Thr Phe Lys Phe Tyr Met Pro Lys
        35                  40                  45
Lys Ala Thr Glu Leu Lys His Leu Gln Cys Leu Glu Glu Glu Leu Lys
    50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Ala Gln Ser Ile
        115                 120                 125
Ile Ser Thr Leu Thr Gly Gly Gly Gly Ser Gly Gly Gly Gly Ser Gly
    130                 135                 140
Gly Gly Gly Ser Glu Pro Lys Ser Ser Asp Lys Thr His Thr Cys Pro
145                 150                 155                 160
Pro Cys Pro Ala Pro Glu Leu Leu Gly Gly Pro Ser Val Phe Leu Phe
                165                 170                 175
Pro Pro Lys Pro Lys Asp Thr Leu Met Ile Ser Arg Thr Pro Glu Val
            180                 185                 190
Thr Cys Val Val Val Asp Val Ser His Glu Asp Pro Glu Val Lys Phe
        195                 200                 205
Asn Trp Tyr Val Asp Gly Val Glu Val His Asn Ala Lys Thr Lys Pro
    210                 215                 220
Arg Glu Glu Gln Tyr Gly Ser Thr Tyr Arg Val Val Ser Val Leu Thr
225                 230                 235                 240
Val Leu His Gln Asp Trp Leu Asn Gly Lys Glu Tyr Lys Cys Lys Val
                245                 250                 255
Ser Asn Lys Ala Leu Pro Ala Pro Ile Glu Lys Thr Ile Ser Lys Ala
            260                 265                 270
Lys Gly Gln Pro Arg Glu Pro Gln Val Tyr Thr Leu Pro Pro Ser Arg
        275                 280                 285
Asp Glu Leu Thr Lys Asn Gln Val Ser Leu Thr Cys Leu Val Lys Gly
    290                 295                 300
Phe Tyr Pro Ser Asp Ile Ala Val Glu Trp Glu Ser Asn Gly Gln Pro
305                 310                 315                 320
Glu Asn Asn Tyr Lys Thr Thr Pro Pro Val Leu Asp Ser Asp Gly Ser
                325                 330                 335

Phe Phe Leu Tyr Ser Lys Leu Thr Val Asp Lys Ser Arg Trp Gln Gln
                340                 345                 350

Gly Asn Val Phe Ser Cys Ser Val Met His Glu Ala Leu His Asn His
            355                 360                 365

Tyr Thr Gln Lys Ser Leu Ser Leu Ser Pro Gly Lys
            370                 375                 380

<210> SEQ ID NO 13
<211> LENGTH: 380
<212> TYPE: PRT
<213> ORGANISM: Artificial Sequence
<220> FEATURE:
<223> OTHER INFORMATION: synthetic polypeptide

<400> SEQUENCE: 13

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Val Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Leu Gln Ser Lys Asn Phe Gln Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr Gly Gly Gly Gly Ser Gly Gly Gly Gly Ser Gly
    130                 135                 140

Gly Gly Gly Ser Glu Pro Lys Ser Ser Asp Lys Thr His Thr Cys Pro
145                 150                 155                 160

Pro Cys Pro Ala Pro Glu Leu Leu Gly Gly Pro Ser Val Phe Leu Phe
                165                 170                 175

Pro Pro Lys Pro Lys Asp Thr Leu Met Ile Ser Arg Thr Pro Glu Val
            180                 185                 190

Thr Cys Val Val Val Asp Val Ser His Glu Asp Pro Glu Val Lys Phe
        195                 200                 205

Asn Trp Tyr Val Asp Gly Val Glu Val His Asn Ala Lys Thr Lys Pro
    210                 215                 220

Arg Glu Glu Gln Tyr Gly Ser Thr Tyr Arg Val Val Ser Val Leu Thr
225                 230                 235                 240

Val Leu His Gln Asp Trp Leu Asn Gly Lys Glu Tyr Lys Cys Lys Val
                245                 250                 255

Ser Asn Lys Ala Leu Pro Ala Pro Ile Glu Lys Thr Ile Ser Lys Ala
            260                 265                 270

Lys Gly Gln Pro Arg Glu Pro Gln Val Tyr Thr Leu Pro Pro Ser Arg
        275                 280                 285

Asp Glu Leu Thr Lys Asn Gln Val Ser Leu Thr Cys Leu Val Lys Gly
    290                 295                 300

Phe Tyr Pro Ser Asp Ile Ala Val Glu Trp Glu Ser Asn Gly Gln Pro
305                 310                 315                 320

```
Glu Asn Asn Tyr Lys Thr Thr Pro Val Leu Asp Ser Asp Gly Ser
                325                 330                 335

Phe Phe Leu Tyr Ser Lys Leu Thr Val Asp Lys Ser Arg Trp Gln Gln
            340                 345                 350

Gly Asn Val Phe Ser Cys Ser Val Met His Glu Ala Leu His Asn His
            355                 360                 365

Tyr Thr Gln Lys Ser Leu Ser Leu Ser Pro Gly Lys
            370                 375                 380

<210> SEQ ID NO 14
<211> LENGTH: 380
<212> TYPE: PRT
<213> ORGANISM: Artificial Sequence
<220> FEATURE:
<223> OTHER INFORMATION: synthetic polypeptide

<400> SEQUENCE: 14

Ala Pro Thr Ser Ser Ser Thr Lys Lys Thr Gln Leu Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
            115                 120                 125

Ile Ser Thr Leu Thr Gly Gly Gly Ser Gly Gly Gly Ser Gly
130                 135                 140

Gly Gly Gly Ser Glu Pro Lys Ser Ser Asp Lys Thr His Thr Cys Pro
145                 150                 155                 160

Pro Cys Pro Ala Pro Glu Leu Leu Gly Gly Pro Ser Val Phe Leu Phe
                165                 170                 175

Pro Pro Lys Pro Lys Asp Thr Leu Met Ile Ser Arg Thr Pro Glu Val
            180                 185                 190

Thr Cys Val Val Val Asp Val Ser His Glu Asp Pro Glu Val Lys Phe
            195                 200                 205

Asn Trp Tyr Val Asp Gly Val Glu Val His Asn Ala Lys Thr Lys Pro
210                 215                 220

Arg Glu Glu Gln Tyr Gly Ser Thr Tyr Arg Val Val Ser Val Leu Thr
225                 230                 235                 240

Val Leu His Gln Asp Trp Leu Asn Gly Lys Glu Tyr Lys Cys Lys Val
                245                 250                 255

Ser Asn Lys Ala Leu Pro Ala Pro Ile Glu Lys Thr Ile Ser Lys Ala
            260                 265                 270

Lys Gly Gln Pro Arg Glu Pro Gln Val Tyr Thr Leu Pro Pro Ser Arg
            275                 280                 285

Asp Glu Leu Thr Lys Asn Gln Val Ser Leu Thr Cys Leu Val Lys Gly
            290                 295                 300
```

```
Phe Tyr Pro Ser Asp Ile Ala Val Glu Trp Glu Ser Asn Gly Gln Pro
305                 310                 315                 320

Glu Asn Asn Tyr Lys Thr Thr Pro Pro Val Leu Asp Ser Asp Gly Ser
            325                 330                 335

Phe Phe Leu Tyr Ser Lys Leu Thr Val Asp Lys Ser Arg Trp Gln Gln
            340                 345                 350

Gly Asn Val Phe Ser Cys Ser Val Met His Glu Ala Leu His Asn His
            355                 360                 365

Tyr Thr Gln Lys Ser Leu Ser Leu Ser Pro Gly Lys
            370                 375                 380
```

<210> SEQ ID NO 15
<211> LENGTH: 380
<212> TYPE: PRT
<213> ORGANISM: Artificial Sequence
<220> FEATURE:
<223> OTHER INFORMATION: synthetic polypeptide

<400> SEQUENCE: 15

```
Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Phe Trp Ile Thr Phe Ala Gln Ser Ile
            115                 120                 125

Ile Ser Thr Leu Thr Gly Gly Gly Gly Ser Gly Gly Gly Ser Gly
130                 135                 140

Gly Gly Ser Glu Pro Lys Ser Ser Asp Lys Thr His Thr Cys Pro
145                 150                 155                 160

Pro Cys Pro Ala Pro Glu Leu Leu Gly Gly Pro Ser Val Phe Leu Phe
                165                 170                 175

Pro Pro Lys Pro Lys Asp Thr Leu Met Ile Ser Arg Thr Pro Glu Val
            180                 185                 190

Thr Cys Val Val Val Asp Val Ser His Glu Asp Pro Glu Val Lys Phe
            195                 200                 205

Asn Trp Tyr Val Asp Gly Val Glu Val His Asn Ala Lys Thr Lys Pro
210                 215                 220

Arg Glu Glu Gln Tyr Gly Ser Thr Tyr Arg Val Val Ser Val Leu Thr
225                 230                 235                 240

Val Leu His Gln Asp Trp Leu Asn Gly Lys Glu Tyr Lys Cys Lys Val
                245                 250                 255

Ser Asn Lys Ala Leu Pro Ala Pro Ile Glu Lys Thr Ile Ser Lys Ala
            260                 265                 270

Lys Gly Gln Pro Arg Glu Pro Gln Val Tyr Thr Leu Pro Pro Ser Arg
            275                 280                 285
```

```
Asp Glu Leu Thr Lys Asn Gln Val Ser Leu Thr Cys Leu Val Lys Gly
    290                 295                 300

Phe Tyr Pro Ser Asp Ile Ala Val Glu Trp Glu Ser Asn Gly Gln Pro
305                 310                 315                 320

Glu Asn Asn Tyr Lys Thr Thr Pro Pro Val Leu Asp Ser Asp Gly Ser
                325                 330                 335

Phe Phe Leu Tyr Ser Lys Leu Thr Val Asp Lys Ser Arg Trp Gln Gln
            340                 345                 350

Gly Asn Val Phe Ser Cys Ser Val Met His Glu Ala Leu His Asn His
        355                 360                 365

Tyr Thr Gln Lys Ser Leu Ser Leu Ser Pro Gly Lys
    370                 375                 380

<210> SEQ ID NO 16
<211> LENGTH: 380
<212> TYPE: PRT
<213> ORGANISM: Artificial Sequence
<220> FEATURE:
<223> OTHER INFORMATION: synthetic polypeptide

<400> SEQUENCE: 16

Ala Pro Thr Ser Ser Ser Thr Lys Lys Thr Gln Leu Gln Leu Glu His
1               5                   10                  15

Leu Ile Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Ala Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Trp Leu Asn Arg Trp Ile Thr Phe Ala Gln Ser Ile
        115                 120                 125

Ile Ser Thr Leu Thr Gly Gly Gly Gly Ser Gly Gly Gly Gly Ser Gly
130                 135                 140

Gly Gly Gly Ser Glu Pro Lys Ser Ser Asp Lys Thr His Thr Cys Pro
145                 150                 155                 160

Pro Cys Pro Ala Pro Glu Leu Leu Gly Gly Pro Ser Val Phe Leu Phe
                165                 170                 175

Pro Pro Lys Pro Lys Asp Thr Leu Met Ile Ser Arg Thr Pro Glu Val
            180                 185                 190

Thr Cys Val Val Val Asp Val Ser His Glu Asp Pro Glu Val Lys Phe
        195                 200                 205

Asn Trp Tyr Val Asp Gly Val Glu Val His Asn Ala Lys Thr Lys Pro
    210                 215                 220

Arg Glu Glu Gln Tyr Gly Ser Thr Tyr Arg Val Val Ser Val Leu Thr
225                 230                 235                 240

Val Leu His Gln Asp Trp Leu Asn Gly Lys Glu Tyr Lys Cys Lys Val
                245                 250                 255

Ser Asn Lys Ala Leu Pro Ala Pro Ile Glu Lys Thr Ile Ser Lys Ala
            260                 265                 270
```

Lys Gly Gln Pro Arg Glu Pro Gln Val Tyr Thr Leu Pro Ser Arg
            275                 280                 285

Asp Glu Leu Thr Lys Asn Gln Val Ser Leu Thr Cys Leu Val Lys Gly
        290                 295                 300

Phe Tyr Pro Ser Asp Ile Ala Val Glu Trp Glu Ser Asn Gly Gln Pro
305                 310                 315                 320

Glu Asn Asn Tyr Lys Thr Thr Pro Pro Val Leu Asp Ser Asp Gly Ser
                325                 330                 335

Phe Phe Leu Tyr Ser Lys Leu Thr Val Asp Lys Ser Arg Trp Gln Gln
            340                 345                 350

Gly Asn Val Phe Ser Cys Ser Val Met His Glu Ala Leu His Asn His
            355                 360                 365

Tyr Thr Gln Lys Ser Leu Ser Leu Ser Pro Gly Lys
            370                 375                 380

<210> SEQ ID NO 17
<211> LENGTH: 380
<212> TYPE: PRT
<213> ORGANISM: Artificial Sequence
<220> FEATURE:
<223> OTHER INFORMATION: synthetic polypeptide

<400> SEQUENCE: 17

Ala Pro Thr Ser Ser Ser Thr Lys Lys Thr Gln Leu Gln Leu Glu His
1               5                   10                  15

Leu Ile Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Leu Asn Val Ile Ile Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr Gly Gly Gly Ser Gly Gly Gly Ser Gly
130                 135                 140

Gly Gly Gly Ser Glu Pro Lys Ser Ser Asp Lys Thr His Thr Cys Pro
145                 150                 155                 160

Pro Cys Pro Ala Pro Glu Leu Leu Gly Gly Pro Ser Val Phe Leu Phe
                165                 170                 175

Pro Pro Lys Pro Lys Asp Thr Leu Met Ile Ser Arg Thr Pro Glu Val
            180                 185                 190

Thr Cys Val Val Val Asp Val Ser His Glu Asp Pro Glu Val Lys Phe
        195                 200                 205

Asn Trp Tyr Val Asp Gly Val Glu Val His Asn Ala Lys Thr Lys Pro
    210                 215                 220

Arg Glu Glu Gln Tyr Gly Ser Thr Tyr Arg Val Val Ser Val Leu Thr
225                 230                 235                 240

Val Leu His Gln Asp Trp Leu Asn Gly Lys Glu Tyr Lys Cys Lys Val
                245                 250                 255

```
Ser Asn Lys Ala Leu Pro Ala Pro Ile Glu Lys Thr Ile Ser Lys Ala
            260                 265                 270

Lys Gly Gln Pro Arg Glu Pro Gln Val Tyr Thr Leu Pro Pro Ser Arg
        275                 280                 285

Asp Glu Leu Thr Lys Asn Gln Val Ser Leu Thr Cys Leu Val Lys Gly
    290                 295                 300

Phe Tyr Pro Ser Asp Ile Ala Val Glu Trp Glu Ser Asn Gly Gln Pro
305                 310                 315                 320

Glu Asn Asn Tyr Lys Thr Thr Pro Pro Val Leu Asp Ser Asp Gly Ser
                325                 330                 335

Phe Phe Leu Tyr Ser Lys Leu Thr Val Asp Lys Ser Arg Trp Gln Gln
            340                 345                 350

Gly Asn Val Phe Ser Cys Ser Val Met His Glu Ala Leu His Asn His
        355                 360                 365

Tyr Thr Gln Lys Ser Leu Ser Leu Ser Pro Gly Lys
    370                 375                 380

<210> SEQ ID NO 18
<211> LENGTH: 380
<212> TYPE: PRT
<213> ORGANISM: Artificial Sequence
<220> FEATURE:
<223> OTHER INFORMATION: synthetic polypeptide

<400> SEQUENCE: 18

Ala Pro Thr Ser Ser Thr Lys Lys Thr Gln Leu Gln Leu Glu His
1               5                   10                  15

Leu Leu Leu Asp Leu Gln Met Ile Leu Asn Trp Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Phe Trp Ile Thr Phe Ala Gln Ser Ile
        115                 120                 125

Ile Ser Thr Leu Thr Gly Gly Gly Ser Gly Gly Gly Ser Gly
    130                 135                 140

Gly Gly Gly Ser Glu Pro Lys Ser Ser Asp Lys Thr His Thr Cys Pro
145                 150                 155                 160

Pro Cys Pro Ala Pro Glu Leu Leu Gly Gly Pro Ser Val Phe Leu Phe
                165                 170                 175

Pro Pro Lys Pro Lys Asp Thr Leu Met Ile Ser Arg Thr Pro Glu Val
            180                 185                 190

Thr Cys Val Val Val Asp Val Ser His Glu Asp Pro Glu Val Lys Phe
        195                 200                 205

Asn Trp Tyr Val Asp Gly Val Glu Val His Asn Ala Lys Thr Lys Pro
    210                 215                 220

Arg Glu Glu Gln Tyr Gly Ser Thr Tyr Arg Val Val Ser Val Leu Thr
225                 230                 235                 240
```

Val Leu His Gln Asp Trp Leu Asn Gly Lys Glu Tyr Lys Cys Lys Val
             245                 250                 255

Ser Asn Lys Ala Leu Pro Ala Pro Ile Glu Lys Thr Ile Ser Lys Ala
         260                 265                 270

Lys Gly Gln Pro Arg Glu Pro Gln Val Tyr Thr Leu Pro Pro Ser Arg
     275                 280                 285

Asp Glu Leu Thr Lys Asn Gln Val Ser Leu Thr Cys Leu Val Lys Gly
 290                 295                 300

Phe Tyr Pro Ser Asp Ile Ala Val Glu Trp Glu Ser Asn Gly Gln Pro
305                 310                 315                 320

Glu Asn Asn Tyr Lys Thr Thr Pro Pro Val Leu Asp Ser Asp Gly Ser
             325                 330                 335

Phe Phe Leu Tyr Ser Lys Leu Thr Val Asp Lys Ser Arg Trp Gln Gln
         340                 345                 350

Gly Asn Val Phe Ser Cys Ser Val Met His Glu Ala Leu His Asn His
     355                 360                 365

Tyr Thr Gln Lys Ser Leu Ser Leu Ser Pro Gly Lys
 370                 375                 380

<210> SEQ ID NO 19
<211> LENGTH: 380
<212> TYPE: PRT
<213> ORGANISM: Artificial Sequence
<220> FEATURE:
<223> OTHER INFORMATION: synthetic polypeptide

<400> SEQUENCE: 19

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
             20                  25                  30

Asn Pro Lys Leu Thr Arg Met Leu Thr Phe Lys Phe Tyr Met Pro Lys
         35                  40                  45

Lys Ala Thr Glu Leu Lys His Leu Gln Cys Leu Glu Glu Glu Leu Lys
     50                  55                  60

Pro Leu Glu Glu Val Leu Asn Leu Ala Gln Ser Lys Asn Phe His Leu
65                  70                  75                  80

Arg Leu Arg Asp Leu Ile Ser Asn Ile Asn Val Ile Val Leu Glu Leu
             85                  90                  95

Lys Gly Ser Glu Thr Thr Phe Met Cys Glu Tyr Ala Asp Glu Thr Ala
         100                 105                 110

Thr Ile Val Glu Phe Leu Asn Phe Trp Ile Thr Phe Ala Gln Ser Ile
     115                 120                 125

Ile Ser Thr Leu Thr Gly Gly Gly Gly Ser Gly Gly Gly Gly Ser Gly
 130                 135                 140

Gly Gly Gly Ser Glu Pro Lys Ser Ser Asp Lys Thr His Thr Cys Pro
145                 150                 155                 160

Pro Cys Pro Ala Pro Glu Leu Leu Gly Gly Pro Ser Val Phe Leu Phe
             165                 170                 175

Pro Pro Lys Pro Lys Asp Thr Leu Met Ile Ser Arg Thr Pro Glu Val
         180                 185                 190

Thr Cys Val Val Val Asp Val Ser His Glu Asp Pro Glu Val Lys Phe
     195                 200                 205

Asn Trp Tyr Val Asp Gly Val Glu Val His Asn Ala Lys Thr Lys Pro
 210                 215                 220

```
Arg Glu Glu Gln Tyr Gly Ser Thr Tyr Arg Val Ser Val Leu Thr
225                 230                 235                 240

Val Leu His Gln Asp Trp Leu Asn Gly Lys Glu Tyr Lys Cys Lys Val
            245                 250                 255

Ser Asn Lys Ala Leu Pro Ala Pro Ile Glu Lys Thr Ile Ser Lys Ala
            260                 265                 270

Lys Gly Gln Pro Arg Glu Pro Gln Val Tyr Thr Leu Pro Pro Ser Arg
            275                 280                 285

Asp Glu Leu Thr Lys Asn Gln Val Ser Leu Thr Cys Leu Val Lys Gly
            290                 295                 300

Phe Tyr Pro Ser Asp Ile Ala Val Glu Trp Glu Ser Asn Gly Gln Pro
305                 310                 315                 320

Glu Asn Asn Tyr Lys Thr Thr Pro Pro Val Leu Asp Ser Asp Gly Ser
                325                 330                 335

Phe Phe Leu Tyr Ser Lys Leu Thr Val Asp Lys Ser Arg Trp Gln Gln
                340                 345                 350

Gly Asn Val Phe Ser Cys Ser Val Met His Glu Ala Leu His Asn His
            355                 360                 365

Tyr Thr Gln Lys Ser Leu Ser Leu Ser Pro Gly Lys
            370                 375                 380

<210> SEQ ID NO 20
<211> LENGTH: 380
<212> TYPE: PRT
<213> ORGANISM: Artificial Sequence
<220> FEATURE:
<223> OTHER INFORMATION: synthetic polypeptide

<400> SEQUENCE: 20

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Tyr Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Phe Trp Ile Thr Phe Ala Gln Ser Ile
        115                 120                 125

Ile Ser Thr Leu Thr Gly Gly Gly Ser Gly Gly Gly Ser Gly
    130                 135                 140

Gly Gly Gly Ser Glu Pro Lys Ser Ser Asp Lys Thr His Thr Cys Pro
145                 150                 155                 160

Pro Cys Pro Ala Pro Glu Leu Leu Gly Gly Pro Ser Val Phe Leu Phe
                165                 170                 175

Pro Pro Lys Pro Lys Asp Thr Leu Met Ile Ser Arg Thr Pro Glu Val
            180                 185                 190

Thr Cys Val Val Val Asp Val Ser His Glu Asp Pro Glu Val Lys Phe
        195                 200                 205
```

```
Asn Trp Tyr Val Asp Gly Val Glu Val His Asn Ala Lys Thr Lys Pro
    210                 215                 220
Arg Glu Glu Gln Tyr Gly Ser Thr Tyr Arg Val Val Ser Val Leu Thr
225                 230                 235                 240
Val Leu His Gln Asp Trp Leu Asn Gly Lys Glu Tyr Lys Cys Lys Val
            245                 250                 255
Ser Asn Lys Ala Leu Pro Ala Pro Ile Glu Lys Thr Ile Ser Lys Ala
        260                 265                 270
Lys Gly Gln Pro Arg Glu Pro Gln Val Tyr Thr Leu Pro Pro Ser Arg
    275                 280                 285
Asp Glu Leu Thr Lys Asn Gln Val Ser Leu Thr Cys Leu Val Lys Gly
290                 295                 300
Phe Tyr Pro Ser Asp Ile Ala Val Glu Trp Glu Ser Asn Gly Gln Pro
305                 310                 315                 320
Glu Asn Asn Tyr Lys Thr Thr Pro Pro Val Leu Asp Ser Asp Gly Ser
            325                 330                 335
Phe Phe Leu Tyr Ser Lys Leu Thr Val Asp Lys Ser Arg Trp Gln Gln
        340                 345                 350
Gly Asn Val Phe Ser Cys Ser Val Met His Glu Ala Leu His Asn His
    355                 360                 365
Tyr Thr Gln Lys Ser Leu Ser Leu Ser Pro Gly Lys
370                 375                 380

<210> SEQ ID NO 21
<211> LENGTH: 133
<212> TYPE: PRT
<213> ORGANISM: Artificial Sequence
<220> FEATURE:
<223> OTHER INFORMATION: synthetic polypeptide

<400> SEQUENCE: 21

Ala Pro Thr Ser Ser Thr Lys Lys Thr Gln Leu Gln Leu Glu Glu Glu
1               5                   10                  15
Leu Leu Leu Asp Leu Gln Met Ile Leu Asn Gly Ile Asn Asn Tyr Lys
            20                  25                  30
Asn Pro Lys Leu Thr Arg Met Leu Thr Phe Lys Phe Tyr Met Pro Lys
        35                  40                  45
Lys Ala Thr Glu Leu Lys His Leu Gln Cys Leu Glu Glu Glu Leu Lys
    50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Ala Gln Ser Ile
        115                 120                 125
Ile Ser Thr Leu Thr
    130

<210> SEQ ID NO 22
<211> LENGTH: 133
<212> TYPE: PRT
<213> ORGANISM: Artificial Sequence
<220> FEATURE:
<223> OTHER INFORMATION: synthetic polypeptide

<400> SEQUENCE: 22
```

```
Ala Pro Thr Ser Ser Thr Lys Lys Thr Gln Leu Gln Leu Glu Glu
1               5                   10                  15

Leu Leu Leu Asp Leu Gln Met Ile Leu Asn Gly Ile Asn Asn Val Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
50                  55                  60

Pro Leu Glu Glu Val Leu Asn Leu Leu Gln Ser Lys Asn Phe Gln Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ala Gln Ser Ile
            115                 120                 125

Ile Ser Thr Leu Thr
        130

<210> SEQ ID NO 23
<211> LENGTH: 133
<212> TYPE: PRT
<213> ORGANISM: Artificial Sequence
<220> FEATURE:
<223> OTHER INFORMATION: synthetic polypeptide

<400> SEQUENCE: 23

Ala Pro Thr Ser Ser Thr Lys Lys Thr Gln Leu Gln Leu Glu Glu
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Phe Trp Ile Thr Phe Ala Gln Ser Ile
            115                 120                 125

Ile Ser Thr Leu Thr
        130

<210> SEQ ID NO 24
<211> LENGTH: 133
<212> TYPE: PRT
<213> ORGANISM: Artificial Sequence
<220> FEATURE:
<223> OTHER INFORMATION: synthetic polypeptide

<400> SEQUENCE: 24

Ala Pro Thr Ser Ser Thr Lys Lys Thr Gln Leu Gln Leu Glu Glu
1               5                   10                  15

Leu Ile Leu Asp Leu Gln Met Ile Leu Asn Gly Ile Asn Asn Tyr Lys
```

```
                  20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Ala Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Trp Leu Asn Arg Trp Ile Thr Phe Ala Gln Ser Ile
        115                 120                 125

Ile Ser Thr Leu Thr
        130

<210> SEQ ID NO 25
<211> LENGTH: 133
<212> TYPE: PRT
<213> ORGANISM: Artificial Sequence
<220> FEATURE:
<223> OTHER INFORMATION: synthetic polypeptide

<400> SEQUENCE: 25

Ala Pro Thr Ser Ser Ser Thr Lys Lys Thr Gln Leu Gln Leu Glu Glu
 1               5                  10                  15

Leu Ile Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Leu Asn Val Ile Ile Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
        130

<210> SEQ ID NO 26
<211> LENGTH: 133
<212> TYPE: PRT
<213> ORGANISM: Artificial Sequence
<220> FEATURE:
<223> OTHER INFORMATION: synthetic polypeptide

<400> SEQUENCE: 26

Ala Pro Thr Ser Ser Ser Thr Lys Lys Thr Gln Leu Gln Leu Glu Glu
 1               5                  10                  15

Leu Leu Leu Asp Leu Gln Met Ile Leu Asn Trp Ile Asn Asn Tyr Lys
                20                  25                  30

Asn Pro Lys Leu Thr Arg Met Leu Thr Phe Lys Phe Tyr Met Pro Lys
            35                  40                  45
```

```
Lys Ala Thr Glu Leu Lys His Leu Gln Cys Leu Glu Glu Leu Lys
     50                   55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Phe Trp Ile Thr Phe Ala Gln Ser Ile
                115                 120                 125

Ile Ser Thr Leu Thr
            130

<210> SEQ ID NO 27
<211> LENGTH: 133
<212> TYPE: PRT
<213> ORGANISM: Artificial Sequence
<220> FEATURE:
<223> OTHER INFORMATION: synthetic polypeptide

<400> SEQUENCE: 27

Ala Pro Thr Ser Ser Ser Thr Lys Lys Thr Gln Leu Gln Leu Glu Glu
  1               5                  10                  15

Leu Leu Leu Asp Leu Gln Met Ile Leu Asn Gly Ile Asn Asn Tyr Lys
                 20                  25                  30

Asn Pro Lys Leu Thr Arg Met Leu Thr Phe Lys Phe Tyr Met Pro Lys
                 35                  40                  45

Lys Ala Thr Glu Leu Lys His Leu Gln Cys Leu Glu Glu Leu Lys
     50                   55                  60

Pro Leu Glu Glu Val Leu Asn Leu Ala Gln Ser Lys Asn Phe His Leu
 65                  70                  75                  80

Arg Leu Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Phe Trp Ile Thr Phe Ala Gln Ser Ile
                115                 120                 125

Ile Ser Thr Leu Thr
            130

<210> SEQ ID NO 28
<211> LENGTH: 133
<212> TYPE: PRT
<213> ORGANISM: Artificial Sequence
<220> FEATURE:
<223> OTHER INFORMATION: synthetic polypeptide

<400> SEQUENCE: 28

Ala Pro Thr Ser Ser Ser Thr Lys Lys Thr Gln Leu Gln Leu Glu His
  1               5                  10                  15

Leu Leu Leu Ala Leu Gln Met Ile Leu Asn Gly Ile Asn Asn Tyr Lys
                 20                  25                  30

Asn Pro Lys Leu Thr Arg Met Leu Thr Phe Lys Phe Tyr Met Pro Lys
                 35                  40                  45

Lys Ala Thr Glu Leu Lys His Leu Gln Cys Leu Glu Glu Leu Lys
     50                   55                  60

Pro Leu Glu Glu Val Leu Asn Leu Ala Gln Ser Lys Asn Phe His Leu
 65                  70                  75                  80
```

```
Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
        130

<210> SEQ ID NO 29
<211> LENGTH: 133
<212> TYPE: PRT
<213> ORGANISM: Artificial Sequence
<220> FEATURE:
<223> OTHER INFORMATION: synthetic polypeptide

<400> SEQUENCE: 29

Ala Pro Thr Ser Ser Ser Thr Lys Lys Thr Gln Leu Gln Leu Glu His
1               5                   10                  15

Leu Leu Leu Ala Leu Gln Met Ile Leu Asn Gly Ile Asn Asn Val Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Leu Gln Ser Lys Asn Phe Gln Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
        130

<210> SEQ ID NO 30
<211> LENGTH: 133
<212> TYPE: PRT
<213> ORGANISM: Artificial Sequence
<220> FEATURE:
<223> OTHER INFORMATION: synthetic polypeptide

<400> SEQUENCE: 30

Ala Pro Thr Ser Ser Ser Thr Lys Lys Thr Gln Leu Gln Leu Glu His
1               5                   10                  15

Leu Leu Leu Ala Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
```

```
                    100                 105                 110
Thr Ile Val Glu Phe Leu Asn Phe Trp Ile Thr Phe Ala Gln Ser Ile
            115                 120                 125

Ile Ser Thr Leu Thr
        130

<210> SEQ ID NO 31
<211> LENGTH: 133
<212> TYPE: PRT
<213> ORGANISM: Artificial Sequence
<220> FEATURE:
<223> OTHER INFORMATION: synthetic polypeptide

<400> SEQUENCE: 31

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Arg Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
        130

<210> SEQ ID NO 32
<211> LENGTH: 133
<212> TYPE: PRT
<213> ORGANISM: Artificial Sequence
<220> FEATURE:
<223> OTHER INFORMATION: synthetic polypeptide

<400> SEQUENCE: 32

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Val Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Leu Gln Ser Lys Asn Phe Gln Leu
65                  70                  75                  80

Arg Pro Arg Asp Leu Ile Ser Asn Ile Asn Arg Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125
```

```
Ile Ser Thr Leu Thr
    130

<210> SEQ ID NO 33
<211> LENGTH: 133
<212> TYPE: PRT
<213> ORGANISM: Artificial Sequence
<220> FEATURE:
<223> OTHER INFORMATION: synthetic polypeptide

<400> SEQUENCE: 33

Ala Pro Thr Ser Ser Thr Lys Lys Thr Gln Leu Leu Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Arg Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
    130

<210> SEQ ID NO 34
<211> LENGTH: 133
<212> TYPE: PRT
<213> ORGANISM: Artificial Sequence
<220> FEATURE:
<223> OTHER INFORMATION: synthetic polypeptide

<400> SEQUENCE: 34

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Arg Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Phe Trp Ile Thr Phe Ala Gln Ser Ile
        115                 120                 125

Ile Ser Thr Leu Thr
    130

<210> SEQ ID NO 35
```

```
<211> LENGTH: 133
<212> TYPE: PRT
<213> ORGANISM: Artificial Sequence
<220> FEATURE:
<223> OTHER INFORMATION: synthetic polypeptide

<400> SEQUENCE: 35

Ala Pro Thr Ser Ser Ser Thr Lys Lys Thr Gln Leu Gln Leu Glu His
1               5                   10                  15

Leu Ile Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Leu Asn Arg Ile Ile Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
        130

<210> SEQ ID NO 36
<211> LENGTH: 133
<212> TYPE: PRT
<213> ORGANISM: Artificial Sequence
<220> FEATURE:
<223> OTHER INFORMATION: synthetic polypeptide

<400> SEQUENCE: 36

Ala Pro Thr Ser Ser Ser Thr Lys Lys Thr Gln Leu Gln Leu Glu Glu
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Arg Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
        130

<210> SEQ ID NO 37
<211> LENGTH: 133
<212> TYPE: PRT
<213> ORGANISM: Artificial Sequence
<220> FEATURE:
<223> OTHER INFORMATION: synthetic polypeptide
```

<400> SEQUENCE: 37

Ala Pro Thr Ser Ser Ser Thr Lys Lys Thr Gln Leu Gln Leu Glu Glu
1               5                   10                  15

Leu Leu Leu Asp Leu Gln Met Ile Leu Asn Gly Ile Asn Asn Val Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Leu Gln Ser Lys Asn Phe Gln Leu
65                  70                  75                  80

Arg Pro Arg Asp Leu Ile Ser Asn Ile Asn Arg Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
            115                 120                 125

Ile Ser Thr Leu Thr
        130

<210> SEQ ID NO 38
<211> LENGTH: 133
<212> TYPE: PRT
<213> ORGANISM: Artificial Sequence
<220> FEATURE:
<223> OTHER INFORMATION: synthetic polypeptide

<400> SEQUENCE: 38

Ala Pro Thr Ser Ser Ser Thr Lys Lys Thr Gln Leu Gln Leu Glu Glu
1               5                   10                  15

Leu Ile Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Leu Asn Arg Ile Ile Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
            115                 120                 125

Ile Ser Thr Leu Thr
        130

<210> SEQ ID NO 39
<211> LENGTH: 380
<212> TYPE: PRT
<213> ORGANISM: Artificial Sequence
<220> FEATURE:
<223> OTHER INFORMATION: synthetic polypeptide

<400> SEQUENCE: 39

Ala Pro Thr Ser Ser Ser Thr Lys Lys Thr Gln Leu Gln Leu Glu Glu
1               5                   10                  15

```
Leu Leu Leu Asp Leu Gln Met Ile Leu Asn Gly Ile Asn Asn Tyr Lys
         20                  25                  30

Asn Pro Lys Leu Thr Arg Met Leu Thr Phe Lys Phe Tyr Met Pro Lys
         35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ala Gln Ser Ile
                115                 120                 125

Ile Ser Thr Leu Thr Gly Gly Gly Ser Gly Gly Gly Ser Gly
130                 135                 140

Gly Gly Gly Ser Glu Pro Lys Ser Ser Asp Lys Thr His Thr Cys Pro
145                 150                 155                 160

Pro Cys Pro Ala Pro Glu Leu Leu Gly Gly Pro Ser Val Phe Leu Phe
                165                 170                 175

Pro Pro Lys Pro Lys Asp Thr Leu Met Ile Ser Arg Thr Pro Glu Val
                180                 185                 190

Thr Cys Val Val Val Asp Val Ser His Glu Asp Pro Glu Val Lys Phe
                195                 200                 205

Asn Trp Tyr Val Asp Gly Val Glu Val His Asn Ala Lys Thr Lys Pro
210                 215                 220

Arg Glu Glu Gln Tyr Gly Ser Thr Tyr Arg Val Val Ser Val Leu Thr
225                 230                 235                 240

Val Leu His Gln Asp Trp Leu Asn Gly Lys Glu Tyr Lys Cys Lys Val
                245                 250                 255

Ser Asn Lys Ala Leu Pro Ala Pro Ile Glu Lys Thr Ile Ser Lys Ala
                260                 265                 270

Lys Gly Gln Pro Arg Glu Pro Gln Val Tyr Thr Leu Pro Pro Ser Arg
                275                 280                 285

Asp Glu Leu Thr Lys Asn Gln Val Ser Leu Thr Cys Leu Val Lys Gly
290                 295                 300

Phe Tyr Pro Ser Asp Ile Ala Val Glu Trp Glu Ser Asn Gly Gln Pro
305                 310                 315                 320

Glu Asn Asn Tyr Lys Thr Thr Pro Pro Val Leu Asp Ser Asp Gly Ser
                325                 330                 335

Phe Phe Leu Tyr Ser Lys Leu Thr Val Asp Lys Ser Arg Trp Gln Gln
                340                 345                 350

Gly Asn Val Phe Ser Cys Ser Val Met His Glu Ala Leu His Asn His
                355                 360                 365

Tyr Thr Gln Lys Ser Leu Ser Leu Ser Pro Gly Lys
                370                 375                 380

<210> SEQ ID NO 40
<211> LENGTH: 380
<212> TYPE: PRT
<213> ORGANISM: Artificial Sequence
<220> FEATURE:
<223> OTHER INFORMATION: synthetic polypeptide

<400> SEQUENCE: 40
```

-continued

```
Ala Pro Thr Ser Ser Thr Lys Lys Thr Gln Leu Gln Leu Glu Glu
1               5                   10                  15

Leu Leu Leu Asp Leu Gln Met Ile Leu Asn Gly Ile Asn Asn Val Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Leu Gln Ser Lys Asn Phe Gln Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
            115                 120                 125

Ile Ser Thr Leu Thr Gly Gly Gly Ser Gly Gly Gly Ser Gly
130                 135                 140

Gly Gly Gly Ser Glu Pro Lys Ser Ser Asp Lys Thr His Thr Cys Pro
145                 150                 155                 160

Pro Cys Pro Ala Pro Glu Leu Leu Gly Gly Pro Ser Val Phe Leu Phe
            165                 170                 175

Pro Pro Lys Pro Lys Asp Thr Leu Met Ile Ser Arg Thr Pro Glu Val
            180                 185                 190

Thr Cys Val Val Val Asp Val Ser His Glu Asp Pro Glu Val Lys Phe
            195                 200                 205

Asn Trp Tyr Val Asp Gly Val Glu Val His Asn Ala Lys Thr Lys Pro
            210                 215                 220

Arg Glu Glu Gln Tyr Gly Ser Thr Tyr Arg Val Val Ser Val Leu Thr
225                 230                 235                 240

Val Leu His Gln Asp Trp Leu Asn Gly Lys Glu Tyr Lys Cys Lys Val
                245                 250                 255

Ser Asn Lys Ala Leu Pro Ala Pro Ile Glu Lys Thr Ile Ser Lys Ala
            260                 265                 270

Lys Gly Gln Pro Arg Glu Pro Gln Val Tyr Thr Leu Pro Pro Ser Arg
            275                 280                 285

Asp Glu Leu Thr Lys Asn Gln Val Ser Leu Thr Cys Leu Val Lys Gly
            290                 295                 300

Phe Tyr Pro Ser Asp Ile Ala Val Glu Trp Glu Ser Asn Gly Gln Pro
305                 310                 315                 320

Glu Asn Asn Tyr Lys Thr Thr Pro Pro Val Leu Asp Ser Asp Gly Ser
                325                 330                 335

Phe Phe Leu Tyr Ser Lys Leu Thr Val Asp Lys Ser Arg Trp Gln Gln
            340                 345                 350

Gly Asn Val Phe Ser Cys Ser Val Met His Glu Ala Leu His Asn His
            355                 360                 365

Tyr Thr Gln Lys Ser Leu Ser Leu Ser Pro Gly Lys
            370                 375                 380

<210> SEQ ID NO 41
<211> LENGTH: 380
<212> TYPE: PRT
<213> ORGANISM: Artificial Sequence
<220> FEATURE:
```

<223> OTHER INFORMATION: synthetic polypeptide

<400> SEQUENCE: 41

```
Ala Pro Thr Ser Ser Thr Lys Lys Thr Gln Leu Gln Leu Glu
1               5                   10                  15
Glu

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
            50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Phe Trp Ile Thr Phe Ala Gln Ser Ile
                115                 120                 125

Ile Ser Thr Leu Thr Gly Gly Gly Gly Ser Gly Gly Gly Ser Gly
130                 135                 140

Gly Gly Ser Glu Pro Lys Ser Ser Asp Lys Thr His Thr Cys Pro
145                 150                 155                 160

Pro Cys Pro Ala Pro Glu Leu Leu Gly Gly Pro Ser Val Phe Leu Phe
                165                 170                 175

Pro Pro Lys Pro Lys Asp Thr Leu Met Ile Ser Arg Thr Pro Glu Val
                180                 185                 190

Thr Cys Val Val Val Asp Val Ser His Glu Asp Pro Glu Val Lys Phe
                195                 200                 205

Asn Trp Tyr Val Asp Gly Val Glu Val His Asn Ala Lys Thr Lys Pro
                210                 215                 220

Arg Glu Glu Gln Tyr Gly Ser Thr Tyr Arg Val Val Ser Val Leu Thr
225                 230                 235                 240

Val Leu His Gln Asp Trp Leu Asn Gly Lys Glu Tyr Lys Cys Lys Val
                245                 250                 255

Ser Asn Lys Ala Leu Pro Ala Pro Ile Glu Lys Thr Ile Ser Lys Ala
                260                 265                 270

Lys Gly Gln Pro Arg Glu Pro Gln Val Tyr Thr Leu Pro Pro Ser Arg
                275                 280                 285

Asp Glu Leu Thr Lys Asn Gln Val Ser Leu Thr Cys Leu Val Lys Gly
                290                 295                 300

Phe Tyr Pro Ser Asp Ile Ala Val Glu Trp Glu Ser Asn Gly Gln Pro
305                 310                 315                 320

Glu Asn Asn Tyr Lys Thr Thr Pro Pro Val Leu Asp Ser Asp Gly Ser
                325                 330                 335

Phe Phe Leu Tyr Ser Lys Leu Thr Val Asp Lys Ser Arg Trp Gln Gln
                340                 345                 350

Gly Asn Val Phe Ser Cys Ser Val Met His Glu Ala Leu His Asn His
                355                 360                 365

Tyr Thr Gln Lys Ser Leu Ser Leu Ser Pro Gly Lys
                370                 375                 380
```

<210> SEQ ID NO 42
<211> LENGTH: 380

```
<212> TYPE: PRT
<213> ORGANISM: Artificial Sequence
<220> FEATURE:
<223> OTHER INFORMATION: synthetic polypeptide

<400> SEQUENCE: 42
```

| | | | | | | | | | | | | | | |
|---|---|---|---|---|---|---|---|---|---|---|---|---|---|---|
| Ala | Pro | Thr | Ser | Ser | Thr | Lys | Lys | Thr | Gln | Leu | Gln | Leu | Glu | Glu |
| 1 | | | | 5 | | | | | 10 | | | | | 15 |

| | | | | | | | | | | | | | | |
|---|---|---|---|---|---|---|---|---|---|---|---|---|---|---|
| Leu | Ile | Leu | Asp | Leu | Gln | Met | Ile | Leu | Asn | Gly | Ile | Asn | Asn | Tyr | Lys |
| | | | 20 | | | | | 25 | | | | | 30 | |

| | | | | | | | | | | | | | |
|---|---|---|---|---|---|---|---|---|---|---|---|---|---|
| Asn | Pro | Lys | Leu | Thr | Arg | Met | Leu | Thr | Phe | Lys | Phe | Tyr | Met | Pro | Lys |
| | | 35 | | | | | 40 | | | | | 45 | | |

| | | | | | | | | | | | | | |
|---|---|---|---|---|---|---|---|---|---|---|---|---|---|
| Lys | Ala | Thr | Glu | Leu | Lys | His | Leu | Gln | Cys | Leu | Glu | Glu | Glu | Leu | Lys |
| 50 | | | | | 55 | | | | | 60 | | | | |

| | | | | | | | | | | | | | |
|---|---|---|---|---|---|---|---|---|---|---|---|---|---|
| Pro | Leu | Glu | Glu | Val | Leu | Asn | Leu | Ala | Gln | Ser | Lys | Asn | Phe | His | Leu |
| 65 | | | | 70 | | | | | 75 | | | | | 80 |

| | | | | | | | | | | | | | |
|---|---|---|---|---|---|---|---|---|---|---|---|---|---|
| Arg | Pro | Arg | Asp | Leu | Ile | Ser | Asn | Ile | Asn | Ala | Ile | Val | Leu | Glu | Leu |
| | | | | 85 | | | | | 90 | | | | | 95 |

| | | | | | | | | | | | | | |
|---|---|---|---|---|---|---|---|---|---|---|---|---|---|
| Lys | Gly | Ser | Glu | Thr | Thr | Phe | Met | Cys | Glu | Tyr | Ala | Asp | Glu | Thr | Ala |
| | | | 100 | | | | | 105 | | | | | 110 | |

| | | | | | | | | | | | | | |
|---|---|---|---|---|---|---|---|---|---|---|---|---|---|
| Thr | Ile | Val | Glu | Trp | Leu | Asn | Arg | Trp | Ile | Thr | Phe | Ala | Gln | Ser | Ile |
| | | 115 | | | | | 120 | | | | | 125 | | |

| | | | | | | | | | | | | | |
|---|---|---|---|---|---|---|---|---|---|---|---|---|---|
| Ile | Ser | Thr | Leu | Thr | Gly | Gly | Gly | Ser | Gly | Gly | Gly | Ser | Gly |
| 130 | | | | | 135 | | | | | 140 | | | |

| | | | | | | | | | | | | | |
|---|---|---|---|---|---|---|---|---|---|---|---|---|---|
| Gly | Gly | Gly | Ser | Glu | Pro | Lys | Ser | Ser | Asp | Lys | Thr | His | Thr | Cys | Pro |
| 145 | | | | | 150 | | | | | 155 | | | | | 160 |

| | | | | | | | | | | | | | |
|---|---|---|---|---|---|---|---|---|---|---|---|---|---|
| Pro | Cys | Pro | Ala | Pro | Glu | Leu | Leu | Gly | Gly | Pro | Ser | Val | Phe | Leu | Phe |
| | | | | 165 | | | | | 170 | | | | | 175 |

| | | | | | | | | | | | | | |
|---|---|---|---|---|---|---|---|---|---|---|---|---|---|
| Pro | Pro | Lys | Pro | Lys | Asp | Thr | Leu | Met | Ile | Ser | Arg | Thr | Pro | Glu | Val |
| | | | 180 | | | | | 185 | | | | | 190 | |

| | | | | | | | | | | | | | |
|---|---|---|---|---|---|---|---|---|---|---|---|---|---|
| Thr | Cys | Val | Val | Val | Asp | Val | Ser | His | Glu | Asp | Pro | Glu | Val | Lys | Phe |
| | | 195 | | | | | 200 | | | | | 205 | | |

| | | | | | | | | | | | | | |
|---|---|---|---|---|---|---|---|---|---|---|---|---|---|
| Asn | Trp | Tyr | Val | Asp | Gly | Val | Glu | Val | His | Asn | Ala | Lys | Thr | Lys | Pro |
| 210 | | | | | 215 | | | | | 220 | | | | | |

| | | | | | | | | | | | | | |
|---|---|---|---|---|---|---|---|---|---|---|---|---|---|
| Arg | Glu | Glu | Gln | Tyr | Gly | Ser | Thr | Tyr | Arg | Val | Val | Ser | Val | Leu | Thr |
| 225 | | | | | 230 | | | | | 235 | | | | | 240 |

| | | | | | | | | | | | | | |
|---|---|---|---|---|---|---|---|---|---|---|---|---|---|
| Val | Leu | His | Gln | Asp | Trp | Leu | Asn | Gly | Lys | Glu | Tyr | Lys | Cys | Lys | Val |
| | | | | 245 | | | | | 250 | | | | | 255 |

| | | | | | | | | | | | | | |
|---|---|---|---|---|---|---|---|---|---|---|---|---|---|
| Ser | Asn | Lys | Ala | Leu | Pro | Ala | Pro | Ile | Glu | Lys | Thr | Ile | Ser | Lys | Ala |
| | | | 260 | | | | | 265 | | | | | 270 | | |

| | | | | | | | | | | | | | |
|---|---|---|---|---|---|---|---|---|---|---|---|---|---|
| Lys | Gly | Gln | Pro | Arg | Glu | Pro | Gln | Val | Tyr | Thr | Leu | Pro | Pro | Ser | Arg |
| | | | 275 | | | | | 280 | | | | | 285 | | |

| | | | | | | | | | | | | | |
|---|---|---|---|---|---|---|---|---|---|---|---|---|---|
| Asp | Glu | Leu | Thr | Lys | Asn | Gln | Val | Ser | Leu | Thr | Cys | Leu | Val | Lys | Gly |
| | | 290 | | | | | 295 | | | | | 300 | | |

| | | | | | | | | | | | | | |
|---|---|---|---|---|---|---|---|---|---|---|---|---|---|
| Phe | Tyr | Pro | Ser | Asp | Ile | Ala | Val | Glu | Trp | Glu | Ser | Asn | Gly | Gln | Pro |
| 305 | | | | | 310 | | | | | 315 | | | | | 320 |

| | | | | | | | | | | | | | |
|---|---|---|---|---|---|---|---|---|---|---|---|---|---|
| Glu | Asn | Asn | Tyr | Lys | Thr | Thr | Pro | Pro | Val | Leu | Asp | Ser | Asp | Gly | Ser |
| | | | | 325 | | | | | 330 | | | | | 335 |

| | | | | | | | | | | | | | |
|---|---|---|---|---|---|---|---|---|---|---|---|---|---|
| Phe | Phe | Leu | Tyr | Ser | Lys | Leu | Thr | Val | Asp | Lys | Ser | Arg | Trp | Gln | Gln |
| | | | 340 | | | | | 345 | | | | | 350 | | |

| | | | | | | | | | | | | | |
|---|---|---|---|---|---|---|---|---|---|---|---|---|---|
| Gly | Asn | Val | Phe | Ser | Cys | Ser | Val | Met | His | Glu | Ala | Leu | His | Asn | His |
| | | | 355 | | | | | 360 | | | | | 365 | | |

| | | | | | | | | | |
|---|---|---|---|---|---|---|---|---|---|
| Tyr | Thr | Gln | Lys | Ser | Leu | Ser | Leu | Ser | Pro | Gly | Lys |
| | 370 | | | | | 375 | | | | | 380 |

```
<210> SEQ ID NO 43
<211> LENGTH: 380
<212> TYPE: PRT
<213> ORGANISM: Artificial Sequence
<220> FEATURE:
<223> OTHER INFORMATION: synthetic polypeptide

<400> SEQUENCE: 43
```

| | | | | | | | | | | | | | | | |
|---|---|---|---|---|---|---|---|---|---|---|---|---|---|---|---|
| Ala | Pro | Thr | Ser | Ser | Thr | Lys | Lys | Thr | Gln | Leu | Gln | Leu | Glu | Glu | |
| 1 | | | | 5 | | | | | 10 | | | | | 15 | |
| Leu | Ile | Leu | Asp | Leu | Gln | Met | Ile | Leu | Asn | Gly | Ile | Asn | Asn | Tyr | Lys |
| | | | 20 | | | | | 25 | | | | | 30 | | |
| Asn | Pro | Lys | Leu | Thr | Arg | Met | Leu | Thr | Phe | Lys | Phe | Tyr | Met | Pro | Lys |
| | | | 35 | | | | | 40 | | | | | 45 | | |
| Lys | Ala | Thr | Glu | Leu | Lys | His | Leu | Gln | Cys | Leu | Glu | Glu | Glu | Leu | Lys |
| | 50 | | | | | 55 | | | | | 60 | | | | |
| Pro | Leu | Glu | Glu | Val | Leu | Asn | Leu | Ala | Gln | Ser | Lys | Asn | Phe | His | Leu |
| 65 | | | | | 70 | | | | | 75 | | | | | 80 |
| Arg | Pro | Arg | Asp | Leu | Ile | Ser | Asn | Leu | Asn | Val | Ile | Leu | Glu | Leu | |
| | | | | 85 | | | | | 90 | | | | | 95 | |
| Lys | Gly | Ser | Glu | Thr | Thr | Phe | Met | Cys | Glu | Tyr | Ala | Asp | Glu | Thr | Ala |
| | | | | 100 | | | | | 105 | | | | | 110 | |
| Thr | Ile | Val | Glu | Phe | Leu | Asn | Arg | Trp | Ile | Thr | Phe | Ala | Gln | Ser | Ile |
| | | | 115 | | | | | 120 | | | | | 125 | | |
| Ile | Ser | Thr | Leu | Thr | Gly | Gly | Gly | Gly | Ser | Gly | Gly | Gly | Ser | Gly | |
| | 130 | | | | | 135 | | | | | 140 | | | | |
| Gly | Gly | Gly | Ser | Glu | Pro | Lys | Ser | Ser | Asp | Lys | Thr | His | Thr | Cys | Pro |
| 145 | | | | | 150 | | | | | 155 | | | | | 160 |
| Pro | Cys | Pro | Ala | Pro | Glu | Leu | Leu | Gly | Gly | Pro | Ser | Val | Phe | Leu | Phe |
| | | | | 165 | | | | | 170 | | | | | 175 | |
| Pro | Pro | Lys | Pro | Lys | Asp | Thr | Leu | Met | Ile | Ser | Arg | Thr | Pro | Glu | Val |
| | | | 180 | | | | | 185 | | | | | 190 | | |
| Thr | Cys | Val | Val | Val | Asp | Val | Ser | His | Glu | Asp | Pro | Glu | Val | Lys | Phe |
| | | 195 | | | | | 200 | | | | | 205 | | | |
| Asn | Trp | Tyr | Val | Asp | Gly | Val | Glu | Val | His | Asn | Ala | Lys | Thr | Lys | Pro |
| | 210 | | | | | 215 | | | | | 220 | | | | |
| Arg | Glu | Glu | Gln | Tyr | Gly | Ser | Thr | Tyr | Arg | Val | Val | Ser | Val | Leu | Thr |
| 225 | | | | | 230 | | | | | 235 | | | | | 240 |
| Val | Leu | His | Gln | Asp | Trp | Leu | Asn | Gly | Lys | Glu | Tyr | Lys | Cys | Lys | Val |
| | | | | 245 | | | | | 250 | | | | | 255 | |
| Ser | Asn | Lys | Ala | Leu | Pro | Ala | Pro | Ile | Glu | Lys | Thr | Ile | Ser | Lys | Ala |
| | | | 260 | | | | | 265 | | | | | 270 | | |
| Lys | Gly | Gln | Pro | Arg | Glu | Pro | Gln | Val | Tyr | Thr | Leu | Pro | Pro | Ser | Arg |
| | | | 275 | | | | | 280 | | | | | 285 | | |
| Asp | Glu | Leu | Thr | Lys | Asn | Gln | Val | Ser | Leu | Thr | Cys | Leu | Val | Lys | Gly |
| | | 290 | | | | | 295 | | | | | 300 | | | |
| Phe | Tyr | Pro | Ser | Asp | Ile | Ala | Val | Glu | Trp | Glu | Ser | Asn | Gly | Gln | Pro |
| 305 | | | | | 310 | | | | | 315 | | | | | 320 |
| Glu | Asn | Asn | Tyr | Lys | Thr | Thr | Pro | Pro | Val | Leu | Asp | Ser | Asp | Gly | Ser |
| | | | | 325 | | | | | 330 | | | | | 335 | |
| Phe | Phe | Leu | Tyr | Ser | Lys | Leu | Thr | Val | Asp | Lys | Ser | Arg | Trp | Gln | Gln |
| | | | 340 | | | | | 345 | | | | | 350 | | |
| Gly | Asn | Val | Phe | Ser | Cys | Ser | Val | Met | His | Glu | Ala | Leu | His | Asn | His |
| | | | 355 | | | | | 360 | | | | | 365 | | |

```
Tyr Thr Gln Lys Ser Leu Ser Leu Ser Pro Gly Lys
        370                 375             380
```

<210> SEQ ID NO 44
<211> LENGTH: 380
<212> TYPE: PRT
<213> ORGANISM: Artificial Sequence
<220> FEATURE:
<223> OTHER INFORMATION: synthetic polypeptide

<400> SEQUENCE: 44

```
Ala Pro Thr Ser Ser Thr Lys Lys Thr Gln Leu Gln Leu Glu Glu
1               5                   10                  15

Leu Leu Leu Asp Leu Gln Met Ile Leu Asn Trp Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Phe Trp Ile Thr Phe Ala Gln Ser Ile
        115                 120                 125

Ile Ser Thr Leu Thr Gly Gly Gly Ser Gly Gly Gly Ser Gly
130                 135                 140

Gly Gly Ser Glu Pro Lys Ser Ser Asp Lys Thr His Thr Cys Pro
145                 150                 155                 160

Pro Cys Pro Ala Pro Glu Leu Leu Gly Gly Pro Ser Val Phe Leu Phe
                165                 170                 175

Pro Pro Lys Pro Lys Asp Thr Leu Met Ile Ser Arg Thr Pro Glu Val
            180                 185                 190

Thr Cys Val Val Val Asp Val Ser His Glu Asp Pro Glu Val Lys Phe
        195                 200                 205

Asn Trp Tyr Val Asp Gly Val Glu Val His Asn Ala Lys Thr Lys Pro
    210                 215                 220

Arg Glu Glu Gln Tyr Gly Ser Thr Tyr Arg Val Val Ser Val Leu Thr
225                 230                 235                 240

Val Leu His Gln Asp Trp Leu Asn Gly Lys Glu Tyr Lys Cys Lys Val
                245                 250                 255

Ser Asn Lys Ala Leu Pro Ala Pro Ile Glu Lys Thr Ile Ser Lys Ala
            260                 265                 270

Lys Gly Gln Pro Arg Glu Pro Gln Val Tyr Thr Leu Pro Pro Ser Arg
        275                 280                 285

Asp Glu Leu Thr Lys Asn Gln Val Ser Leu Thr Cys Leu Val Lys Gly
    290                 295                 300

Phe Tyr Pro Ser Asp Ile Ala Val Glu Trp Glu Ser Asn Gly Gln Pro
305                 310                 315                 320

Glu Asn Asn Tyr Lys Thr Thr Pro Pro Val Leu Asp Ser Asp Gly Ser
                325                 330                 335

Phe Phe Leu Tyr Ser Lys Leu Thr Val Asp Lys Ser Arg Trp Gln Gln
            340                 345                 350
```

```
Gly Asn Val Phe Ser Cys Ser Val Met His Glu Ala Leu His Asn His
            355                 360                 365

Tyr Thr Gln Lys Ser Leu Ser Leu Ser Pro Gly Lys
            370                 375                 380

<210> SEQ ID NO 45
<211> LENGTH: 380
<212> TYPE: PRT
<213> ORGANISM: Artificial Sequence
<220> FEATURE:
<223> OTHER INFORMATION: synthetic polypeptide

<400> SEQUENCE: 45

Ala Pro Thr Ser Ser Ser Thr Lys Lys Thr Gln Leu Gln Leu Glu Glu
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Leu Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Phe Trp Ile Thr Phe Ala Gln Ser Ile
        115                 120                 125

Ile Ser Thr Leu Thr Gly Gly Gly Gly Ser Gly Gly Gly Ser Gly
                135                 140

Gly Gly Gly Ser Glu Pro Lys Ser Ser Asp Lys Thr His Thr Cys Pro
145                 150                 155                 160

Pro Cys Pro Ala Pro Glu Leu Leu Gly Gly Pro Ser Val Phe Leu Phe
                165                 170                 175

Pro Pro Lys Pro Lys Asp Thr Leu Met Ile Ser Arg Thr Pro Glu Val
            180                 185                 190

Thr Cys Val Val Val Asp Val Ser His Glu Asp Pro Glu Val Lys Phe
        195                 200                 205

Asn Trp Tyr Val Asp Gly Val Glu Val His Asn Ala Lys Thr Lys Pro
    210                 215                 220

Arg Glu Glu Gln Tyr Gly Ser Thr Tyr Arg Val Val Ser Val Leu Thr
225                 230                 235                 240

Val Leu His Gln Asp Trp Leu Asn Gly Lys Glu Tyr Lys Cys Lys Val
                245                 250                 255

Ser Asn Lys Ala Leu Pro Ala Pro Ile Glu Lys Thr Ile Ser Lys Ala
            260                 265                 270

Lys Gly Gln Pro Arg Glu Pro Gln Val Tyr Thr Leu Pro Pro Ser Arg
        275                 280                 285

Asp Glu Leu Thr Lys Asn Gln Val Ser Leu Thr Cys Leu Val Lys Gly
    290                 295                 300

Phe Tyr Pro Ser Asp Ile Ala Val Glu Trp Glu Ser Asn Gly Gln Pro
305                 310                 315                 320

Glu Asn Asn Tyr Lys Thr Thr Pro Pro Val Leu Asp Ser Asp Gly Ser
                325                 330                 335
```

```
Phe Phe Leu Tyr Ser Lys Leu Thr Val Asp Lys Ser Arg Trp Gln Gln
                340                 345                 350

Gly Asn Val Phe Ser Cys Ser Val Met His Glu Ala Leu His Asn His
            355                 360                 365

Tyr Thr Gln Lys Ser Leu Ser Leu Ser Pro Gly Lys
    370                 375                 380

<210> SEQ ID NO 46
<211> LENGTH: 380
<212> TYPE: PRT
<213> ORGANISM: Artificial Sequence
<220> FEATURE:
<223> OTHER INFORMATION: synthetic polypeptide

<400> SEQUENCE: 46

Ala Pro Thr Ser Ser Ser Thr Lys Lys Thr Gln Leu Gln Leu Glu His
1               5                   10                  15

Leu Leu Leu Ala Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr Gly Gly Gly Gly Ser Gly Gly Gly Ser Gly
130                 135                 140

Gly Gly Gly Ser Glu Pro Lys Ser Ser Asp Lys Thr His Thr Cys Pro
145                 150                 155                 160

Pro Cys Pro Ala Pro Glu Leu Leu Gly Gly Pro Ser Val Phe Leu Phe
                165                 170                 175

Pro Pro Lys Pro Lys Asp Thr Leu Met Ile Ser Arg Thr Pro Glu Val
            180                 185                 190

Thr Cys Val Val Val Asp Val Ser His Glu Asp Pro Glu Val Lys Phe
        195                 200                 205

Asn Trp Tyr Val Asp Gly Val Glu Val His Asn Ala Lys Thr Lys Pro
    210                 215                 220

Arg Glu Glu Gln Tyr Gly Ser Thr Tyr Arg Val Val Ser Val Leu Thr
225                 230                 235                 240

Val Leu His Gln Asp Trp Leu Asn Gly Lys Glu Tyr Lys Cys Lys Val
                245                 250                 255

Ser Asn Lys Ala Leu Pro Ala Pro Ile Glu Lys Thr Ile Ser Lys Ala
            260                 265                 270

Lys Gly Gln Pro Arg Glu Pro Gln Val Tyr Thr Leu Pro Pro Ser Arg
        275                 280                 285

Asp Glu Leu Thr Lys Asn Gln Val Ser Leu Thr Cys Leu Val Lys Gly
    290                 295                 300

Phe Tyr Pro Ser Asp Ile Ala Val Glu Trp Glu Ser Asn Gly Gln Pro
305                 310                 315                 320
```

```
Glu Asn Asn Tyr Lys Thr Thr Pro Val Leu Asp Ser Asp Gly Ser
            325                 330                 335

Phe Phe Leu Tyr Ser Lys Leu Thr Val Asp Lys Ser Arg Trp Gln Gln
        340                 345                 350

Gly Asn Val Phe Ser Cys Ser Val Met His Glu Ala Leu His Asn His
            355                 360                 365

Tyr Thr Gln Lys Ser Leu Ser Leu Ser Pro Gly Lys
        370                 375                 380

<210> SEQ ID NO 47
<211> LENGTH: 380
<212> TYPE: PRT
<213> ORGANISM: Artificial Sequence
<220> FEATURE:
<223> OTHER INFORMATION: synthetic polypeptide

<400> SEQUENCE: 47

Ala Pro Thr Ser Ser Ser Thr Lys Lys Thr Gln Leu Gln Leu Glu His
1               5                   10                  15

Leu Leu Leu Ala Leu Gln Met Ile Leu Asn Gly Ile Asn Asn Val Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Leu Gln Ser Lys Asn Phe Gln Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr Gly Gly Gly Gly Ser Gly Gly Gly Gly Ser Gly
    130                 135                 140

Gly Gly Gly Ser Glu Pro Lys Ser Ser Asp Lys Thr His Thr Cys Pro
145                 150                 155                 160

Pro Cys Pro Ala Pro Glu Leu Leu Gly Gly Pro Ser Val Phe Leu Phe
                165                 170                 175

Pro Pro Lys Pro Lys Asp Thr Leu Met Ile Ser Arg Thr Pro Glu Val
            180                 185                 190

Thr Cys Val Val Val Asp Val Ser His Glu Asp Pro Glu Val Lys Phe
        195                 200                 205

Asn Trp Tyr Val Asp Gly Val Glu Val His Asn Ala Lys Thr Lys Pro
    210                 215                 220

Arg Glu Glu Gln Tyr Gly Ser Thr Tyr Arg Val Val Ser Val Leu Thr
225                 230                 235                 240

Val Leu His Gln Asp Trp Leu Asn Gly Lys Glu Tyr Lys Cys Lys Val
                245                 250                 255

Ser Asn Lys Ala Leu Pro Ala Pro Ile Glu Lys Thr Ile Ser Lys Ala
            260                 265                 270

Lys Gly Gln Pro Arg Glu Pro Gln Val Tyr Thr Leu Pro Pro Ser Arg
        275                 280                 285

Asp Glu Leu Thr Lys Asn Gln Val Ser Leu Thr Cys Leu Val Lys Gly
    290                 295                 300
```

-continued

```
Phe Tyr Pro Ser Asp Ile Ala Val Glu Trp Glu Ser Asn Gly Gln Pro
305                 310                 315                 320

Glu Asn Asn Tyr Lys Thr Thr Pro Pro Val Leu Asp Ser Asp Gly Ser
                325                 330                 335

Phe Phe Leu Tyr Ser Lys Leu Thr Val Asp Lys Ser Arg Trp Gln Gln
                340                 345                 350

Gly Asn Val Phe Ser Cys Ser Val Met His Glu Ala Leu His Asn His
                355                 360                 365

Tyr Thr Gln Lys Ser Leu Ser Leu Ser Pro Gly Lys
                370                 375                 380

<210> SEQ ID NO 48
<211> LENGTH: 380
<212> TYPE: PRT
<213> ORGANISM: Artificial Sequence
<220> FEATURE:
<223> OTHER INFORMATION: synthetic polypeptide

<400> SEQUENCE: 48

Ala Pro Thr Ser Ser Thr Lys Lys Thr Gln Leu Gln Leu Glu His
1               5                   10                  15

Leu Leu Leu Ala Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
                35                  40                  45

Lys Ala Thr Glu Leu Lys His Leu Gln Cys Leu Glu Glu Glu Leu Lys
                50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Phe Trp Ile Thr Phe Ala Gln Ser Ile
                115                 120                 125

Ile Ser Thr Leu Thr Gly Gly Gly Gly Ser Gly Gly Gly Gly Ser Gly
                130                 135                 140

Gly Gly Ser Glu Pro Lys Ser Ser Asp Lys Thr His Thr Cys Pro
145                 150                 155                 160

Pro Cys Pro Ala Pro Glu Leu Leu Gly Gly Pro Ser Val Phe Leu Phe
                165                 170                 175

Pro Pro Lys Pro Lys Asp Thr Leu Met Ile Ser Arg Thr Pro Glu Val
                180                 185                 190

Thr Cys Val Val Val Asp Val Ser His Glu Asp Pro Glu Val Lys Phe
                195                 200                 205

Asn Trp Tyr Val Asp Gly Val Glu Val His Asn Ala Lys Thr Lys Pro
                210                 215                 220

Arg Glu Glu Gln Tyr Gly Ser Thr Tyr Arg Val Val Ser Val Leu Thr
225                 230                 235                 240

Val Leu His Gln Asp Trp Leu Asn Gly Lys Glu Tyr Lys Cys Lys Val
                245                 250                 255

Ser Asn Lys Ala Leu Pro Ala Pro Ile Glu Lys Thr Ile Ser Lys Ala
                260                 265                 270

Lys Gly Gln Pro Arg Glu Pro Gln Val Tyr Thr Leu Pro Pro Ser Arg
                275                 280                 285
```

```
Asp Glu Leu Thr Lys Asn Gln Val Ser Leu Thr Cys Leu Val Lys Gly
        290                 295                 300

Phe Tyr Pro Ser Asp Ile Ala Val Glu Trp Glu Ser Asn Gly Gln Pro
305                 310                 315                 320

Glu Asn Asn Tyr Lys Thr Thr Pro Pro Val Leu Asp Ser Asp Gly Ser
                325                 330                 335

Phe Phe Leu Tyr Ser Lys Leu Thr Val Asp Lys Ser Arg Trp Gln Gln
            340                 345                 350

Gly Asn Val Phe Ser Cys Ser Val Met His Glu Ala Leu His Asn His
        355                 360                 365

Tyr Thr Gln Lys Ser Leu Ser Leu Ser Pro Gly Lys
    370                 375                 380

<210> SEQ ID NO 49
<211> LENGTH: 380
<212> TYPE: PRT
<213> ORGANISM: Artificial Sequence
<220> FEATURE:
<223> OTHER INFORMATION: synthetic polypeptide

<400> SEQUENCE: 49

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Arg Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr Gly Gly Gly Gly Ser Gly Gly Gly Ser Gly
130                 135                 140

Gly Gly Gly Ser Glu Pro Lys Ser Ser Asp Lys Thr His Thr Cys Pro
145                 150                 155                 160

Pro Cys Pro Ala Pro Glu Leu Leu Gly Gly Pro Ser Val Phe Leu Phe
                165                 170                 175

Pro Pro Lys Pro Lys Asp Thr Leu Met Ile Ser Arg Thr Pro Glu Val
            180                 185                 190

Thr Cys Val Val Val Asp Val Ser His Glu Asp Pro Glu Val Lys Phe
        195                 200                 205

Asn Trp Tyr Val Asp Gly Val Glu Val His Asn Ala Lys Thr Lys Pro
210                 215                 220

Arg Glu Glu Gln Tyr Gly Ser Thr Tyr Arg Val Val Ser Val Leu Thr
225                 230                 235                 240

Val Leu His Gln Asp Trp Leu Asn Gly Lys Glu Tyr Lys Cys Lys Val
                245                 250                 255

Ser Asn Lys Ala Leu Pro Ala Pro Ile Glu Lys Thr Ile Ser Lys Ala
            260                 265                 270
```

```
Lys Gly Gln Pro Arg Glu Pro Gln Val Tyr Thr Leu Pro Ser Arg
            275                 280                 285

Asp Glu Leu Thr Lys Asn Gln Val Ser Leu Thr Cys Leu Val Lys Gly
        290                 295                 300

Phe Tyr Pro Ser Asp Ile Ala Val Glu Trp Glu Ser Asn Gly Gln Pro
305                 310                 315                 320

Glu Asn Asn Tyr Lys Thr Thr Pro Pro Val Leu Asp Ser Asp Gly Ser
                325                 330                 335

Phe Phe Leu Tyr Ser Lys Leu Thr Val Asp Lys Ser Arg Trp Gln Gln
            340                 345                 350

Gly Asn Val Phe Ser Cys Ser Val Met His Glu Ala Leu His Asn His
        355                 360                 365

Tyr Thr Gln Lys Ser Leu Ser Leu Ser Pro Gly Lys
        370                 375                 380

<210> SEQ ID NO 50
<211> LENGTH: 380
<212> TYPE: PRT
<213> ORGANISM: Artificial Sequence
<220> FEATURE:
<223> OTHER INFORMATION: synthetic polypeptide

<400> SEQUENCE: 50

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Val Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Leu Gln Ser Lys Asn Phe Gln Leu
65                  70                  75                  80

Arg Pro Arg Asp Leu Ile Ser Asn Ile Asn Arg Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr Gly Gly Gly Gly Ser Gly Gly Gly Gly Ser Gly
130                 135                 140

Gly Gly Gly Ser Glu Pro Lys Ser Ser Asp Lys Thr His Thr Cys Pro
145                 150                 155                 160

Pro Cys Pro Ala Pro Glu Leu Leu Gly Gly Pro Ser Val Phe Leu Phe
                165                 170                 175

Pro Pro Lys Pro Lys Asp Thr Leu Met Ile Ser Arg Thr Pro Glu Val
            180                 185                 190

Thr Cys Val Val Val Asp Val Ser His Glu Asp Pro Glu Val Lys Phe
        195                 200                 205

Asn Trp Tyr Val Asp Gly Val Glu Val His Asn Ala Lys Thr Lys Pro
    210                 215                 220

Arg Glu Glu Gln Tyr Gly Ser Thr Tyr Arg Val Val Ser Val Leu Thr
225                 230                 235                 240

Val Leu His Gln Asp Trp Leu Asn Gly Lys Glu Tyr Lys Cys Lys Val
                245                 250                 255
```

```
Ser Asn Lys Ala Leu Pro Ala Pro Ile Glu Lys Thr Ile Ser Lys Ala
                260                 265                 270

Lys Gly Gln Pro Arg Glu Pro Gln Val Tyr Thr Leu Pro Pro Ser Arg
            275                 280                 285

Asp Glu Leu Thr Lys Asn Gln Val Ser Leu Thr Cys Leu Val Lys Gly
        290                 295                 300

Phe Tyr Pro Ser Asp Ile Ala Val Glu Trp Glu Ser Asn Gly Gln Pro
305                 310                 315                 320

Glu Asn Asn Tyr Lys Thr Thr Pro Pro Val Leu Asp Ser Asp Gly Ser
                325                 330                 335

Phe Phe Leu Tyr Ser Lys Leu Thr Val Asp Lys Ser Arg Trp Gln Gln
            340                 345                 350

Gly Asn Val Phe Ser Cys Ser Val Met His Glu Ala Leu His Asn His
        355                 360                 365

Tyr Thr Gln Lys Ser Leu Ser Leu Ser Pro Gly Lys
                370                 375                 380

<210> SEQ ID NO 51
<211> LENGTH: 380
<212> TYPE: PRT
<213> ORGANISM: Artificial Sequence
<220> FEATURE:
<223> OTHER INFORMATION: synthetic polypeptide

<400> SEQUENCE: 51

Ala Pro Thr Ser Ser Thr Lys Lys Thr Gln Leu Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Arg Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr Gly Gly Gly Gly Ser Gly Gly Gly Ser Gly
130                 135                 140

Gly Gly Gly Ser Glu Pro Lys Ser Ser Asp Lys Thr His Thr Cys Pro
145                 150                 155                 160

Pro Cys Pro Ala Pro Glu Leu Leu Gly Gly Pro Ser Val Phe Leu Phe
                165                 170                 175

Pro Pro Lys Pro Lys Asp Thr Leu Met Ile Ser Arg Thr Pro Glu Val
            180                 185                 190

Thr Cys Val Val Val Asp Val Ser His Glu Asp Pro Glu Val Lys Phe
        195                 200                 205

Asn Trp Tyr Val Asp Gly Val Glu Val His Asn Ala Lys Thr Lys Pro
            210                 215                 220

Arg Glu Glu Gln Tyr Gly Ser Thr Tyr Arg Val Val Ser Val Leu Thr
225                 230                 235                 240
```

```
Val Leu His Gln Asp Trp Leu Asn Gly Lys Glu Tyr Lys Cys Lys Val
                245                 250                 255

Ser Asn Lys Ala Leu Pro Ala Pro Ile Glu Lys Thr Ile Ser Lys Ala
            260                 265                 270

Lys Gly Gln Pro Arg Glu Pro Gln Val Tyr Thr Leu Pro Pro Ser Arg
            275                 280                 285

Asp Glu Leu Thr Lys Asn Gln Val Ser Leu Thr Cys Leu Val Lys Gly
            290                 295                 300

Phe Tyr Pro Ser Asp Ile Ala Val Glu Trp Glu Ser Asn Gly Gln Pro
305                 310                 315                 320

Glu Asn Asn Tyr Lys Thr Thr Pro Pro Val Leu Asp Ser Asp Gly Ser
            325                 330                 335

Phe Phe Leu Tyr Ser Lys Leu Thr Val Asp Lys Ser Arg Trp Gln Gln
            340                 345                 350

Gly Asn Val Phe Ser Cys Ser Val Met His Glu Ala Leu His Asn His
            355                 360                 365

Tyr Thr Gln Lys Ser Leu Ser Leu Ser Pro Gly Lys
            370                 375                 380

<210> SEQ ID NO 52
<211> LENGTH: 380
<212> TYPE: PRT
<213> ORGANISM: Artificial Sequence
<220> FEATURE:
<223> OTHER INFORMATION: synthetic polypeptide

<400> SEQUENCE: 52

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Arg Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Phe Trp Ile Thr Phe Ala Gln Ser Ile
        115                 120                 125

Ile Ser Thr Leu Thr Gly Gly Gly Gly Ser Gly Gly Gly Gly Ser Gly
130                 135                 140

Gly Gly Ser Glu Pro Lys Ser Ser Asp Lys Thr His Thr Cys Pro
145                 150                 155                 160

Pro Cys Pro Ala Pro Glu Leu Leu Gly Gly Pro Ser Val Phe Leu Phe
                165                 170                 175

Pro Pro Lys Pro Lys Asp Thr Leu Met Ile Ser Arg Thr Pro Glu Val
            180                 185                 190

Thr Cys Val Val Val Asp Val Ser His Glu Asp Pro Glu Val Lys Phe
        195                 200                 205

Asn Trp Tyr Val Asp Gly Val Glu Val His Asn Ala Lys Thr Lys Pro
210                 215                 220
```

Arg Glu Glu Gln Tyr Gly Ser Thr Tyr Arg Val Ser Val Leu Thr
225                 230                 235                 240

Val Leu His Gln Asp Trp Leu Asn Gly Lys Glu Tyr Lys Cys Lys Val
            245                 250                 255

Ser Asn Lys Ala Leu Pro Ala Pro Ile Glu Lys Thr Ile Ser Lys Ala
        260                 265                 270

Lys Gly Gln Pro Arg Glu Pro Gln Val Tyr Thr Leu Pro Pro Ser Arg
    275                 280                 285

Asp Glu Leu Thr Lys Asn Gln Val Ser Leu Thr Cys Leu Val Lys Gly
290                 295                 300

Phe Tyr Pro Ser Asp Ile Ala Val Glu Trp Glu Ser Asn Gly Gln Pro
305                 310                 315                 320

Glu Asn Asn Tyr Lys Thr Thr Pro Pro Val Leu Asp Ser Asp Gly Ser
                325                 330                 335

Phe Phe Leu Tyr Ser Lys Leu Thr Val Asp Lys Ser Arg Trp Gln Gln
                340                 345                 350

Gly Asn Val Phe Ser Cys Ser Val Met His Glu Ala Leu His Asn His
            355                 360                 365

Tyr Thr Gln Lys Ser Leu Ser Leu Ser Pro Gly Lys
370                 375                 380

<210> SEQ ID NO 53
<211> LENGTH: 380
<212> TYPE: PRT
<213> ORGANISM: Artificial Sequence
<220> FEATURE:
<223> OTHER INFORMATION: synthetic polypeptide

<400> SEQUENCE: 53

Ala Pro Thr Ser Ser Ser Thr Lys Lys Thr Gln Leu Gln Leu Glu His
1               5                   10                  15

Leu Ile Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Leu Asn Arg Ile Ile Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr Gly Gly Gly Gly Ser Gly Gly Gly Gly Ser Gly
130                 135                 140

Gly Gly Gly Ser Glu Pro Lys Ser Ser Asp Lys Thr His Thr Cys Pro
145                 150                 155                 160

Pro Cys Pro Ala Pro Glu Leu Leu Gly Gly Pro Ser Val Phe Leu Phe
                165                 170                 175

Pro Pro Lys Pro Lys Asp Thr Leu Met Ile Ser Arg Thr Pro Glu Val
            180                 185                 190

Thr Cys Val Val Val Asp Val Ser His Glu Asp Pro Glu Val Lys Phe
        195                 200                 205

```
Asn Trp Tyr Val Asp Gly Val Glu Val His Asn Ala Lys Thr Lys Pro
    210                 215                 220

Arg Glu Glu Gln Tyr Gly Ser Thr Tyr Arg Val Val Ser Val Leu Thr
225                 230                 235                 240

Val Leu His Gln Asp Trp Leu Asn Gly Lys Glu Tyr Lys Cys Lys Val
                245                 250                 255

Ser Asn Lys Ala Leu Pro Ala Pro Ile Glu Lys Thr Ile Ser Lys Ala
            260                 265                 270

Lys Gly Gln Pro Arg Glu Pro Gln Val Tyr Thr Leu Pro Pro Ser Arg
        275                 280                 285

Asp Glu Leu Thr Lys Asn Gln Val Ser Leu Thr Cys Leu Val Lys Gly
    290                 295                 300

Phe Tyr Pro Ser Asp Ile Ala Val Glu Trp Glu Ser Asn Gly Gln Pro
305                 310                 315                 320

Glu Asn Asn Tyr Lys Thr Thr Pro Pro Val Leu Asp Ser Asp Gly Ser
                325                 330                 335

Phe Phe Leu Tyr Ser Lys Leu Thr Val Asp Lys Ser Arg Trp Gln Gln
            340                 345                 350

Gly Asn Val Phe Ser Cys Ser Val Met His Glu Ala Leu His Asn His
        355                 360                 365

Tyr Thr Gln Lys Ser Leu Ser Leu Ser Pro Gly Lys
    370                 375                 380

<210> SEQ ID NO 54
<211> LENGTH: 380
<212> TYPE: PRT
<213> ORGANISM: Artificial Sequence
<220> FEATURE:
<223> OTHER INFORMATION: synthetic polypeptide

<400> SEQUENCE: 54

Ala Pro Thr Ser Ser Ser Thr Lys Lys Thr Gln Leu Gln Leu Glu Glu
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Arg Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr Gly Gly Gly Gly Ser Gly Gly Gly Gly Ser Gly
130                 135                 140

Gly Gly Gly Ser Glu Pro Lys Ser Ser Asp Lys Thr His Thr Cys Pro
145                 150                 155                 160

Pro Cys Pro Ala Pro Glu Leu Leu Gly Gly Pro Ser Val Phe Leu Phe
                165                 170                 175

Pro Pro Lys Pro Lys Asp Thr Leu Met Ile Ser Arg Thr Pro Glu Val
            180                 185                 190
```

Thr Cys Val Val Asp Val Ser His Glu Asp Pro Glu Val Lys Phe
            195                 200                 205

Asn Trp Tyr Val Asp Gly Val Glu Val His Asn Ala Lys Thr Lys Pro
210                 215                 220

Arg Glu Glu Gln Tyr Gly Ser Thr Tyr Arg Val Val Ser Val Leu Thr
225                 230                 235                 240

Val Leu His Gln Asp Trp Leu Asn Gly Lys Glu Tyr Lys Cys Lys Val
            245                 250                 255

Ser Asn Lys Ala Leu Pro Ala Pro Ile Glu Lys Thr Ile Ser Lys Ala
            260                 265                 270

Lys Gly Gln Pro Arg Glu Pro Gln Val Tyr Thr Leu Pro Pro Ser Arg
            275                 280                 285

Asp Glu Leu Thr Lys Asn Gln Val Ser Leu Thr Cys Leu Val Lys Gly
            290                 295                 300

Phe Tyr Pro Ser Asp Ile Ala Val Glu Trp Glu Ser Asn Gly Gln Pro
305                 310                 315                 320

Glu Asn Asn Tyr Lys Thr Thr Pro Pro Val Leu Asp Ser Asp Gly Ser
            325                 330                 335

Phe Phe Leu Tyr Ser Lys Leu Thr Val Asp Lys Ser Arg Trp Gln Gln
            340                 345                 350

Gly Asn Val Phe Ser Cys Ser Val Met His Glu Ala Leu His Asn His
            355                 360                 365

Tyr Thr Gln Lys Ser Leu Ser Leu Ser Pro Gly Lys
            370                 375                 380

<210> SEQ ID NO 55
<211> LENGTH: 380
<212> TYPE: PRT
<213> ORGANISM: Artificial Sequence
<220> FEATURE:
<223> OTHER INFORMATION: synthetic polypeptide

<400> SEQUENCE: 55

Ala Pro Thr Ser Ser Thr Lys Lys Thr Gln Leu Gln Leu Glu Glu
1               5                   10                  15

Leu Leu Leu Asp Leu Gln Met Ile Leu Asn Gly Ile Asn Asn Val Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
            50                  55                  60

Pro Leu Glu Glu Val Leu Asn Leu Leu Gln Ser Lys Asn Phe Gln Leu
65                  70                  75                  80

Arg Pro Arg Asp Leu Ile Ser Asn Ile Asn Arg Ile Val Leu Glu Leu
            85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
            115                 120                 125

Ile Ser Thr Leu Thr Gly Gly Gly Gly Ser Gly Gly Gly Ser Gly
            130                 135                 140

Gly Gly Gly Ser Glu Pro Lys Ser Ser Asp Lys Thr His Thr Cys Pro
145                 150                 155                 160

Pro Cys Pro Ala Pro Glu Leu Leu Gly Gly Pro Ser Val Phe Leu Phe
            165                 170                 175

```
Pro Pro Lys Pro Lys Asp Thr Leu Met Ile Ser Arg Thr Pro Glu Val
            180                 185                 190

Thr Cys Val Val Val Asp Val Ser His Glu Asp Pro Glu Val Lys Phe
        195                 200                 205

Asn Trp Tyr Val Asp Gly Val Glu Val His Asn Ala Lys Thr Lys Pro
        210                 215                 220

Arg Glu Glu Gln Tyr Gly Ser Thr Tyr Arg Val Val Ser Val Leu Thr
225                 230                 235                 240

Val Leu His Gln Asp Trp Leu Asn Gly Lys Glu Tyr Lys Cys Lys Val
            245                 250                 255

Ser Asn Lys Ala Leu Pro Ala Pro Ile Glu Lys Thr Ile Ser Lys Ala
            260                 265                 270

Lys Gly Gln Pro Arg Glu Pro Gln Val Tyr Thr Leu Pro Pro Ser Arg
            275                 280                 285

Asp Glu Leu Thr Lys Asn Gln Val Ser Leu Thr Cys Leu Val Lys Gly
            290                 295                 300

Phe Tyr Pro Ser Asp Ile Ala Val Glu Trp Glu Ser Asn Gly Gln Pro
305                 310                 315                 320

Glu Asn Asn Tyr Lys Thr Thr Pro Pro Val Leu Asp Ser Asp Gly Ser
                325                 330                 335

Phe Phe Leu Tyr Ser Lys Leu Thr Val Asp Lys Ser Arg Trp Gln Gln
                340                 345                 350

Gly Asn Val Phe Ser Cys Ser Val Met His Glu Ala Leu His Asn His
            355                 360                 365

Tyr Thr Gln Lys Ser Leu Ser Leu Ser Pro Gly Lys
            370                 375                 380

<210> SEQ ID NO 56
<211> LENGTH: 380
<212> TYPE: PRT
<213> ORGANISM: Artificial Sequence
<220> FEATURE:
<223> OTHER INFORMATION: synthetic polypeptide

<400> SEQUENCE: 56

Ala Pro Thr Ser Ser Thr Lys Lys Thr Gln Leu Gln Leu Glu Glu
1               5                   10                  15

Leu Ile Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Leu Asn Arg Ile Ile Leu Glu Leu
            85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr Gly Gly Gly Ser Gly Gly Gly Ser Gly
        130                 135                 140

Gly Gly Gly Ser Glu Pro Lys Ser Ser Asp Lys Thr His Thr Cys Pro
145                 150                 155                 160
```

Pro Cys Pro Ala Pro Glu Leu Leu Gly Gly Pro Ser Val Phe Leu Phe
                165                 170                 175

Pro Pro Lys Pro Lys Asp Thr Leu Met Ile Ser Arg Thr Pro Glu Val
            180                 185                 190

Thr Cys Val Val Val Asp Val Ser His Glu Asp Pro Glu Val Lys Phe
            195                 200                 205

Asn Trp Tyr Val Asp Gly Val Glu Val His Asn Ala Lys Thr Lys Pro
        210                 215                 220

Arg Glu Glu Gln Tyr Gly Ser Thr Tyr Arg Val Val Ser Val Leu Thr
225                 230                 235                 240

Val Leu His Gln Asp Trp Leu Asn Gly Lys Glu Tyr Lys Cys Lys Val
                245                 250                 255

Ser Asn Lys Ala Leu Pro Ala Pro Ile Glu Lys Thr Ile Ser Lys Ala
            260                 265                 270

Lys Gly Gln Pro Arg Glu Pro Gln Val Tyr Thr Leu Pro Pro Ser Arg
            275                 280                 285

Asp Glu Leu Thr Lys Asn Gln Val Ser Leu Thr Cys Leu Val Lys Gly
        290                 295                 300

Phe Tyr Pro Ser Asp Ile Ala Val Glu Trp Glu Ser Asn Gly Gln Pro
305                 310                 315                 320

Glu Asn Asn Tyr Lys Thr Thr Pro Pro Val Leu Asp Ser Asp Gly Ser
                325                 330                 335

Phe Phe Leu Tyr Ser Lys Leu Thr Val Asp Lys Ser Arg Trp Gln Gln
            340                 345                 350

Gly Asn Val Phe Ser Cys Ser Val Met His Glu Ala Leu His Asn His
        355                 360                 365

Tyr Thr Gln Lys Ser Leu Ser Leu Ser Pro Gly Lys
370                 375                 380

<210> SEQ ID NO 57
<211> LENGTH: 272
<212> TYPE: PRT
<213> ORGANISM: Homo sapiens

<400> SEQUENCE: 57

Met Asp Ser Tyr Leu Leu Met Trp Gly Leu Leu Thr Phe Ile Met Val
1               5                   10                  15

Pro Gly Cys Gln Ala Glu Leu Cys Asp Asp Asp Pro Pro Glu Ile Pro
            20                  25                  30

His Ala Thr Phe Lys Ala Met Ala Tyr Lys Glu Gly Thr Met Leu Asn
        35                  40                  45

Cys Glu Cys Lys Arg Gly Phe Arg Arg Ile Lys Ser Gly Ser Leu Tyr
50                  55                  60

Met Leu Cys Thr Gly Asn Ser Ser His Ser Ser Trp Asp Asn Gln Cys
65                  70                  75                  80

Gln Cys Thr Ser Ser Ala Thr Arg Asn Thr Thr Lys Gln Val Thr Pro
                85                  90                  95

Gln Pro Glu Glu Gln Lys Glu Arg Lys Thr Thr Glu Met Gln Ser Pro
            100                 105                 110

Met Gln Pro Val Asp Gln Ala Ser Leu Pro Gly His Cys Arg Glu Pro
        115                 120                 125

Pro Pro Trp Glu Asn Glu Ala Thr Glu Arg Ile Tyr His Phe Val Val
130                 135                 140

Gly Gln Met Val Tyr Tyr Gln Cys Val Gln Gly Tyr Arg Ala Leu His
145                 150                 155                 160

```
Arg Gly Pro Ala Glu Ser Val Cys Lys Met Thr His Gly Lys Thr Arg
                165                 170                 175

Trp Thr Gln Pro Gln Leu Ile Cys Thr Gly Glu Met Glu Thr Ser Gln
            180                 185                 190

Phe Pro Gly Glu Glu Lys Pro Gln Ala Ser Pro Glu Gly Arg Pro Glu
        195                 200                 205

Ser Glu Thr Ser Cys Leu Val Thr Thr Thr Asp Phe Gln Ile Gln Thr
    210                 215                 220

Glu Met Ala Ala Thr Met Glu Thr Ser Ile Phe Thr Thr Glu Tyr Gln
225                 230                 235                 240

Val Ala Val Ala Gly Cys Val Phe Leu Leu Ile Ser Val Leu Leu Leu
                245                 250                 255

Ser Gly Leu Thr Trp Gln Arg Arg Gln Arg Lys Ser Arg Arg Thr Ile
            260                 265                 270

<210> SEQ ID NO 58
<211> LENGTH: 551
<212> TYPE: PRT
<213> ORGANISM: Homo sapiens

<400> SEQUENCE: 58

Met Ala Ala Pro Ala Leu Ser Trp Arg Leu Pro Leu Leu Ile Leu Leu
1               5                   10                  15

Leu Pro Leu Ala Thr Ser Trp Ala Ser Ala Ala Val Asn Gly Thr Ser
            20                  25                  30

Gln Phe Thr Cys Phe Tyr Asn Ser Arg Ala Asn Ile Ser Cys Val Trp
        35                  40                  45

Ser Gln Asp Gly Ala Leu Gln Asp Thr Ser Cys Gln Val His Ala Trp
    50                  55                  60

Pro Asp Arg Arg Arg Trp Asn Gln Thr Cys Glu Leu Leu Pro Val Ser
65                  70                  75                  80

Gln Ala Ser Trp Ala Cys Asn Leu Ile Leu Gly Ala Pro Asp Ser Gln
                85                  90                  95

Lys Leu Thr Thr Val Asp Ile Val Thr Leu Arg Val Leu Cys Arg Glu
            100                 105                 110

Gly Val Arg Trp Arg Val Met Ala Ile Gln Asp Phe Lys Pro Phe Glu
        115                 120                 125

Asn Leu Arg Leu Met Ala Pro Ile Ser Leu Gln Val Val His Val Glu
    130                 135                 140

Thr His Arg Cys Asn Ile Ser Trp Glu Ile Ser Gln Ala Ser His Tyr
145                 150                 155                 160

Phe Glu Arg His Leu Glu Phe Glu Ala Arg Thr Leu Ser Pro Gly His
                165                 170                 175

Thr Trp Glu Glu Ala Pro Leu Leu Thr Leu Lys Gln Lys Gln Glu Trp
            180                 185                 190

Ile Cys Leu Glu Thr Leu Thr Pro Asp Thr Gln Tyr Glu Phe Gln Val
        195                 200                 205

Arg Val Lys Pro Leu Gln Gly Glu Phe Thr Thr Trp Ser Pro Trp Ser
    210                 215                 220

Gln Pro Leu Ala Phe Arg Thr Lys Pro Ala Ala Leu Gly Lys Asp Thr
225                 230                 235                 240

Ile Pro Trp Leu Gly His Leu Leu Val Gly Leu Ser Gly Ala Phe Gly
                245                 250                 255

Phe Ile Ile Leu Val Tyr Leu Leu Ile Asn Cys Arg Asn Thr Gly Pro
```

```
                  260                 265                 270
Trp Leu Lys Lys Val Leu Lys Cys Asn Thr Pro Asp Pro Ser Lys Phe
            275                 280                 285

Phe Ser Gln Leu Ser Ser Glu His Gly Gly Asp Val Gln Lys Trp Leu
            290                 295                 300

Ser Ser Pro Phe Pro Ser Ser Phe Ser Pro Gly Gly Leu Ala Pro
305                 310                 315                 320

Glu Ile Ser Pro Leu Glu Val Leu Glu Arg Asp Lys Val Thr Gln Leu
                325                 330                 335

Leu Leu Gln Gln Asp Lys Val Pro Glu Pro Ala Ser Leu Ser Ser Asn
            340                 345                 350

His Ser Leu Thr Ser Cys Phe Thr Asn Gln Gly Tyr Phe Phe Phe His
            355                 360                 365

Leu Pro Asp Ala Leu Glu Ile Glu Ala Cys Gln Val Tyr Phe Thr Tyr
        370                 375                 380

Asp Pro Tyr Ser Glu Glu Asp Pro Asp Glu Gly Val Ala Gly Ala Pro
385                 390                 395                 400

Thr Gly Ser Ser Pro Gln Pro Leu Gln Pro Leu Ser Gly Glu Asp Asp
                405                 410                 415

Ala Tyr Cys Thr Phe Pro Ser Arg Asp Asp Leu Leu Leu Phe Ser Pro
            420                 425                 430

Ser Leu Leu Gly Gly Pro Ser Pro Pro Ser Thr Ala Pro Gly Gly Ser
            435                 440                 445

Gly Ala Gly Glu Glu Arg Met Pro Pro Ser Leu Gln Glu Arg Val Pro
450                 455                 460

Arg Asp Trp Asp Pro Gln Pro Leu Gly Pro Pro Thr Pro Gly Val Pro
465                 470                 475                 480

Asp Leu Val Asp Phe Gln Pro Pro Glu Leu Val Leu Arg Glu Ala
                485                 490                 495

Gly Glu Glu Val Pro Asp Ala Gly Pro Arg Glu Gly Val Ser Phe Pro
            500                 505                 510

Trp Ser Arg Pro Pro Gly Gln Gly Glu Phe Arg Ala Leu Asn Ala Arg
            515                 520                 525

Leu Pro Leu Asn Thr Asp Ala Tyr Leu Ser Leu Gln Glu Leu Gln Gly
        530                 535                 540

Gln Asp Pro Thr His Leu Val
545                 550

<210> SEQ ID NO 59
<211> LENGTH: 369
<212> TYPE: PRT
<213> ORGANISM: Homo sapiens

<400> SEQUENCE: 59

Met Leu Lys Pro Ser Leu Pro Phe Thr Ser Leu Leu Phe Leu Gln Leu
1               5                   10                  15

Pro Leu Leu Gly Val Gly Leu Asn Thr Thr Ile Leu Thr Pro Asn Gly
            20                  25                  30

Asn Glu Asp Thr Thr Ala Asp Phe Phe Leu Thr Thr Met Pro Thr Asp
        35                  40                  45

Ser Leu Ser Val Ser Thr Leu Pro Leu Pro Glu Val Gln Cys Phe Val
    50                  55                  60

Phe Asn Val Glu Tyr Met Asn Cys Thr Trp Asn Ser Ser Ser Glu Pro
65                  70                  75                  80
```

Gln Pro Thr Asn Leu Thr Leu His Tyr Trp Tyr Lys Asn Ser Asp Asn
                85                  90                  95

Asp Lys Val Gln Lys Cys Ser His Tyr Leu Phe Ser Glu Glu Ile Thr
            100                 105                 110

Ser Gly Cys Gln Leu Gln Lys Lys Glu Ile His Leu Tyr Gln Thr Phe
        115                 120                 125

Val Val Gln Leu Gln Asp Pro Arg Glu Pro Arg Arg Gln Ala Thr Gln
    130                 135                 140

Met Leu Lys Leu Gln Asn Leu Val Ile Pro Trp Ala Pro Glu Asn Leu
145                 150                 155                 160

Thr Leu His Lys Leu Ser Glu Ser Gln Leu Glu Leu Asn Trp Asn Asn
                165                 170                 175

Arg Phe Leu Asn His Cys Leu Glu His Leu Val Gln Tyr Arg Thr Asp
            180                 185                 190

Trp Asp His Ser Trp Thr Glu Gln Ser Val Asp Tyr Arg His Lys Phe
        195                 200                 205

Ser Leu Pro Ser Val Asp Gly Gln Lys Arg Tyr Thr Phe Arg Val Arg
    210                 215                 220

Ser Arg Phe Asn Pro Leu Cys Gly Ser Ala Gln His Trp Ser Glu Trp
225                 230                 235                 240

Ser His Pro Ile His Trp Gly Ser Asn Thr Ser Lys Glu Asn Pro Phe
                245                 250                 255

Leu Phe Ala Leu Glu Ala Val Val Ile Ser Val Gly Ser Met Gly Leu
            260                 265                 270

Ile Ile Ser Leu Leu Cys Val Tyr Phe Trp Leu Glu Arg Thr Met Pro
        275                 280                 285

Arg Ile Pro Thr Leu Lys Asn Leu Glu Asp Leu Val Thr Glu Tyr His
    290                 295                 300

Gly Asn Phe Ser Ala Trp Ser Gly Val Ser Lys Gly Leu Ala Glu Ser
305                 310                 315                 320

Leu Gln Pro Asp Tyr Ser Glu Arg Leu Cys Leu Val Ser Glu Ile Pro
                325                 330                 335

Pro Lys Gly Gly Ala Leu Gly Glu Gly Pro Gly Ala Ser Pro Cys Asn
            340                 345                 350

Gln His Ser Pro Tyr Trp Ala Pro Pro Cys Tyr Thr Leu Lys Pro Glu
        355                 360                 365

Thr

<210> SEQ ID NO 60
<211> LENGTH: 133
<212> TYPE: PRT
<213> ORGANISM: Artificial Sequence
<220> FEATURE:
<223> OTHER INFORMATION: synthetic polypeptide
<220> FEATURE:
<221> NAME/KEY: misc_feature
<222> LOCATION: (125)..(125)
<223> OTHER INFORMATION: Xaa can be any naturally occurring amino acid

<400> SEQUENCE: 60

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

-continued

```
Lys Ala Thr Glu Leu Lys His Leu Gln Cys Leu Glu Glu Glu Leu Lys
    50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Xaa Gln Ser Ile
        115                 120                 125
Ile Ser Thr Leu Thr
    130
```

IL-2 MUTANT AND APPLICATION THEREOF

PRIORITY STATEMENT

This application is a national stage application under 35 U.S.C. § 371 of PCT International Application No. PCT/CN2021/116463, which has an international filing date of 3 Sep. 2021 and claims priority under 35 U.S.C. § 119 to Chinese Patent Application No. 202010918842.0 filed on 4 Sep. 2020 and Chinese Patent Application No. 202110932286.7 filed on 13 Aug. 2021. The contents of each application recited above are incorporated herein by reference in their entirety.

TECHNICAL FIELD

The disclosure relates to the field of biomedicine, in particular to IL-2 mutants and uses thereof.

BACKGROUND

Interleukin-2 (IL-2), initially identified as a T cell growth factor (TCGF), has been found to bind to its receptors and activate the proliferation and activation of immune cells such as T cells and NK cells in subsequent studies.

IL-2 receptors include IL-2R α subunit (CD25), IL-2R β subunit (CD122) and IL-2R γ subunit (CD132). Different subunits can form receptor complexes with different affinity, including high affinity receptor IL-2R αβγ, intermediate affinity receptor IL-2R βγ and low affinity receptor IL-2R α or IL-2R αβ. Different cells express different types of IL-2R subunits. For example, traditional T cells (CD4+ T and CD8+ T) in their resting state generally express on cell surface IL-2 receptor β (ILL-2R β, CD122) and IL-2 receptor γ (IL-2R γ, CD132), but hardly express IL-2 α receptor (IL-2R α, CD25). However, in addition to IL-2R β and IL-2R γ, IL-2R α is constitutively highly expressed in regulatory T cells (Tregs).

At present, researchers are trying to use IL-2 or its mutants to activate immune cells or a subset of immune cells to treat tumors or autoimmune diseases. For example, high doses of IL-2 have been approved for the treatment of malignant melanoma or metastatic renal cell carcinoma, and a PEG-IL-2 conjugate, NKTR-358, has been approved for clinical trials of autoimmune diseases.

Therefore, it is of great significance for development of IL-2 drugs to improve the stability and yield of IL-2 and/or change its binding ability to certain receptor complexes. In view of this, the present disclosure is proposed.

SUMMARY

The present disclosure provides IL-2 mutants, fusion proteins, conjugates, nucleic acid fragments, vectors, host cells, methods for preparing the mutants or fusion proteins, IL-2 mutants or fusion proteins prepared according to the methods, pharmaceutical compositions, pharmaceutical uses, therapeutic methods, and methods for preferentially stimulating regulatory T cells.

In a first aspect, the disclosure provides an IL-2 mutant comprising one or more mutation(s) at Q13, L18, G27, Y31, A73, H79, P82, I89, N90, V91, V93, F117 or R120 compared to wild-type IL-2.

In some specific embodiments, the mutation is deletion, insertion or substitution, preferably substitution.

In some specific embodiments, the IL-2 mutant comprises one or more mutation(s) of Q13L, L18I, G27W, Y31V, A73L, H79Q, P82L, I89L, N90Y, V91A, V93I, F117W or R120F.

In some specific embodiments, the IL-2 mutant comprises at least one group of mutation(s) in groups (a)-(h):
(a). mutations at Y31/A73/H79; preferably, Y31V/A73L/H79Q;
(b). a mutation at Q13; preferably, Q13L;
(c). a mutation at R120; preferably, R120F;
(d). mutations at L18/V91/F117; preferably, L18I/V91A/F117W;
(e). mutations at L18/I89/V93; preferably, L18I/I89L/V93I;
(f). mutations at G27/R120; preferably, G27W/R120F;
(g). mutations at P82/R120; preferably, P82L/R120F;
(h). mutations at N90/R120; preferably, N90Y/R120F.

In some specific embodiments, the IL-2 mutant has an amino acid sequence as shown in any one of SEQ ID NOs: 2 to 9.

In some specific embodiments, the IL-2 mutant has a Tm value higher than that of the wild-type IL-2.

In some specific embodiments, the wild-type IL-2 has an amino acid sequence as shown in SEQ ID NO: 60 or SEQ ID NO: 1.

In some specific embodiments, the IL-2 mutant further comprises one or more mutation(s) selected from the group consisting of mutation at H16, D20, N88, V91 or Q126, e.g., H16E, D20A, D20H, D20Y, N88A, N88I, N88G, N88R, N88D, V91R, V91K, Q126L or Q126F.

Preferably, the IL-2 mutant further comprises at least one group of mutation(s) selected from groups (i)-(iv):
(i). a mutation at H16; preferably, H16E;
(ii). a mutation at D20; preferably, D20A;
(iii). a mutation at V91; preferably V91R;
(iv). mutations at H16/V91; preferably, H16E/V91R.

In some specific embodiments, the IL-2 mutant comprises at least one group of mutation(s) in groups (a)-(n):
(a). mutations at H16/Y31/A73/H79; preferably, H16E/Y31V/A73L/H79Q;
(b). mutations at H16/R120; preferably, H16E/R120F;
(c). mutations at H16/L18/V91/F117; preferably, H16E/L18I/V91A/F117W;
(d). mutations at H16/L18/I89/V93; preferably, H16E/L18I/I89L/V93I;
(e). mutations at H16/G27/R120; preferably, H16E/G27W/R120F;
(f). mutations at H16/P82/R120; preferably, H16E/P82L/R120F;
(g). mutations at D20/Y31/A73/H79; preferably, D20A/Y31V/A73L/H79Q;
(h). mutations at D20/R120; preferably, D20A/R120F;
(i). mutations at V91/Y31/A73/H79; preferably, V91R/Y31V/A73L/H79Q;
(j). mutations at V91/Q13; preferably, V91R/Q13L;
(k). mutations at V91/R120; preferably, V91R/R120F;
(l). mutations at V91/L18/I89/V93; preferably, V91R/L18I/I89L/V93I;
(m). mutations at H16/V91/Y31/A73/H79; preferably, H16E/V91R/Y31V/A73L/H79Q;
(n). mutations at H16/V91/L18/I89/V93; preferably, H16E/V91R/L18I/I89L/V93I.

In some specific embodiments, the IL-2 mutant has an amino acid sequence as shown in any one of SEQ ID NOs: 22 to 27, SEQ ID NOs:29 to 30, SEQ ID NOs:32 to 35 or SEQ ID NOs:37 to 38.

In some specific embodiments, the IL-2 mutant further comprises one or more mutation(s) selected from the group consisting of mutation at N26, N29, N30, N71, Q11, L132, L70, P82, G27 or F28.

Preferably, the IL-2 mutant further comprises one or more mutation(s) selected from the group consisting of N26Q, N29S, N30S, N71Q, Q11C, L132C, L70C, P82C, G27C or F78C.

More preferably, the IL-2 mutant further comprises at least one group of mutation(s) in groups (a)-(g):
(a). N26Q;
(b). N29S;
(c). N30S;
(d). N71Q;
(e). Q11C/L132C;
(f). L70C/P82C;
(g). G27C/F78C.

In some specific embodiments, the IL-2 mutant further comprises one or more mutation(s) selected from the group consisting of mutation at F42, Y45 or L72, preferably, F42A, Y45A or L72G.

In some specific embodiments, the IL-2 mutant has a reduced binding ability to IL-2Rβγ subunit complex compared to the wild-type IL-2; preferably, the binding ability$_{IL\text{-}2R\beta\gamma\ subunit\ complex}$/binding ability$_{IL\text{-}2\alpha\beta\gamma\ subunit\ complex}$ decreases.

In some specific embodiments, the mutant has a reduced stimulation ability to non-regulatory T cells or NK (natural killer) cells compared to the wild-type IL-2; the stimulation can be selected from intracellular STAT5 phosphorylation or cell proliferation.

In some specific embodiments, the mutant preferentially stimulates regulatory T cells (Tregs) in peripheral blood or T cell population compared to non-regulatory T cells or NK (natural killer) cells; said preferentially stimulating can be selected from preferentially stimulating STAT5 phosphorylation in regulatory T cells, preferentially stimulating regulatory T cell proliferation, increasing regulatory T cells to non-regulatory T cells ratio, or increasing regulatory T cells to NK cells ratio.

In a second aspect, the disclosure provides an IL-2 mutant comprising one or more mutation(s) at H16, D20 or V91 compared to wild-type IL-2; preferably, the IL-2 mutant comprises at least one group of mutation(s) selected from the groups (i)-(iv):
(i). a mutation at H16; preferably, H16E;
(ii). a mutation at D20; preferably, D20A;
(iii) a mutation at V91; preferably V91R;
(iv). mutations at H16/V91; preferably, H16E/V91R.

In some specific embodiments, the IL-2 mutant has an amino acid sequence as shown in SEQ ID NOs: 21, 28, 31 or 36.

In some specific embodiments, the IL-2 mutant further comprises one or more mutation(s) selected from the group consisting of mutation at N26, N29, N30, N71, Q11, L132, L70, P82, G27 or F28.

Preferably, the IL-2 mutant further comprises one or more mutations selected from the group consisting of N26Q, N29S, N30S, N71Q, Q11C, L132C, L70C, P82C, G27C or F78C.

More preferably, the IL-2 mutant further comprises at least one group of mutation(s) in groups (a)-(g):
(a). N26Q;
(b). N29S;
(c). N30S;
(d). N71Q;
(e). Q11C/L132C;
(f). L70C/P82C;
(g). G27C/F78C.

In some specific embodiments, the IL-2 mutant has a reduced binding ability to IL-2R βγ subunit complex compared to the wild-type IL-2; preferably, the binding ability$_{IL\text{-}2R\beta\gamma\ subunit\ complex}$/binding ability$_{IL\text{-}2\alpha\beta\gamma\ subunit\ complex}$ decreases.

In some specific embodiments, the mutant has reduced stimulation ability to non-regulatory T cells or NK (natural killer) cells compared to the wild-type IL-2, and the stimulation can be selected from intracellular STAT5 phosphorylation or cell proliferation.

In some specific embodiments, the mutant preferentially stimulates regulatory T cells (Tregs) in peripheral blood or T cell population compared to non-regulatory T cells or NK cells; said preferentially stimulating can be selected from preferentially stimulating STAT5 phosphorylation in regulatory T cells, preferentially stimulating regulatory T cell proliferation, increasing regulatory T cells to non-regulatory T cells ratio, or increasing regulatory T cells to NK cells ratio.

In some specific embodiments, the mutation comprises deletion, insertion or substitution, preferably substitution.

In some specific embodiments, the wild-type IL-2 has an amino acid sequence as shown in SEQ ID NO: 60 or SEQ ID NO: 1.

In a third aspect, the present disclosure provides a fusion protein comprising a first polypeptide and a second polypeptide, wherein the first polypeptide is the IL-2 mutant as described above and the second polypeptide is a non-IL-2 polypeptide.

In some specific embodiments, the second polypeptide is an Fc, a tumor-antigen-binding molecule or an IL-2 receptor subunit;
optionally, the Fc is a human IgG Fc, for example a human IgG1 Fc;
preferably, the human IgG1 Fc comprises at least one group of mutation(s) selected from the groups (a)-(i):
(a). C220S;
(b). N297G;
(c). C220S and N297G;
(d). A327Q;
(e). L234A and L235A;
(f). A287C and L306C;
(g). A259C and L306C;
(h). R292C and V302C;
(i). V323C and I332C;
more preferably, the human IgG1 Fc has an amino acid sequence as shown in SEQ ID NO: 11;
optionally, the tumor antigen comprises EDB-FN (extra domain of fibronectin), Muc1, p53, FAP, GD2, EpCAM, tenascin-C, CD20, CEA, MAdCAM-1 or WT1 (Wilms Tumor Protein 1); optionally, the tumor-antigen-binding molecule is an antibody, such as scFv, sdFv, Fab, Fab', F(ab')$_2$ or Fv;
optionally, the IL-2 receptor subunit is an IL-2 receptor a subunit.

In some specific embodiments, C-terminus of the first polypeptide is linked to N-terminus of the second polypeptide with or without a linker; or N-terminus of the first polypeptide is linked to C-terminus of the second polypeptide with or without a linker;
preferably, the linker is selected from: $(G_4S)_n$, $(GGNGT)_n$ or $(YGNGT)_n$, and the n is selected from 1, 2, 3, 4 or 5;

more preferably, the C-terminus of the first polypeptide is linked to the N-terminus of the second polypeptide by a linker $(G_4S)_3$.

In some specific embodiments, the fusion protein comprises an amino acid sequence as shown in any one of SEQ ID NOs: 13 to 20 or SEQ ID NOs: 39 to 56.

In a fourth aspect, the present disclosure provides a conjugate comprising the mutant or the fusion protein as described above, and further comprising a stabilizer, drug or tracer molecule conjugated to the mutant or fusion protein; wherein the stabilizer can be selected from polyethylene glycol, such as monomethoxy polyethylene glycol.

In a fifth aspect, the present disclosure provides an isolated nucleic acid fragment encoding the mutant or the fusion protein as described above.

In a sixth aspect, the present disclosure provides a vector comprising the nucleic acid fragment as described above.

In a seventh aspect, the present disclosure provides a host cell comprising the vector as described above.

In some specific embodiments, the host cell is a prokaryotic cell or a eukaryotic cell; the prokaryotic cell or the eukaryotic cell can be selected from *Escherichia coli*, yeast, insect cells or mammalian cells, and the mammalian cells can be selected from a CHO cell line or a HEK293 cell line.

In an eighth aspect, the present disclosure provides a method for preparing the mutant or the fusion protein as described above, wherein the method comprises culturing the aforementioned host cell and isolating the IL-2 mutant or fusion protein expressed by the host cell.

In a ninth aspect, the present disclosure provides an IL-2 mutant or fusion protein prepared according to the aforementioned method.

In a tenth aspect, the present disclosure provides a pharmaceutical composition comprising the aforementioned mutant, fusion protein, conjugate, nucleic acid fragment, vector or host cell; and a pharmaceutically acceptable carrier, diluent or adjuvant;
  preferably, the pharmaceutical composition is a pharmaceutical composition for injection, e.g. for intravenous or subcutaneous injection; more preferably, the pharmaceutical composition per dose comprises an effective amount of fusion protein to be administrated to a subject; most preferably, the effective amount is 0.001-10 mpk, such as 0.001 mpk, 0.002 mpk, 0.003 mpk, 0.004 mpk, 0.005 mpk, 0.006 mpk, 0.007 mpk, 0.008 mpk, 0.009 mpk, 0.01 mpk, 0.02 mpk, 0.03 mpk, 0.04 mpk, 0.05 mpk, 0.06 mpk, 0.07 mpk, 0.08 mpk, 0.09 mpk, 0.1 mpk, 0.2 mpk, 0.3 mpk, 0.4 mpk, 0.5 mpk, 0.6 mpk, 0.7 mpk, 0.8 mpk, 0.9 mpk, 1 mpk, 2 mpk, 3 mpk, 4 mpk, 5 mpk, 6 mpk, 7 mpk, 8 mpk, 9 mpk or 10 mpk.

In an eleventh aspect, the present disclosure provides use of the aforementioned mutant, fusion protein, conjugate, nucleic acid fragment, vector or host cell in the manufacture of a medicament for treating disease;
  preferably, the medicament is a medicament for injection, e.g., for intravenous or subcutaneous injection;
  preferably, the medicament per dose comprises an effective amount of fusion protein to be administrated to a subject; most preferably, the effective amount is 0.001-10 mpk, such as 0.001 mpk, 0.002 mpk, 0.003 mpk, 0.004 mpk, 0.005 mpk, 0.006 mpk, 0.007 mpk, 0.008 mpk, 0.009 mpk, 0.01 mpk, 0.02 mpk, 0.03 mpk, 0.04 mpk, 0.05 mpk, 0.06 mpk, 0.07 mpk, 0.08 mpk, 0.09 mpk, 0.1 mpk, 0.2 mpk, 0.3 mpk, 0.4 mpk, 0.5 mpk, 0.6 mpk, 0.7 mpk, 0.8 mpk, 0.9 mpk, 1 mpk, 2 mpk, 3 mpk, 4 mpk, 5 mpk, 6 mpk, 7 mpk, 8 mpk, 9 mpk or 10 mpk;
  preferably, the medicament is used for treating an autoimmune disease, proliferative disease, or viral infection;
  more preferably, the autoimmune disease comprises rheumatoid arthritis, ankylosing spondylitis, systemic lupus erythematosus, cutaneous lupus erythematosus, lupus nephritis, IgA nephropathy, Sjogren's syndrome, polymyositis, dermatomyositis, scleroderma, psoriasis, plaque psoriasis, alopecia areata, multiple sclerosis, amyotrophic lateral sclerosis, inflammatory bowel disease, ulcerative colitis, Crohn's disease, graft-versus-host disease, organ transplant rejection, autoimmune hepatitis, type I diabetes, autoimmune vasculitis, eczema or asthma;
  more preferably, the proliferative disease comprises neoplasm, solid tumor, hematological tumor, malignant ascites or malignant pleural effusion; wherein the solid tumor can be benign or malignant, primary or metastatic, the malignant solid tumor can be a cancer or a sarcoma, for example, epithelial cell carcinoma, endothelial cell carcinoma, squamous cell carcinoma, teratoma, lung tumor, papillomavirus-induced cancer, adenocarcinoma, carcinoma, melanoma, angiosarcoma, neuroblastoma, metastatic lung cancer, non-small cell lung cancer, small cell lung cancer, breast cancer, Merkel cell cancer, ovarian cancer, renal cell cancer, metastatic renal cancer, head and neck cancer, bladder cancer, non-muscle invasive bladder cancer; the hematological tumor can be leukemia, lymphoma, multiple myeloma, such as B-cell lymphoma, T-cell lymphoma, cutaneous T-cell lymphoma, T-cell large granular lymphocytic leukemia;
  more preferably, the viral infection is selected from HIV infection, novel coronavirus infection or HPV viral infection.

In a twelfth aspect, the present disclosure provides a method for treating an autoimmune disease, proliferative disease, or viral infection, wherein the method comprises a step of administering to a subject an effective amount of the aforementioned IL-2 mutant, fusion protein, conjugate, nucleic acid fragment, vector, host cell or pharmaceutical composition;
  preferably, the step of administering is performed via injection, e.g. intravenous or subcutaneous injection;
  preferably, the effective amount is 0.001-10 mpk, such as 0.001 mpk, 0.002 mpk, 0.003 mpk, 0.004 mpk, 0.005 mpk, 0.006 mpk, 0.007 mpk, 0.008 mpk, 0.009 mpk, 0.01 mpk, 0.02 mpk, 0.03 mpk, 0.04 mpk, 0.05 mpk, 0.06 mpk, 0.07 mpk, 0.08 mpk, 0.09 mpk, 0.1 mpk, 0.2 mpk, 0.3 mpk, 0.4 mpk, 0.5 mpk, 0.6 mpk, 0.7 mpk, 0.8 mpk, 0.9 mpk, 1 mpk, 2 mpk, 3 mpk, 4 mpk, 5 mpk, 6 mpk, 7 mpk, 8 mpk, 9 mpk or 10 mpk;
  preferably, the autoimmune disease comprises rheumatoid arthritis, ankylosing spondylitis, systemic lupus erythematosus, cutaneous lupus erythematosus, lupus nephritis, IgA nephropathy, Sjogren's syndrome, polymyositis, dermatomyositis, scleroderma, psoriasis, plaque psoriasis, alopecia areata, multiple sclerosis, amyotrophic lateral sclerosis, inflammatory bowel disease, ulcerative colitis, Crohn's disease, graft-versus-host disease, organ transplant rejection, autoimmune hepatitis, type I diabetes, autoimmune vasculitis, eczema or asthma;
  preferably, the proliferative disease comprises neoplasm, solid tumor, hematological tumor, malignant ascites or malignant pleural effusion; wherein the solid tumor is optionally selected from benign or malignant, primary or metastatic, the malignant solid tumor is optionally selected from a cancer or a sarcoma, for example, epithelial cell carcinoma, endothelial cell carcinoma, squamous cell carcinoma, teratoma, lung tumor, papillomavirus-induced cancer, adenocarcinoma, carcinoma, melanoma, angiosarcoma, neuroblastoma, metastatic lung cancer, non-small cell lung cancer, small cell lung cancer, breast cancer, Merkel cell cancer, ovarian cancer, renal cell cancer, metastatic renal cancer, head and neck cancer, bladder cancer, non-muscle invasive bladder cancer; the hematological tumor is optionally selected from selected from leukemia, lymphoma, multiple myeloma, such as B-cell lymphoma, T-cell lymphoma, cutaneous T-cell lymphoma, T-cell large granular lymphocytic leukemia;

more preferably, the viral infection is selected from HIV infection, novel coronavirus infection or HPV viral infection.

In a thirteenth aspect, the present disclosure provides a method for preferentially stimulating a T cell population or regulatory T cells in peripheral blood, wherein the method comprises a step of contacting the T cell population or peripheral blood with the aforementioned IL-2 mutant, fusion protein, conjugate, nucleic acid fragment, vector, host cell, or pharmaceutical composition;

preferably, said preferential stimulating comprises:
(a) preferentially stimulating STAT5 phosphorylation of regulatory T cells compared to non-regulatory T cells or NK cells;
(b) preferentially stimulating proliferation of regulatory T cells compared to non-regulatory T cells or NK cells; and/or
(c) increasing regulatory T cells to non-regulatory T cells ratio, or increasing regulatory T cells to NK cells ratio.

Terms and Definitions

Unless otherwise defined in the present disclosure, the scientific and technical terms related to the present disclosure shall have the meanings commonly understood by those skilled in the art.

As used herein, unless otherwise stated, the term "IL2" or "IL-2" refers to any natural or recombinant IL-2 derived from any vertebrates, including mammals such as primates (e.g., human) and rodents (e.g., mice and rats) and domesticated or farm mammals. The "IL2" or "IL-2" in the present disclosure includes any form ranging from unprocessed IL-2 (e.g., IL-2 comprising a signal peptide at N-terminus) to mature IL-2 in a cell. The "IL2" or "IL-2" in the present disclosure also includes natural variants and fragments of IL-2, such as splice variants or allelic variants. The "IL2" or "IL-2" as used herein also includes non-naturally occurring mutants, such as IL-2 mutants artificially modified by genetic engineering.

The term "wild-type IL-2" is the same as the IL-2 mutant, except that each amino acid at the mutation positions of the IL-2 mutant is maintained as wild-type amino acid. For example, if the IL-2 mutant is an unprocessed IL-2, then the wild-type form of the mutant is an unprocessed IL-2; if the IL-2 mutant is a mature IL-2, then the wild-type form of the mutant is a mature IL-2; if the IL-2 mutant is a truncated form of IL-2, then the wild-type form of the mutant is the corresponding truncated form of IL-2 with a wild-type sequence. As an example, the "wild-type IL-2" in the present disclosure may have an amino acid sequence as follow:

APTSSSTKKTQLQLEHLLLDLQMILNGIN-NYKNPKLTRMLTFKFYMPKKATELKHL QCLEEELKPLEEVLNLAQSKNFHLRPRDLISNIN-VIVLELKGSETTFMCEYADETATIVEFL NRWITFXQSI-ISTLT (SEQ ID NO: 60); wherein the 125th amino acid residue "X" represents C, S, A or V.

As used herein, the term "mutation" comprises amino acid substitution, deletion, insertion, or any combination thereof. The "mutation" in the present disclosure may be generated by genetic or chemical methods known in the art, including, but not limited to, site-directed mutagenesis, PCR, gene synthesis, and the like.

The numbering of "mutation site" of an IL-2 mutant starts from the first amino acid residue (A) of the "wild-type IL-2" as shown in SEQ ID NO: 60. As an example, the "Q13 mutation" refers to mutation of the amino acid residue (Gln, Q) at position 13 of the wild-type IL-2 as shown in SEQ ID NO: 60. For example, the "Q13L mutation" refers to an IL-2 mutant in which the amino acid Q (Gln) at position 13 of the wild-type IL-2 as shown in SEQ ID NO: 60 is mutated to L (Leu).

As used herein, the punctuation "/" used between mutation sites means "and", which indicates that the mutations before and after "/" coexist in the same IL-2 mutant at the same time. For example, "Y31/A73/H79" means that mutations occur simultaneously at Y31, A73 and H79 in the same IL-2 mutant, and "Y31V/A73L/H79Q" means that Y31V, A73L and H79Q coexist in the same IL-2 mutant at the same time.

As used herein, the term "Tm" (melting temperature) refers to a temperature at which 50% of protein is denatured. The "Tm" in present disclosure may be determined by any methods well known in the art. For example, the Tm value of protein can be determined by the method shown in example 3 or 6 of the present disclosure.

The term "fusion protein" in the present disclosure refers to a protein product obtained by connecting the coding regions of two or more genes by genetic recombination, chemical or other suitable methods, and expressing the protein product obtained by genetic recombination under the control of the same regulatory sequence. In the fusion protein of the present disclosure, the coding regions of two or more genes can be fused at one or several positions by the sequence encoding linker(s). Linker(s) can be used to construct the fusion protein of the present disclosure.

As used herein, the term "linker" refers to a peptide used to link IL-2 to another protein molecule or protein fragment to ensure the correct folding and stability of protein. Said another molecule includes, but is not limited to, Fc. Preferably, the "linker" in the disclosure is $(GGGGS)_n$, wherein n may be 0, 1, 2, 3, 4 or 5. If a linker sequence is too short, it may affect the folding of higher-order structure of two proteins, so that the two proteins interfere with each other. If a linker sequence is too long, it may involve immunogenicity, because the linker sequence itself is a new antigen.

As used herein, the term "second polypeptide" may be a single-chain polypeptide, such as scFv antibody. The "second polypeptide" also includes a multi-chain polypeptide, wherein at least one polypeptide chain is fused to IL-2 or a mutant thereof, and the other polypeptide chain(s) is or are linked to the at least one polypeptide chain as fused by covalent or non-covalent bond(s). For example, for Fab antibody, the heavy chain of Fab can be fused to IL-2 or a mutant thereof, and the light chain is linked to the heavy chain by disulfide bond(s).

As used herein, the term "Fc" refers to the constant region of an immunoglobulin chain, in particular the carboxyl terminus of the constant region of an immunoglobulin heavy chains or a part thereof. Fc has no antigen-binding activity and is the region where the antibodies interact with effector molecules or cells. "Fc" as used herein may be any Fc or a variant thereof, which is derived from human or non-human mammals. For example, an immunoglobulin Fc may comprise a combination of two or more domains (CH1, CH2, CH3 or CH4) of heavy chains and an immunoglobulin hinge region. Fc can be derived from different species, preferably derived from human immunoglobulin. According to the amino acid sequence of the constant region of heavy chains, immunoglobulin can be divided into different classes, mainly including five classes of immunoglobulins: IgA, IgD, IgE, IgG and IgM. Some of them can be further divided into subclasses (isotypes), such as IgG-1, IgG-2, IgG-3 and IgG-4; IgA-1 and IgA-2. Preferably, "Fc" comprises at least one immunoglobulin hinge region, as well as the CH2 and CH3 domains of the IgG. More preferably, "Fc" comprises a CH2 domain, a CH3 domain and an immunoglobulin hinge region of IgG1, and the starting amino acid position of the hinge region can be varied. Unless otherwise stated, the amino acid residues of the Fc, constant region or antibody of the present disclosure are numbered according to the EU numbering system, also known as EU index, as described in Kabat et al., Sequences of Proteins of Immunological Interest, 5th Edition, Public Health Service, National Institutions of Health, Bethesda, Md., 1991.

The "antibody" of the present disclosure is used in the broadest sense and encompasses various antibody structures, including but not limited to monoclonal antibodies, polyclonal antibodies, multispecific antibodies (e.g., bispecific antibodies) and antigen-binding fragments, as long as they exhibit the desired antigen-binding activity. The antibodies may include murine antibodies, human antibodies, humanized antibodies, chimeric antibodies and camel antibodies. Illustratively, the antibody can be an immunoglobulin, which is a tetrapeptide chain structure composed of two identical heavy chains and two identical light chains connected by interchain disulfide bonds. The immunoglobulin heavy chain constant regions are different in terms of amino acid composition and sequence, and thus antigenicity. Therefore, immunoglobulin can be divided into five classes, or isotypes of immunoglobulin, namely IgM, IgD, IgG, IgA and IgE, and their corresponding heavy chains are μ chain, δ chain, γ chain, α chain and ε chain respectively. According to the difference of amino acid composition in the hinge region and the number and position of heavy chain disulfide bonds, the same class of Ig can be divided into different subclasses, for example, IgG can be divided into IgG1, IgG2, IgG3 and IgG4. Light chains may be divided into κ chains or λ chains according to the difference of the constant region. Each of the five classes of Ig can have κ chains or λ chains. The "antibody" in present disclosure also includes scFv, sdFv, Fab, Fab', F(ab')$_2$ and Fv.

As used herein, the term "isolated" refers to removal of a material from its original or natural environment (e. g., the natural environment in which it naturally exists). Therefore, the natural polynucleotides or polypeptides present in living animals are not isolated, but the same polynucleotides or polypeptides isolated from some or all coexisting materials in the natural system by human intervention are isolated.

An "isolated nucleic acid fragment" is an RNA or DNA polymer, which is single-stranded or double-stranded, and optionally contains synthetic, unnatural or altered nucleotide bases. The isolated nucleic acid fragment in the form of a DNA polymer may consist of one or more cDNAs, genomic DNAs, or synthetic DNA fragments. The "nucleic acid fragment" of the present disclosure may be a part of a vector and integrated into a host cell chromosome at a heterologous site. The "nucleic acid fragment" of the present disclosure may be a part of a composition. Since such vector or composition is not a part of its natural environment, it is still isolated.

As used herein, the term "vector" includes a nucleic acid vector, such as a DNA vector (e. g., a plasmid), an RNA vector, a virus or other suitable replicon (e.g., a viral vector). Various vectors have been developed to deliver polynucleotides for encoding foreign proteins into prokaryotic or eukaryotic cells. The "vector" of the present disclosure may contain additional sequence elements for expressing proteins and/or integrating these polynucleotide sequences into the genome of mammalian cells, regulatory sequences (such as promoter and enhancer regions) for directing gene transcription, or sequences for enhancing the translation rate of genes or improving the stability or nuclear export of mRNA produced by gene transcription. The sequence elements include, for example, 5' and 3' untranslated regions, internal ribosomal entry sites (IRES) and polyadenylation signal sites in order to direct efficient transcription of genes carried on expression vectors. The "vector" of the present disclosure may further comprise a polynucleotide encoding a marker for selecting cells containing such a vector. Examples of suitable markers include genes encoding antibiotic resistance, such as ampicillin, chloramphenicol, kanamycin or nourseothricin.

As used herein, the term "host cell" refers to a cell into which an exogenous nucleic acid has been introduced, including progeny of such a cell. The "progeny" may have exactly the same nucleic acid content as their parent, or may contain mutations and is not exactly the same as the parent cell. The "progeny" includes mutant progeny that have the same function or biological activity as the function or biological activity screened or selected in the original transformed cells.

As used herein, the term "pharmaceutical composition" refers to a mixture containing one or more of IL-2 mutants, fusion proteins, nucleic acid fragments, vectors or host cells of the present disclosure. The mixture further comprises other components, including but not limited to, pharmaceutically acceptable carriers, diluents or adjuvants thereof. The purpose of the pharmaceutical composition of the disclosure is to facilitate the administration of drugs to organisms, which promotes the absorption of active ingredients to exert their biological activity.

The term "treatment" of the present disclosure refers to a surgical or pharmaceutical treatment, the purpose of which is to prevent, or mitigate (reduce) the progression of undesirable physiological changes or lesions, such as cell proliferative disorders (e.g., cancers or infectious diseases), autoimmune diseases (e.g., systemic lupus erythematosus) in subjects in need of treatment. Beneficial or desired clinical results include, but are not limited to, relief of symptoms, alleviation of disease severity, stabilization (i.e., no deterioration) of the disease state, delay or slowdown of disease progression, improvement or mitigation of disease status, and remission (whether partial or complete), whether detectable or undetectable. The subjects in need of treatment include those who suffer from diseases or disorders, those who are susceptible to diseases or disorders or those who intend to prevent diseases or disorders. When the terms "alleviation", "reduction", "mitigation", "amelioration" and "remission" are used, it also means elimination, disappearance, non-occurrence, and the like.

As used herein, the term "subject" refers to an organism receiving treatment for specific diseases or disorders (such as cancers or infectious diseases or autoimmune diseases) as described herein. Examples of subjects and patients include mammals, such as humans, primates, pigs, goats, rabbits, hamsters, cats, dogs, guinea pigs, cattle or other members of bovine family, sheep and horses, receiving treatment for diseases or disorders.

As used herein, the term "effective amount" refers to an amount of a therapeutic agent that is effective in preventing or alleviating symptoms or progression of a disease, when the therapeutic agent is administered to a cell, tissue or subject, alone or in combination with another therapeutic agent. The "effective amount" also refers to an amount of a compound that is sufficient to relieve symptoms (such as, to treat, cure, prevent or relieve related medical conditions), or increase the rate of treating, curing, preventing or relieving those conditions. When an active ingredient is administered to an individual alone, the therapeutically effective amount refers solely to the active ingredient. When a combination is administrated, the therapeutically effective amount refers to the combined amount of active ingredients that have a therapeutic effect, whether they are administered in combination, continuously or simultaneously.

The term "autoimmune disease" of the present disclosure refers to a condition characterized by damage to cells, tissues and/or organs caused by the immune response of a subject to its own cells, tissues and/or organs. As an example, autoimmune diseases include but are not limited to rheumatoid arthritis, ankylosing spondylitis, systemic lupus erythematosus, cutaneous lupus erythematosus, lupus nephritis, IgA nephropathy, Sjogren's syndrome, polymyositis, dermatomyositis, scleroderma, psoriasis, plaque psoriasis, alopecia areata, multiple sclerosis, amyotrophic lateral sclerosis, inflammatory bowel disease, ulcerative colitis, Crohn's disease, graft-versus-host disease, organ transplant rejection, autoimmune hepatitis, type I diabetes, autoimmune vasculitis, eczema or asthma.

The term "proliferative disease" of the present disclosure refers to a condition in which the growth of cells or tissues is out of control and/or abnormal, which may lead to the development of undesired conditions or diseases. It may or may not be cancerous, including but not limited to neoplasms, solid tumors, hematological tumors, malignant ascites or malignant pleural effusion. The "solid tumor" of the present disclosure can be benign or malignant, primary or metastatic; and malignant solid tumors can be carcinomas or sarcomas. As an example, the "solid tumor" of the present disclosure includes, but is not limited to, epithelial cell carcinoma, endothelial cell carcinoma, squamous cell carcinoma, teratoma, lung tumor, papillomavirus-induced cancer, adenocarcinoma, carcinoma, melanoma, angiosarcoma, neuroblastoma, metastatic lung cancer, non-small cell lung cancer, small cell lung cancer, breast cancer, Merkel cell cancer, ovarian cancer, renal cell cancer, metastatic renal cancer, head and neck cancer, bladder cancer, non-muscle invasive bladder cancer. As an example, the "hematological tumor" of the present disclosure includes, but is not limited to, leukemia, lymphoma, multiple myeloma, such as B-cell lymphoma, T-cell lymphoma, cutaneous T-cell lymphoma, T-cell large granular lymphocytic leukemia.

As used herein, the term "IL-2 receptor a subunit" (IL-2Rα), also known as "CD25", refers to any natural IL-2 receptor a subunits or mutants thereof derived from any vertebrates, including mammals such as primates (e.g., humans) and rodents (e.g., mice and rats). The "IL-2 receptor a subunit" includes "full-length" unprocessed IL-2 receptor a subunits, any form of processed IL-2 receptor a subunits derived from cells, naturally occurring IL-2 receptor a subunit variants (such as splice variants or allelic variants), and artificially engineered mutants on the basis of natural IL-2 receptor a subunits. In certain embodiments, the IL-2 receptor a subunit is a human IL-2 receptor a subunit with an exemplary sequence as shown in SEQ ID NO: 57.

As used herein, the term "IL-2 receptor β subunit" (IL-2Rβ), also known as "CD122", refers to any natural IL-2 receptor β subunits or mutants thereof derived from any vertebrates, including mammals such as primates (e.g., humans) and rodents (e.g., mice and rats), The IL-2 receptor β subunit includes "full-length" unprocessed IL-2 receptor β subunits, any form of processed IL-2 receptor β subunits derived from cells, naturally occurring IL-2 receptor β subunit variants (such as splice variants or allelic variants), and artificially engineered mutants on the basis of natural IL-2 receptor β subunits. In certain embodiments, the IL-2 receptor β subunit is a human IL-2 receptor β subunit with an exemplary sequence as shown in SEQ ID NO: 58.

As used herein, the term "IL-2 receptor γ subunit" (IL-2Rγ), also known as "CD132", refers to any natural IL-2 receptor γ subunits or mutants thereof derived from any vertebrates, including mammals such as primates (e.g., humans) and rodents (e.g., mice and rats), The IL-2 receptor γ subunit includes "full-length" unprocessed IL-2 receptor γ subunits, any form of processed IL-2 receptor γ subunits derived from cells, naturally occurring IL-2 receptor γ subunit variants (such as splice variants or allelic variants), and artificially engineered mutants on the basis of natural IL-2 receptor γ subunits. In certain embodiments, the IL-2 receptor γ subunit is a human IL-2 receptor γ subunit with an exemplary sequence as shown in SEQ ID NO: 59.

As used herein, the term "Treg", also known as "regulatory T cell" or "$T_{regulatory\ cell}$", refers to a specialized CD4$^+$ T cell type which can inhibit the response of other T cells. Treg is characterized by expressing IL-2 receptor α subunit (CD25) and transcription factor Forkhead box protein P3 (FOXP3), and plays a key role in inducing and maintaining peripheral autologous tolerance to antigens. Treg needs IL-2 to perform its function, develop and induce its inhibitory characteristics.

As used herein, the term "binding ability" refers to the binding or interaction exhibited between paired molecules. The common paired molecules include ligand and receptor, antigen and antibody, enzyme and substrate, etc., more specifically, for example, IL2 and IL-2Rβγ subunit complex, or IL-2 and IL-2Rαβγ subunit complex. The "binding ability" of the present disclosure can be detected by conventional methods in the art, including but not limited to ELISA or FACS.

DESCRIPTION OF THE FIGURES

FIG. 3 shows the expression level of human IL-2 receptor βγ protein in the CHO-K1 hIL-2Rβγ recombinant cell line (clone 2E6) detected by flow cytometry (FACS), wherein the IL-2 receptor β, γ antibodies were purchased from BioLegend; and the negative control refers to isotype control;

FIG. 4 shows the expression level of human IL-2 receptor αβγ protein in the CHO-K1 hIL-2Rαβγ recombinant cell line (clone 2D6) detected by flow cytometry (FACS), wherein the IL-2 receptor α, β, γ antibodies were purchased from BioLegend; and the negative control refers to the expression level of corresponding receptors in the parental CHO-K1 cells.

FIG. 5 shows the binding activity of IL-2 mutant protein to CHO-K1 IL-2 receptor αβγ and IL-2 receptor βγ recombinant cells detected by flow cytometry (FACS);

FIG. 6 shows the effect of IL-2 mutant protein on the level of STAT5 phosphorylation in Tregs (FIGS. 6A-6C), CD4$^+$CD25$^-$FoxP3$^-$ T cells (FIGS. 6D-6F) and CD8$^+$ T cells (FIGS. 6G-6I);

FIG. 7 shows the effect of IL-2 mutant protein on the level of proliferation of Tregs (FIGS. 7A-7B), CD4$^+$CD25$^-$FoxP3$^-$T cells (FIGS. 7C-7D), and CD8$^+$CD25$^-$T cells (FIGS. 7E-7F);

DETAILED DESCRIPTION

Figure 1:
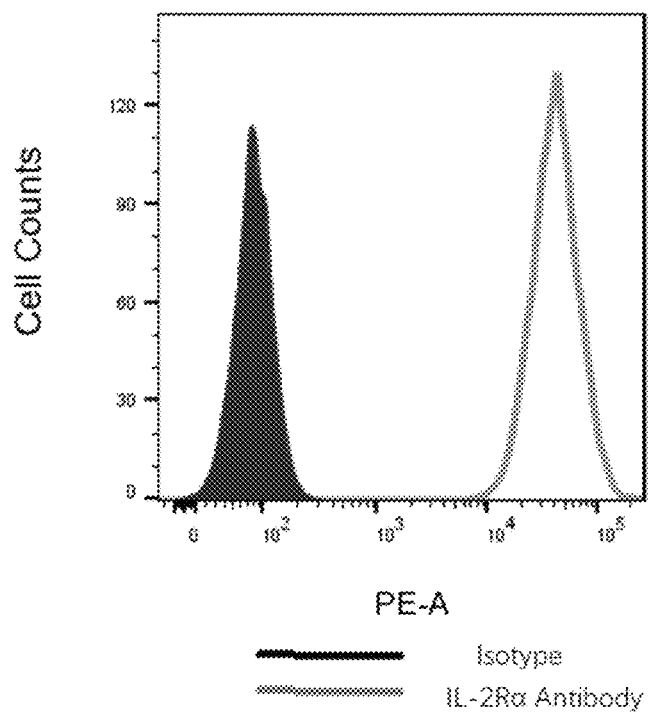
FIG. 1 shows the expression level of human IL-2 receptor α protein in the CHO-K1 hIL-2-Rα recombinant cell line (clone 1A6) detected by flow cytometry (FACS), wherein the IL-2 receptor α antibody is purchased from BioLegend; and the negative control refers to isotype control.

The present disclosure will be further described below with reference to specific examples. The advantages and features of the present disclosure will become clear with the description. If specific conditions are not indicated in the examples, the conventional conditions or the conditions suggested by the manufacturer shall be followed. If the manufacturer is not indicated, the reagents or instruments used are conventional products that can be purchased commercially.

The following examples of this disclosure are merely exemplary and not intended to limit the scope of the present disclosure. It should be understood by those skilled in the art that the details and forms of the technical solution of the present disclosure can be modified or substituted without departing from or exceeding the spirit or scope of the disclosure, and such modifications and substitutions all fall within the protection scope of the present disclosure.

Example 1—Design of IL-2 Mutants with Improved Thermal Stability and Construction of Expression Plasmid Various algorithms were used to obtain IL-2 mutants with improved thermal stability, and corresponding sequences were designed and synthesized. The nucleic acid fragments encoding wild-type IL-2 and the aforementioned IL-2 mutants were cloned into a pTT5 vector with an Fc tag, and then the plasmids encoding the following fusion proteins were prepared according to established standard methods in molecular biology: IL-2-linker2-hFc, mut0.08-linker2-hFc, mut0.31-linker2-hFc, mut0.36-linker2-hFc, mut0.39-linker2-hFc, mut0.46-linker2-hFc, mut0.57-linker2-hFc, mut0.66-linker2-hFc and mut0.68-linker2-hFc.

The specific sequences of the aforementioned fusion proteins and components are shown in Table 1, wherein "IL-2" represents the wild-type IL-2, and "mutXX" represents IL-2 mutants in which mutation occurs compared to wild-type IL-2.

TABLE 1

Sequences of IL-2 mutants with improved stability

| Mutant | SEQ ID NO | Sequence information |
|---|---|---|
| IL2 | SEQ ID NO: 1 | APTSSSTKKTQLQLEHLLLDLQMILNGINNYKNPKLTRMLTFKFYMPK KATELKHLQCLEEELKPLEEVLNLAQSKNFHLRPRDLISNINVIVLELK GSETTFMCEYADETATIVEFLNRWITFAQSIISTLT |
| mut0.08 (Y31V/A73L/H79Q) | SEQ ID NO: 2 | APTSSSTKKTQLQLEHLLLDLQMILNGINN<u>V</u>KNPKLTRMLTFKFYMPK KATELKHLQCLEEELKPLEEVLNL<u>L</u>QSKNF<u>Q</u>LRPRDLISNINVIVLELK GSETTFMCEYADETATIVEFLNRWITFAQSIISTLT |
| mut0.31 (Q13L) | SEQ ID NO: 3 | APTSSSTKKTQL<u>L</u>LEHLLLDLQMILNGINNYKNPKLTRMLTFKFYMPK KATELKHLQCLE<u>E</u>ELKPLEEVLNLAQSKNFHLRPRDLISNINVIVLELK GSETTFMCEYADETATIVEFLNRWITFAQSIISTLT |
| mut0.36 (R120F) | SEQ ID NO: 4 | APTSSSTKKTQLQLEHLLLDLQMILNGINNYKNPKLTRMLTFKFYMPK KATELKHLQCLEEELKPLEEVLNLAQSKNFHLRPRDLISNINVIVLELK GSETTFMCEYADETATIVEFLN<u>F</u>WITFAQSIISTLT |
| mut0.39 (L18I/V91A/F117W) | SEQ ID NO: 5 | APTSSSTKKTQLQLEHL<u>I</u>LDLQMILNGINNYKNPKLTRMLTFKFYMPK KATELKHLQCLEEELKPLEEVLNLAQSKNFHLRPRDLISNIN<u>A</u>IVLELK GSETTFMCEYADETATIVE<u>W</u>LNRWITFAQSIISTLT |
| mut0.46 (L18I/I89L/V93I) | SEQ ID NO: 6 | APTSSSTKKTQLQLEHL<u>I</u>LDLQMILNGINNYKNPKLTRMLTFKFYMPK KATELKHLQCLEEELKPLEEVLNLAQSKNFHLRPRDLISN<u>L</u>NVI<u>I</u>LELK GSETTFMCEYADETATIVEFLNRWITFAQSIISTLT |
| mut0.57 (G27W/R120F) | SEQ ID NO: 7 | APTSSSTKKTQLQLEHLLLDLQMILN<u>W</u>INNYKNPKLTRMLTFKFYMPK KATELKHLQCLEEELKPLEEVLNLAQSKNFHLRPRDLISNINVIVLELK GSETTFMCEYADETATIVEFLN<u>F</u>WITFAQSIISTLT |
| mut0.66 (P82L/R120F) | SEQ ID NO: 8 | APTSSSTKKTQLQLEHLLLDLQMILNGINNYKNPKLTRMLTFKFYMPK KATELKHLQCLEEELKPLEEVLNLAQSKNFHL<u>R</u>LRDLISNINVIVLELK GSETTFMCEYADETATIVEFLN<u>F</u>WITFAQSIISTLT |

TABLE 1-continued

Sequences of IL-2 mutants with improved stability

| Mutant | SEQ ID NO | Sequence information |
|---|---|---|
| mut0.68 (N90Y/R120F) | SEQ ID NO: 9 | APTSSSTKKTQLQLEHLLLDLQMILNGINNYKNPKLTRMLTFKFYMPK KATELKHLQCLEEELKPLEEVLNLAQSKNFHLRPRDLISNIYVIVLELK GSETTFMCEYADETATIVEFLNFWITFAQSIISTLT |
| linker2 | SEQ ID NO: 10 | GGGGSGGGGSGGGGS |
| hFc (C220S/N297G) | SEQ ID NO: 11 | EPKSSDKTHTCPPCPAPELLGGPSVFLFPPKPKDTLMISRTPEVTCVVV DVSHEDPEVKFNWYVDGVEVHNAKTKPREEQYGSTYRVVSVLTVLH QDWLNGKEYKCKVSNKALPAPIEKTISKAKGQPREPQVYTLPPSRDEL TKNQVSLTCLVKGFYPSDIAVEWESNGQPENNYKTTPPVLDSDGSFFL YSKLTVDKSRWQQGNVFSCSVMHEALHNHYTQKSLSLSPGK |
| IL2-linker2-hFc, also known as WT IL-2-linker2-hFc (C220S/N297G) | SEQ ID NO: 12 | APTSSSTKKTQLQLEHLLLDLQMILNGINNYKNPKLTRMLTFKFYMPK KATELKHLQCLEEELKPLEEVLNLAQSKNFHLRPRDLISNINIVIVLELK GSETTFMCEYADETATIVEFLNRWITFAQSIISTLTGGGGSGGGGSGG GGSEPKSSDKTHTCPPCPAPELLGGPSVFLFPPKPKDTLMISRTPEVTC VVVDVSHEDPEVKFNWYVDGVEVHNAKTKPREEQYGSTYRVVSVLT VLHQDWLNGKEYKCKVSNKALPAPIEKTISKAKGQPREPQVYTLPPSR DELTKNQVSLTCLVKGFYPSDIAVEWESNGQPENNYKTTPPVLDSDGS FFLYSKLTVDKSRWQQGNVFSCSVMHEALHNHYTQKSLSLSPGK |
| mut0.08-linker2-hFc (Y31V/A73L/H79Q) | SEQ ID NO: 13 | APTSSSTKKTQLQLEHLLLDLQMILNGINNVKNPKLTRMLTFKFYMPK KATELKHLQCLEEELKPLEEVLNLLQSKNFQLRPRDLISNINIVIVLELK GSETTFMCEYADETATIVEFLNRWITFAQSIISTLTGGGGSGGGGSGG GGSEPKSSDKTHTCPPCPAPELLGGPSVFLFPPKPKDTLMISRTPEVTC VVVDVSHEDPEVKFNWYVDGVEVHNAKTKPREEQYGSTYRVVSVLT VLHQDWLNGKEYKCKVSNKALPAPIEKTISKAKGQPREPQVYTLPPSR DELTKNQVSLTCLVKGFYPSDIAVEWESNGQPENNYKTTPPVLDSDGS FFLYSKLTVDKSRWQQGNVFSCSVMHEALHNHYTQKSLSLSPGK |
| mut0.31-linker2-hFc (Q13L) | SEQ ID NO: 14 | APTSSSTKKTQLLLEHLLLDLQMILNGINNYKNPKLTRMLTFKFYMPK KATELKHLQCLEEELKPLEEVLNLAQSKNFHLRPRDLISNINIVIVLELK GSETTFMCEYADETATIVEFLNRWITFAQSIISTLTGGGGSGGGGSGG GGSEPKSSDKTHTCPPCPAPELLGGPSVFLFPPKPKDTLMISRTPEVTC VVVDVSHEDPEVKFNWYVDGVEVHNAKTKPREEQYGSTYRVVSVLT VLHQDWLNGKEYKCKVSNKALPAPIEKTISKAKGQPREPQVYTLPPSR DELTKNQVSLTCLVKGFYPSDIAVEWESNGQPENNYKTTPPVLDSDGS FFLYSKLTVDKSRWQQGNVFSCSVMHEALHNHYTQKSLSLSPGK |
| mut0.36-linker2-hFc (R120F) | SEQ ID NO: 15 | APTSSSTKKTQLQLEHLLLDLQMILNGINNYKNPKLTRMLTFKFYMPK KATELKHLQCLEEELKPLEEVLNLAQSKNFHLRPRDLISNINIVIVLELK GSETTFMCEYADETATIVEFLNFWITFAQSIISTLTGGGGSGGGGSGG GGSEPKSSDKTHTCPPCPAPELLGGPSVFLFPPKPKDTLMISRTPEVTC VVVDVSHEDPEVKFNWYVDGVEVHNAKTKPREEQYGSTYRVVSVLT VLHQDWLNGKEYKCKVSNKALPAPIEKTISKAKGQPREPQVYTLPPSR DELTKNQVSLTCLVKGFYPSDIAVEWESNGQPENNYKTTPPVLDSDGS FFLYSKLTVDKSRWQQGNVFSCSVMHEALHNHYTQKSLSLSPGK |
| mut0.39-linker2-hFc (L18I/V91A/F117W) | SEQ ID NO: 16 | APTSSSTKKTQLQLEHLILDLQMILNGINNYKNPKLTRMLTFKFYMPK KATELKHLQCLEEELKPLEEVLNLAQSKNFHLRPRDLISNINAIVLELK GSETTFMCEYADETATIVEWLNRWITFAQSIISTLTGGGGSGGGGSGG GGSEPKSSDKTHTCPPCPAPELLGGPSVFLFPPKPKDTLMISRTPEVTC VVVDVSHEDPEVKFNWYVDGVEVHNAKTKPREEQYGSTYRVVSVLT VLHQDWLNGKEYKCKVSNKALPAPIEKTISKAKGQPREPQVYTLPPSR DELTKNQVSLTCLVKGFYPSDIAVEWESNGQPENNYKTTPPVLDSDGS FFLYSKLTVDKSRWQQGNVFSCSVMHEALHNHYTQKSLSLSPGK |
| mut0.46-linker2-hFc (L18I/I89L/V93I) | SEQ ID NO: 17 | APTSSSTKKTQLQLEHLILDLQMILNGINNYKNPKLTRMLTFKFYMPK KATELKHLQCLEEELKPLEEVLNLAQSKNFHLRPRDLISNLNVIILELK GSETTFMCEYADETATIVEFLNRWITFAQSIISTLTGGGGSGGGGSGG GGSEPKSSDKTHTCPPCPAPELLGGPSVFLFPPKPKDTLMISRTPEVTC VVVDVSHEDPEVKFNWYVDGVEVHNAKTKPREEQYGSTYRVVSVLT VLHQDWLNGKEYKCKVSNKALPAPIEKTISKAKGQPREPQVYTLPPSR DELTKNQVSLTCLVKGFYPSDIAVEWESNGQPENNYKTTPPVLDSDGS FFLYSKLTVDKSRWQQGNVFSCSVMHEALHNHYTQKSLSLSPGK |
| mut0.57-linker2-hFc (G27W/R120F) | SEQ ID NO: 18 | APTSSSTKKTQLQLEHLLLDLQMILNWINNYKNPKLTRMLTFKFYMPK KATELKHLQCLEEELKPLEEVLNLAQSKNFHLRPRDLISNINIVIVLELK GSETTFMCEYADETATIVEFLNFWITFAQSIISTLTGGGGSGGGGSGG GGSEPKSSDKTHTCPPCPAPELLGGPSVFLFPPKPKDTLMISRTPEVTC VVVDVSHEDPEVKFNWYVDGVEVHNAKTKPREEQYGSTYRVVSVLT VLHQDWLNGKEYKCKVSNKALPAPIEKTISKAKGQPREPQVYTLPPSR DELTKNQVSLTCLVKGFYPSDIAVEWESNGQPENNYKTTPPVLDSDGS FFLYSKLTVDKSRWQQGNVFSCSVMHEALHNHYTQKSLSLSPGK |

TABLE 1-continued

Sequences of IL-2 mutants with improved stability

| Mutant | SEQ ID NO | Sequence information |
|---|---|---|
| mut0.66-linker2-hFc (P82L/R120F) | SEQ ID NO: 19 | APTSSSTKKTQLQLEHLLLDLQMILNGINNYKNPKLTRMLTFKFYMPK KATELKHLQCLEEELKPLEEVLNLAQSKNFHLRLRDLISNINVIVLELK GSETTFMCEYADETATIVEFLNFWITFAQSIISTLTGGGGSGGGGSGG GGSEPKSSDKTHTCPPCPAPELLGGPSVFLFPPKPKDTLMISRTPEVTC VVVDVSHEDPEVKFNWYVDGVEVHNAKTKPREEQYGSTYRVVSVLT VLHQDWLNGKEYKCKVSNKALPAPIEKTISKAKGQPREPQVYTLPPSR DELTKNQVSLTCLVKGFYPSDIAVEWESNGQPENNYKTTPPVLDSDGS FFLYSKLTVDKSRWQQGNVFSCSVMHEALHNHYTQKSLSLSPGK |
| mut0.68-linker2-hFc (N90Y/R120F) | SEQ ID NO: 20 | APTSSSTKKTQLQLEHLLLDLQMILNGINNYKNPKLTRMLTFKFYMPK KATELKHLQCLEEELKPLEEVLNLAQSKNFHLRPRDLISNIYVIVLELK GSETTFMCEYADETATIVEFLNFWITFAQSIISTLTGGGGSGGGGSGG GGSEPKSSDKTHTCPPCPAPELLGGPSVFLFPPKPKDTLMISRTPEVTC VVVDVSHEDPEVKFNWYVDGVEVHNAKTKPREEQYGSTYRVVSVLT VLHQDWLNGKEYKCKVSNKALPAPIEKTISKAKGQPREPQVYTLPPSR DELTKNQVSLTCLVKGFYPSDIAVEWESNGQPENNYKTTPPVLDSDGS FFLYSKLTVDKSRWQQGNVFSCSVMHEALHNHYTQKSLSLSPGK |

Example 2—Production and Purification of IL-2 Mutants with Improved Thermal Stability HEK293 cells (purchased from the Cell Bank of the Chinese Academy of Sciences) were transiently transfected (PEI, Polysciences) with the plasmids constructed in Example 1 and then expanded at 37° C. in FreeStyle™ 293 Expression Medium (purchased from Gibco). After 7 days, the cell culture medium was collected, and the cell components were removed by centrifugation to obtain the culture supernatant containing IL-2-hFc fusion proteins.

The fusion proteins in the cell culture supernatant were purified using a 10 mL protein A column (purchased from Bestchrom). The protein A column was first equilibrated with 3 to 5 column volumes of an equilibrium buffer (PBS phosphate buffer, pH 7.4), and then loaded with the clear culture supernatant at a flow rate of 10 mL/min. After loading, the protein A column was washed with 3 to 5 column volumes of the equilibrium buffer. The proteins bound to the protein A column were eluted with an eluent buffer (0.02 M citric acid buffer, 0.1 M glycine, 0.1 M sodium chloride, pH 3.0), and the elution was monitored by a nucleic acid/protein detector (A280 ultraviolet absorption peak). The eluted proteins were collected and neutralized with the added buffer (1 M arginine, 0.4 M succinic acid, pH 9.0). The target proteins were then collected through a molecular sieve (purchased from Bestchrom) with a buffer system (20 mM PB, 200 mM sodium chloride, pH 6.0-6.5). The purified IL-2 mutant fusion proteins were obtained by aseptic filtration with a 0.22 m filter and preserved in sterile condition.

The purified IL-2 mutant fusion proteins were tested and analyzed for protein yield, concentration (A280/1.4) and SEC purity. The purified IL-2 mutant fusion proteins with improved thermal stability (mutXX-linker2-hFc) were qualified, and had a significantly higher yield compared to wild-type IL-2 (IL2-linker2-hFc). The results of protein yield, concentration and purity are shown in Table 2.

TABLE 2

Detection results of IL-2 mutant fusion proteins with improved thermal stability

| Mutant | Protein yield (mg/L) | Protein SEC purity | Protein concentration (mg/ml) |
|---|---|---|---|
| IL-2-linker2-hFc | 0.95 | 97.25% | 1.11 |
| mut0.08-linker2-hFc | 8.95 | 99.85% | 1.79 |
| mut0.31-linker2-hFc | 1.54 | 98.49% | 2.20 |
| mut0.36-linker2-hFc | 2.98 | 99.99% | 1.49 |
| mut0.39-linker2-hFc | 43.10 | 99.58% | 2.13 |
| mut0.46-linker2-hFc | 13.82 | 99.92% | 1.22 |
| mut0.57-linker2-hFc | 1.25 | 99.91% | 0.89 |
| mut0.66-linker2-hFc | 7.39 | 99.90% | 1.12 |
| mut0.68-linker2-hFc | 11.90 | 99.99% | 1.19 |

Example 3—Differential Scanning Fluorimetry (DSF) Assay of IL-2 Mutants with Improved Thermal Stability The buffer in Protein Thermal Shift Dye Kit (purchased from Applied Biosystems, Cat. No. 4461146) diluted to 50 times, the IL-2 mutant proteins (purified by the method described in Example 2) diluted to 0.5 mg/mL, and the dye diluted to 2 times were added to a 20 μL reaction system. After being mixed evenly, the mixture was added into 8-tube strips with 2 duplicate tubes for each sample. The tubes were covered, centrifuged for 5-10 seconds, and analyzed by the Applied Biosystems 7500. The Tm values were then obtained by using Boltzmann method to analyze the melting curve. As shown in Table 3, compared to wild-type IL-2 (IL2-linker2-hFc), the IL-2 mutants (mutXX-linker2-hFc) had increased Tm values by more than 3° C., and thus had significantly improved thermal stability.

TABLE 3

DSF assay results of IL-2 mutants with improved thermal stability

| Mutant | Tm (° C.) |
|---|---|
| IL-2-linker2-hFc | 46.74 |
| mut0.08-linker2-hFc | 54.91 |
| mut0.31-linker2-hFc | 57.53 |
| mut0.36-linker2-hFc | 56.59 |

TABLE 3-continued

DSF assay results of IL-2 mutants with improved thermal stability

| Mutant | Tm (° C.) |
|---|---|
| mut0.39-linker2-hFc | 55.93 |
| mut0.46-linker2-hFc | 53.83 |
| mut0.57-linker2-hFc | 57.98 |
| mut0.66-linker2-hFc | 57.24 |
| mut0.68-linker2-hFc | 54.77 |

Example 4—Design of IL-2 Mutants (IL-2 Mutants with Decreased Binding Ability to βγ Subunits and IL-2 Mutants with Decreased Binding Ability to βγ Subunits and with Improved Thermal Stability) and Construction of Expression Plasmid Various algorithms including MOE software were used to simulate the interaction interface between human IL-2 and corresponding receptor α, β, and γ subunits to obtain mutation sites having decreased binding ability to βγ subunits. The IL-2 mutant sequences with mutation sites having decreased binding activities to βγ subunits were designed and synthesized, together with the IL-2 mutant sequences with a combination of such mutation sites with mutation sites having improved thermal stability. The nucleic acid fragments encoding wild-type IL-2 and the aforementioned IL-2 mutants were cloned into a pTT5 vector with an Fc tag, and then the plasmids encoding the following fusion proteins were prepared according to established standard methods in molecular biology: IL-2-linker2-hFc, mut7-linker2-hFc, mut7.08-linker2-hFc, mut7.36-linker2-hFc, mut7.39-linker2-hFc, mut7.46-linker2-hFc, mut7.57-linker2-hFc, mut7.66-linker2-hFc, mut8-linker2-hFc, mut8.08-linker2-hFc, mut8.36-linker2-hFc, mut11-linker2-hFc, mut11.08-linker2-hFc, mut11.31-linker2-hFc, mut11.36-linker2-hFc, mut11.46-linker2-hFc, mut61-linker2-hFc, mut61.08-linker2-hFc and mut61.46-linker2-hFc. The specific sequences of the fusion proteins and components thereof are shown in Table 4, where "IL-2" represents wild-type IL-2 and "mutXX" represents IL-2 mutants in which mutation occurs compared to the wild-type IL-2.

TABLE 4

Sequences of IL-2 mutants

| Mutant | SEQ ID NO | Sequence information |
|---|---|---|
| IL2 | SEQ ID NO: 1 | Shown in Table 1 |
| mut7 (H16E) | SEQ ID NO: 21 | APTSSSTKKTQLQLEELLLDLQMILNGINNYKNPKLTRMLTFKFYM PKKATELKHLQCLEEELKPLEEVLNLAQSKNFHLRPRDLISNINVIV LELKGSETTFMCEYADETATIVEFLNRWITFAQSIISTLT |
| mut7.08 (H16E/Y31V/A73L/H79Q) | SEQ ID NO: 22 | APTSSSTKKTQLQLEELLLDLQMILNGINNVKNPKLTRMLTFKFYMPK KATELKHLQCLEEELKPLEEVLNLLQSKNFQLRPRDLISNINVIVLELK GSETTFMCEYADETATIVEFLNRWITFAQSIISTLT |
| mut7.36 (H16E/R120F) | SEQ ID NO: 23 | APTSSSTKKTQLQLEELLLDLQMILNGINNYKNPKLTRMLTFKFYM PKKATELKHLQCLEEELKPLEEVLNLAQSKNFHLRPRDLISNINVIV LELKGSETTFMCEYADETATIVEFLNFWITFAQSIISTLT |
| mut7.39 (H16E/L18I/V91A/F117W) | SEQ ID NO: 24 | APTSSSTKKTQLQLEELILDLQMILNGINNYKNPKLTRMLTFKFYMP KKATELKHLQCLEEELKPLEEVLNLAQSKNFHLRPRDLISNINAIVL ELKGSETTFMCEYADETATIVEWLNRWITFAQSIISTLT |
| mut7.46 (H16E/L18I/I89L/V93I) | SEQ ID NO: 25 | APTSSSTKKTQLQLEELILDLQMILNGINNYKNPKLTRMLTFKFYMP KKATELKHLQCLEEELKPLEEVLNLAQSKNFHLRPRDLISNLNVIIL ELKGSETTFMCEYADETATIVEFLNRWITFAQSIISTLT |
| mut7.57 (H16E/G27W/R120F) | SEQ ID NO: 26 | APTSSSTKKTQLQLEELLLDLQMILNWINNYKNPKLTRMLTFKFYMPK KATELKHLQCLEEELKPLEEVLNLAQSKNFHLRPRDLISNINVIVLELK GSETTFMCEYADETATIVEFLNFWITFAQSIISTLT |
| mut7.66 (H16E/P82L/R120F) | SEQ ID NO: 27 | APTSSSTKKTQLQLEELLLDLQMILNGINNYKNPKLTRMLTFKFYM PKKATELKHLQCLEEELKPLEEVLNLAQSKNFHLRLRDLISNINVIV LELKGSETTFMCEYADETATIVEFLNFWITFAQSIISTLT |
| mut8 (D20A) | SEQ ID NO: 28 | APTSSSTKKTQLQLEHLLLALQMILNGINNYKNPKLTRMLTFKFYMPK KATELKHLQCLEEELKPLEEVLNLAQSKNFHLRPRDLISNINVIVLELK GSETTFMCEYADETATIVEFLNRWITFAQSIISTLT |
| mut8.08 (D20A/Y31V/A73L/H79) | SEQ ID NO: 29 | APTSSSTKKTQLQLEHLLLALQMILNGINNVKNPKLTRMLTFKFYMPK KATELKHLQCLEEELKPLEEVLNLLQSKNFQLRPRDLISNINVIVLELK GSETTFMCEYADETATIVEFLNRWITFAQSIISTLT |
| mut8.36 (D20A/R120F) | SEQ ID NO: 30 | APTSSSTKKTQLQLEHLLLALQMILNGINNYKNPKLTRMLTFKFYMPK KATELKHLQCLEEELKPLEEVLNLAQSKNFHLRPRDLISNINVIVLELK GSETTFMCEYADETATIVEFLNFWITFAQSIISTLT |
| mut11 (V91R) | SEQ ID NO: 31 | APTSSSTKKTQLQLEHLLLDLQMILNGINNYKNPKLTRMLTFKFYM PKKATELKHLQCLEEELKPLEEVLNLAQSKNFHLRPRDLISNINRIV LELKGSETTFMCEYADETATIVEFLNRWITFAQSIISTLT |

TABLE 4-continued

Sequences of IL-2 mutants

| Mutant | SEQ ID NO | Sequence information |
|---|---|---|
| mut11.08 (V91R/Y31V/A73L/H79) | SEQ ID NO: 32 | APTSSSTKKTQLQLEHLLLDLQMILNGINNVKNPKLTRMLTFKFYM PKKATELKHLQCLEEELKPLEEVLNLLQSKNFQLRPRDLISNINRIV LELKGSETTFMCEYADETATIVEFLNRWITFAQSIISTLT |
| mut11.31 (V91R/Q13L) | SEQ ID NO: 33 | APTSSSTKKTQLLLEHLLLDLQMILNGINNYKNPKLTRMLTFKFYM PKKATELKHLQCLEEELKPLEEVLNLAQSKNFHLRPRDLISNINRIV LELKGSETTFMCEYADETATIVEFLNRWITFAQSIISTLT |
| mut11.36 (V91R/R120F) | SEQ ID NO: 34 | APTSSSTKKTQLQLEHLLLDLQMILNGINNYKNPKLTRMLTFKFYMPK KATELKHLQCLEEELKPLEEVLNLAQSKNFHLRPRDLISNINRIVLELK GSETTFMCEYADETATIVEFLNFWITFAQSIISTLT |
| mut11.46 (V91R/L18I/I89L/V93I) | SEQ ID NO: 35 | APTSSSTKKTQLQLEHLILDLQMILNGINNYKNPKLTRMLTFKFYMP KKATELKHLQCLEEELKPLEEVLNLAQSKNFHLRPRDLISNLNRIIL ELKGSETTFMCEYADETATIVEFLNRWITFAQSIISTLT |
| mut61 (H16E/V91R) | SEQ ID NO: 36 | APTSSSTKKTQLQLEELLLDLQMILNGINNYKNPKLTRMLTFKFYM PKKATELKHLQCLEEELKPLEEVLNLAQSKNFHLRPRDLISNINRIV LELKGSETTFMCEYADETATIVEFLNRWITFAQSIISTLT |
| mut61.08 (H16E/V91R/Y31V/A73L/H79Q) | SEQ ID NO: 37 | APTSSSTKKTQLQLEELLLDLQMILNGINNYKNPKLTRMLTFKFYM PKKATELKHLQCLEEELKPLEEVLNLLQSKNFQLRPRDLISNINRIV LELKGSETTFMCEYADETATIVEFLNRWITFAQSIISTLT |
| mut61.46 (H16E/V91R/L18I/I89L/V93I) | SEQ ID NO: 38 | APTSSSTKKTQLQLEELILDLQMILNGINNYKNPKLTRMLTFKFYMP KKATELKHLQCLEEELKPLEEVLNLAQSKNFHLRPRDLISNLNRIIL ELKGSETTFMCEYADETATIVEFLNRWITFAQSIISTLT |
| linker2 | SEQ ID NO: 10 | Shown in Table 1 |
| hFc (C220S/N297G) | SEQ ID NO: 11 | Shown in Table 1 |
| IL2-linker2-hFc | SEQ ID NO: 12 | Shown in Table 1 |
| mut7-linker2-hFc (H16E) | SEQ ID NO: 39 | APTSSSTKKTQLQLEELLLDLQMILNGINNYKNPKLTRMLTFKFYM PKKATELKHLQCLEEELKPLEEVLNLAQSKNFHLRPRDLISNINVIV LELKGSETTFMCEYADETATIVEFLNRWITFAQSIISTLTGGGGSGG GGSGGGGSEPKSSDKTHTCPPCPAPELLGGPSVFLFPPKPKDTLMISRT PEVTCVVVDVSHEDPEVKFNWYVDGVEVHNAKTKPREEQYGSTYRV VSVLTVLHQDWLNGKEYKCKVSNKALPAPIEKTISKAKGQPREPQVYT LPPSRDELTKNQVSLTCLVKGFYPSDIAVEWESNGQPENNYKTTPPVL DSDGSFFLYSKLTVDKSRWQQGNVFSCSVMHEALHNHYTQKSLSLSP GK |
| mut7.08-linker2-hFc (H16E/Y31V/A73L/H79Q) | SEQ ID NO: 40 | APTSSSTKKTQLQLEELLLDLQMILNGINNVKNPKLTRMLTFKFYMPK KATELKHLQCLEEELKPLEEVLNLLQSKNFQLRPRDLISNINVIVLELK GSETTFMCEYADETATIVEFLNRWITFAQSIISTLTGGGGSGGGGSGG GGSEPKSSDKTHTCPPCPAPELLGGPSVFLFPPKPKDTLMISRTPEVTCV VVDVSHEDPEVKFNWYVDGVEVHNAKTKPREEQYGSTYRVVSLTV LHQDWLNGKEYKCKVSNKALPAPIEKTISKAKGQPREPQVYTLPPSRD ELTKNQVSLTCLVKGFYPSDIAVEWESNGQPENNYKTTPPVLDSDGSF FLYSKLTVDKSRWQQGNVFSCSVMHEALHNHYTQKSLSLSPGK |
| mut7.36-linker2-hFc (H16E/R120F) | SEQ ID NO: 41 | APTSSSTKKTQLQLEELLLDLQMILNGINNYKNPKLTRMLTFKFYM PKKATELKHLQCLEEELKPLEEVLNLAQSKNFHLRPRDLISNINVIV LELKGSETTFMCEYADETATIVEFLNFWITFAQSIISTLTGGGGSGG GGSGGGGSEPKSSDKTHTCPPCPAPELLGGPSVFLFPPKPKDTLMIS RTPEVTCVVVDVSHEDPEVKFNWYVDGVEVHNAKTKPREEQYGS TYRVVSVLTVLHQDWLNGKEYKCKVSNKALPAPIEKTISKAKGQP REPQVYTLPPSRDELTKNQVSLTCLVKGFYPSDIAVEWESNGQPEN NYKTTPPVLDSDGSFFLYSKLTVDKSRWQQGNVFSCSVMHEALHN HYTQKSLSLSPGK |
| mut7.39-linker2-hFc (H16E/L18I/V91A/F117W) | SEQ ID NO: 42 | APTSSSTKKTQLQLEELILDLQMILNGINNYKNPKLTRMLTFKFYMP KKATELKHLQCLEEELKPLEEVLNLAQSKNFHLRPRDLISNINAIVL ELKGSETTFMCEYADETATIVEWLNRWITFAQSIISTLTGGGGSGG GGSGGGGSEPKSSDKTHTCPPCPAPELLGGPSVFLFPPKPKDTLMIS RTPEVTCVVVDVSHEDPEVKFNWYVDGVEVHNAKTKPREEQYGS TYRVVSVLTVLHQDWLNGKEYKCKVSNKALPAPIEKTISKAKGQP REPQVYTLPPSRDELTKNQVSLTCLVKGFYPSDIAVEWESNGQPEN NYKTTPPVLDSDGSFFLYSKLTVDKSRWQQGNVFSCSVMHEALHN HYTQKSLSLSPGK |

TABLE 4-continued

Sequences of IL-2 mutants

| Mutant | SEQ ID NO | Sequence information |
|---|---|---|
| mut7.46-linker2-hFc (H16E/L18I/I89L/V93I) | SEQ ID NO: 43 | APTSSSTKKTQLQLEEELILDLQMILNGINNYKNPKLTRMLTFKFYMP KKATELKHLQCLEEELKPLEEVLNLAQSKNFHLRPRDLISNLNVIIL ELKGSETTFMCEYADETATIVEFLNRWITFAQSIISTLTGGGGSGGG GSGGGGGSEPKSSDKTHTCPPCPAPELLGGPSVFLFPPKPKDTLMISR TPEVTCVVVDVSHEDPEVKFNWYVDGVEVHNAKTKPREEQYGST YRVVSVLTVLHQDWLNGKEYKCKVSNKALPAPIEKTISKAKGQPR EPQVYTLPPSRDELTKNQVSLTCLVKGFYPSDIAVEWESNGQPENN YKTTPPVLDSDGSFFLYSKLTVDKSRWQQGNVFSCSVMHEALHNH YTQKSLSLSPGK |
| mut7.57-linker2-hFc (H16E/G27W/R120F) | SEQ ID NO: 44 | APTSSSTKKTQLQLEEELLLDLQMILNWINNYKNPKLTRMLTFKFYMPK KATELKHLQCLEEELKPLEEVLNLAQSKNFHLRPRDLISNINVIVLELK GSETTFMCEYADETATIVEFLNFWITFAQSIISTLTGGGGSGGGGSGG GGSEPKSSDKTHTCPPCPAPELLGGPSVFLFPPKPKDTLMISRTPEVTCV VVDVSHEDPEVKFNWYVDGVEVHNAKTKPREEQYGSTYRVVSVLTV LHQDWLNGKEYKCKVSNKALPAPIEKTISKAKGQPREPQVYTLPPSRD ELTKNQVSLTCLVKGFYPSDIAVEWESNGQPENNYKTTPPVLDSDGSF FLYSKLTVDKSRWQQGNVFSCSVMHEALHNYTQKSLSLSPGK |
| mut7.66-linker2-hFc (H16E/P82L/R120F) | SEQ ID NO: 45 | APTSSSTKKTQLQLEEELLLDLQMILNGINNYKNPKLTRMLTFKFYM PKKATELKHLQCLEEELKPLEEVLNLAQSKNFHLRLRDLISNINVIV LELKGSETTFMCEYADETATIVEFLNFWITFAQSIISTLTGGGGSGG GGSGGGGGSEPKSSDKTHTCPPCPAPELLGGPSVFLFPPKPKDTLMIS RTPEVTCVVVDVSHEDPEVKFNWYVDGVEVHNAKTKPREEQYGS TYRVVSVLTVLHQDWLNGKEYKCKVSNKALPAPIEKTISKAKGQP REPQVYTLPPSRDELTKNQVSLTCLVKGFYPSDIAVEWESNGQPEN NYKTTPPVLDSDGSFFLYSKLTVDKSRWQQGNVFSCSVMHEALHN HYTQKSLSLSPGK |
| mut8-linker2-hFc (D20A) | SEQ ID NO: 46 | APTSSSTKKTQLQLEHLLLALQMILNGINNYKNPKLTRMLTFKFYMPK KATELKHLQCLEEELKPLEEVLNLAQSKNFHLRPRDLISNINVIVLELK GSETTFMCEYADETATIVEFLNRWITFAQSIISTLTGGGGSGGGGSGG GGSEPKSSDKTHTCPPCPAPELLGGPSVFLFPPKPKDTLMISRTPEVT CVVVDVSHEDPEVKFNWYVDGVEVHNAKTKPREEQYGSTYRVVS VLTVLHQDWLNGKEYKCKVSNKALPAPIEKTISKAKGQPREPQVYT LPPSRDELTKNQVSLTCLVKGFYPSDIAVEWESNGQPENNYKTTPP VLDSDGSFFLYSKLTVDKSRWQQGNVFSCSVMHEALHNYTQKSL SLSPGK |
| mut8.08-linker2-hFc (D20A/Y31V/A73L/H79Q) | SEQ ID NO: 47 | APTSSSTKKTQLQLEHLLLALQMILNGINNVKNPKLTRMLTFKFYMPK KATELKHLQCLEEELKPLEEVLNLLQSKNFQLRPRDLISNINVIVLELK GSETTFMCEYADETATIVEFLNWITFAQSIISTLTGGGGSGGGGSGG GGSEPKSSDKTHTCPPCPAPELLGGPSVFLFPPKPKDTLMISRTPEVT CVVVDVSHEDPEVKFNWYVDGVEVHNAKTKPREEQYGSTYRVVS VLTVLHQDWLNGKEYKCKVSNKALPAPIEKTISKAKGQPREPQVYT LPPSRDELTKNQVSLTCLVKGFYPSDIAVEWESNGQPENNYKTTPP VLDSDGSFFLYSKLTVDKSRWQQGNVFSCSVMHEALHNHYTQKSL SLSPGK |
| mut8.36-linker2-hFc (D20A/R120F) | SEQ ID NO: 48 | APTSSSTKKTQLQLEHLLLALQMILNGINNYKNPKLTRMLTFKFYMPK KATELKHLQCLEEELKPLEEVLNLAQSKNFHLRPRDLISNINVIVLELK GSETTFMCEYADETATIVEFLNFWITFAQSIISTLTGGGGSGGGGSGG GGSEPKSSDKTHTCPPCPAPELLGGPSVFLFPPKPKDTLMISRTPEVT CVVVDVSHEDPEVKFNWYVDGVEVHNAKTKPREEQYGSTYRVVS VLTVLHQDWLNGKEYKCKVSNKALPAPIEKTISKAKGQPREPQVYT LPPSRDELTKNQVSLTCLVKGFYPSDIAVEWESNGQPENNYKTTPP VLDSDGSFFLYSKLTVDKSRWQQGNVFSCSVMHEALHNYTQKSL SLSPGK |
| mut11-linker2-hFc (V91R) | SEQ ID NO: 49 | APTSSSTKKTQLQLEHLLLDLQMILNGINNYKNPKLTRMLTFKFYM PKKATELKHLQCLEEELKPLEEVLNLAQSKNFHLRPRDLISNINRIV LELKGSETTFMCEYADETATIVEFLNRWITFAQSIISTLTGGGGSGG GGSGGGGGSEPKSSDKTHTCPPCPAPELLGGPSVFLFPPKPKDTLMIS RTPEVTCVVVDVSHEDPEVKFNWYVDGVEVHNAKTKPREEQYGS TYRVVSVLTVLHQDWLNGKEYKCKVSNKALPAPIEKTISKAKGQP REPQVYTLPPSRDELTKNQVSLTCLVKGFYPSDIAVEWESNGQPEN NYKTTPPVLDSDGSFFLYSKLTVDKSRWQQGNVFSCSVMHEALHN HYTQKSLSLSPGK |
| mut11.08-linker2-hFc (V91R/Y31V/A73L/H79Q) | SEQ ID NO: 50 | APTSSSTKKTQLQLEHLLLDLQMILNGINNVKNPKLTRMLTFKFYM PKKATELKHLQCLEEELKPLEEVLNLLQSKNFQLRPRDLISNINRIV LELKGSETTFMCEYADETATIVEFLNRWITFAQSIISTLTGGGGSGG GGSGGGGGSEPKSSDKTHTCPPCPAPELLGGPSVFLFPPKPKDTLMIS RTPEVTCVVVDVSHEDPEVKFNWYVDGVEVHNAKTKPREEQYGS |

TABLE 4-continued

Sequences of IL-2 mutants

| Mutant | SEQ ID NO | Sequence information |
|---|---|---|
| | | TYRVVSVLTVLHQDWLNGKEYKCKVSNKALPAPIEKTISKAKGQP REPQVYTLPPSRDELTKNQVSLTCLVKGFYPSDIAVEWESNGQPEN NYKTTPPVLDSDGSFFLYSKLTVDKSRWQQGNVFSCSVMHEALHN HYTQKSLSLSPGK |
| mut11.31-linker2-hFc (V91R/Q13L) | SEQ ID NO: 51 | APTSSSTKKTQLLLEHLLLDLQMILNGINNYKNPKLTRMLTFKFYM PKKATELKHLQCLEEELKPLEEVLNLAQSKNFHLRPRDLISNINRIV LELKGSETTFMCEYADETATIVEFLNRWITFAQSIISTLTGGGGSGG GGSGGGGSEPKSSDKTHTCPPCPAPELLGGPSVFLFPPKPKDTLMIS RTPEVTCVVVDVSHEDPEVKFNWYVDGVEVHNAKTKPREEQYGS TYRVVSVLTVLHQDWLNGKEYKCKVSNKALPAPIEKTISKAKGQP REPQVYTLPPSRDELTKNQVSLTCLVKGFYPSDIAVEWESNGQPEN NYKTTPPVLDSDGSFFLYSKLTVDKSRWQQGNVFSCSVMHEALHN HYTQKSLSLSPGK |
| mut11.36-linker2-hFc (V91R/R120F) | SEQ ID NO: 52 | APTSSSTKKTQLQLEHLLLDLQMILNGINNYKNPKLTRMLTFKFYMPK KATELKHLQCLEEELKPLEEVLNLAQSKNFHLRPRDLISNINRIVLELK GSETTFMCEYADETATIVEFLNFWITFAQSIISTLTGGGGSGGGGSGG GGSEPKSSDKTHTCPPCPAPELLGGPSVFLFPPKPKDTLMISRTPEVTCV VVDVSHEDPEVKFNWYVDGVEVHNAKTKPREEQYGSTYRVVSVLTV LHQDWLNGKEYKCKVSNKALPAPIEKTISKAKGQPREPQVYTLPPSRD ELTKNQVSLTCLVKGFYPSDIAVEWESNGQPENNYKTTPPVLDSDGSF FLYSKLTVDKSRWQQGNVFSCSVMHEALHNHYTQKSLSLSPGK |
| mut11.46-linker2-hFc (V91R/L18I/I89L/V93I) | SEQ ID NO: 53 | APTSSSTKKTQLQLEHLILDLQMILNGINNYKNPKLTRMLTFKFYMP KKATELKHLQCLEEELKPLEEVLNLAQSKNFHLRPRDLISNLNRIIL ELKGSETTFMCEYADETATIVEFLNRWITFAQSIISTLTGGGGSGGG GSGGGGSEPKSSDKTHTCPPCPAPELLGGPSVFLFPPKPKDTLMISR TPEVTCVVVDVSHEDPEVKFNWYVDGVEVHNAKTKPREEQYGST YRVVSVLTVLHQDWLNGKEYKCKVSNKALPAPIEKTISKAKGQPR EPQVYTLPPSRDELTKNQVSLTCLVKGFYPSDIAVEWESNGQPENN YKTTPPVLDSDGSFFLYSKLTVDKSRWQQGNVFSCSVMHEALHNH YTQKSLSLSPGK |
| mut61-linker2-hFc (H16E/V91R) | SEQ ID NO: 54 | APTSSSTKKTQLQLEELLLDLQMILNGINNYKNPKLTRMLTFKFYM PKKATELKHLQCLEEELKPLEEVLNLAQSKNFHLRPRDLISNINRIV LELKGSETTFMCEYADETATIVEFLNRWITFAQSIISTLTGGGGSGG GGSGGGGSEPKSSDKTHTCPPCPAPELLGGPSVFLFPPKPKDTLMIS RTPEVTCVVVDVSHEDPEVKFNWYVDGVEVHNAKTKPREEQYGS TYRVVSVLTVLHQDWLNGKEYKCKVSNKALPAPIEKTISKAKGQP REPQVYTLPPSRDELTKNQVSLTCLVKGFYPSDIAVEWESNGQPEN NYKTTPPVLDSDGSFFLYSKLTVDKSRWQQGNVFSCSVMHEALHN HYTQKSLSLSPGK |
| mut61.08-linker2-hFc (H16E/V91R/Y31V/A73L/H79Q) | SEQ ID NO: 55 | APTSSSTKKTQLQLEELLLDLQMILNGINNVKNPKLTRMLTFKFYM PKKATELKHLQCLEEELKPLEEVLNLLQSKNFQLRPRDLISNINRIV LELKGSETTFMCEYADETATIVEFLNRWITFAQSIISTLTGGGGSGG GGSGGGGSEPKSSDKTHTCPPCPAPELLGGPSVFLFPPKPKDTLMIS RTPEVTCVVVDVSHEDPEVKFNWYVDGVEVHNAKTKPREEQYGS TYRVVSVLTVLHQDWLNGKEYKCKVSNKALPAPIEKTISKAKGQP REPQVYTLPPSRDELTKNQVSLTCLVKGFYPSDIAVEWESNGQPEN NYKTTPPVLDSDGSFFLYSKLTVDKSRWQQGNVFSCSVMHEALHN HYTQKSLSLSPGK |
| mut61.46-linker2-hFc (H16E/V91R/L18I/I89L/V93I) | SEQ ID NO: 56 | APTSSSTKKTQLQLEELILDLQMILNGINNYKNPKLTRMLTFKFYMP KKATELKHLQCLEEELKPLEEVLNLAQSKNFHLRPRDLISNLNRIIL ELKGSETTFMCEYADETATIVEFLNRWITFAQSIISTLTGGGGSGGG GSGGGGSEPKSSDKTHTCPPCPAPELLGGPSVFLFPPKPKDTLMISR TPEVTCVVVDVSHEDPEVKFNWYVDGVEVHNAKTKPREEQYGST YRVVSVLTVLHQDWLNGKEYKCKVSNKALPAPIEKTISKAKGQPR EPQVYTLPPSRDELTKNQVSLTCLVKGFYPSDIAVEWESNGQPENN YKTTPPVLDSDGSFFLYSKLTVDKSRWQQGNVFSCSVMHEALHNH YTQKSLSLSPGK |

Example 5—Production and Purification of IL-2 Mutants

HEK293 cells (purchased from the Cell Bank of the Chinese Academy of Sciences) were transiently transfected (PEI, polysciences) with the plasmids constructed in Example 4, and then expanded at 37° C. in FreeStyle™ 293 Expression Medium (purchased from Gibco). After 7 days, the cell culture medium was collected, and the cell components were removed by centrifugation to obtain the culture supernatant containing IL-2-hFc fusion proteins.

The fusion proteins in the cell culture supernatant were purified using a 10 mL protein A column (purchased from Bestchrom). The protein A column was first equilibrated with 3 to 5 column volumes of an equilibrium buffer (PBS phosphate buffer, pH7.4), and then loaded with the clear culture supernatant at a flow rate of 10 mL/min. After loading, the protein A column was washed with 3 to 5 column volumes of the equilibrium buffer. The protein bound to the protein A column was eluted with an eluent buffer (0.02 M citric acid buffer, 0.1 M glycine, 0.1 M sodium chloride, pH 3.0), and the elution was monitored by a nucleic acid/protein detector (A280 ultraviolet absorption peak). The eluted proteins were collected and neutralized with the added buffer (1 M arginine, 0.4 M succinic acid, pH 9.0). The target proteins were then collected through a molecular sieve (purchased from Bestchrom) with a buffer system (20 mM PB, 200 mM sodium chloride, pH 6.0-6.5). The purified IL-2 mutant fusion proteins were obtained by aseptic filtration with a 0.22 m filter and preserved in sterile condition.

The purified IL-2 mutant fusion proteins (mutXX-linker2-hFc) were analyzed for protein concentration (A280/1.4) and SEC purity. The purified IL-2 mutant fusion proteins were qualified. The results of protein yield and concentration are shown in Table 5.

TABLE 5

Detection results of IL-2 mutant fusion proteins

| Mutant | Protein SEC purity | Protein concentration (mg/ml) |
|---|---|---|
| IL-2-linker2-hFc | 97.25% | 1.11 |
| mut7-linker2-hFc | 100% | 0.97 |
| mut7.08-linker2-hFc | 99.84% | 1.73 |
| mut7.36-linker2-hFc | 99.94% | 2.40 |
| mut7.39-linker2-hFc | 99.77% | 1.16 |
| mut7.46-linker2-hFc | 99.90% | 1.28 |
| mut7.57-linker2-hFc | 99.89% | 1.37 |
| mut7.66-linker2-hFc | 99.89% | 1.92 |
| mut8-linker2-hFc | 97.19% | 0.98 |
| mut8.08-linker2-hFc | — | 0.82 |
| mut8.36-linker2-hFc | — | 1.65 |
| mut11-linker2-hFc | 99.13% | 1.65 |
| mut11.08-linker2-hFc | 99.88% | 1.29 |
| mut11.31-linker2-hFc | 100.00% | 1.37 |
| mut11.36-linker2-hFc | 99.97% | 1.15 |
| mut11.46-linker2-hFc | 99.90% | 1.52 |
| mut61-linker2-hFc | 99.93% | 1.36 |
| mut61.08-linker2-hFc | 99.99% | 1.15 |
| mut61.46-linker2-hFc | 99.99% | 1.30 |

Example 6 DSF Assay of IL-2 Mutants

The buffer in Protein Thermal Shift Dye Kit (purchased from Applied Biosystems, Cat. No. 4461146) diluted to 50 times, the IL-2 mutant proteins (purified in Example 5) diluted to 0.5 mg/ml, and the dye diluted to 2 times were added to a 20 μL reaction system. After being mixed evenly, the mixture was added into 8-tube strips with 2 duplicate tubes for each sample. The tubes were covered, centrifuged for 5-10 seconds, and analyzed by the Applied Biosystems 7500. The Tm values were then obtained by using Boltzmann method to analyze the melting curve. The specific Tm values are shown in Table 6.

According to the results shown in Table 6, compared to wild-type IL-2 (IL2-linker2-hFc), the IL-2 mutants (mutXX-linker2-hFc) in Examples 4-5 had increased Tm values by more than 5° C., and some IL-2 mutants had increased Tm values by more than 9° C. As can be seen, all mutants had significantly improved thermal stability.

Surprisingly, compared to wild-type IL-2, the IL-2 mutants with decreased binding ability to βγ subunits had higher Tm values and improved thermal stability. The mutants which further combine thermal stability mutations maintained high Tm values, and some of the mutants combining thermal stability mutations still had Tm values by more than 2° C. and up to 6° C. as compared to the IL-2 mutants comprising only mutations that decrease the binding ability to βγ subunits, and the thermal stability was further improved.

TABLE 6

DSF assay results of IL-2 mutants

| Mutant | Tm (° C.) |
|---|---|
| IL-2-linker2-hFc | 45.95 |
| mut7-linker2-hFc | 51.08 |
| mut7.08-linker2-hFc | 54.70 |
| mut7.36-linker2-hFc | 56.95 |
| mut7.57-linker2-hFc | 57.54 |
| mut7.66-linker2-hFc | 56.64 |
| mut8-linker2-hFc | 55.24 |
| mut8.08-linker2-hFc | 55.32 |
| mut8.36-linker2-hFc | 56.84 |
| mut11-linker2-hFc | 56.63 |
| mut11.08-linker2-hFc | 58.80 |
| mut11.31-linker2-hFc | 59.37 |
| mut11.36-linker2-hFc | 57.56 |
| IL-2-linker2-hFc | 46.74 |
| mut7-linker2-hFc | 51.05 |
| mut7.39-linker2-hFc | 56.30 |
| mut7.46-linker2-hFc | 54.84 |
| mut11-linker2-hFc | 57.17 |
| mut11.46-linker2-hFc | 57.02 |
| IL-2-linker2-hFc | 46.86 |
| mut61-linker2-hFc | 56.84 |
| mut61.08-linker2-hFc | 57.71 |
| mut61.46-linker2-hFc | 56.84 |

Example 7—Construction of Stably Transfected Cell Lines Overexpressing Human or Mouse IL-2 Receptor A. Construction of Stably Transfected Cell Lines Overexpressing Human IL-2 Receptor α

The amino acid sequence of the human IL-2 receptor α subunit (gene accession number in NCBI is P01589, the specific sequence is as shown in SEQ ID NO: 57) was cloned into a pLVX-IRES-Puro vector (purchased from YouBio, Cat NO.VT1464) for lentiviral packaging. The CHO-K1 cell line (purchased from the Cell Bank of the Chinese Academy of Sciences) was then transfected with lentivirus. After transfected with the virus for 72 hours, the CHO cells were detected by flow cytometry with a known IL-2 receptor α subunit antibody (Art NO. 302606, purchased from BioLegend). When the transfected cells were detected to begin to express human IL-2 receptor α subunit, Puromycin (purchased from Gibco) was then added for screening. After the cells were recovered, they were subcloned into 96-well culture plates by limiting dilution, and cultured at 37° C. with 5% (v/v) $CO_2$. After about 2 weeks, some monoclonal cells were selected and expanded into 6-well plates. The expanded clones were further screened by flow cytometry with the known IL-2 receptor α subunit antibody. The monoclonal cell lines with better growth and higher fluorescence intensity were selected for further expansion, re-detected by flow cytometry and then frozen in liquid nitrogen to obtain stably transfected cell lines expressing human IL-2 receptor α subunit. Specific selection results are shown in Table 7 and FIG. 1. Positive cells (%) in Table 7 refer to the percentage of positive cells in the total number of cells. Table 7 shows that a series of CHO-K1 cell lines overexpressing IL-2 receptor α subunit have been prepared.

TABLE 7

FACS characterization of CHO-K1 cells expressing human IL-2 receptor α

| | | IL-2 receptor α antibody | | IgG subtype control | |
|---|---|---|---|---|---|
| Serial Number | Transfected cell clone name | Positive cells (%) | Average fluorescence intensity | Positive cells (%) | Average fluorescence intensity |
| 1 | CHO-K1 hIL-2Rα 1A6 | 100.00 | 38168 | — | — |
| 2 | CHO-K1 hIL-2Rα 2D2 | 100.00 | 21817 | — | — |
| 3 | CHO-K1 hIL-2Rα 2D5 | 100.00 | 18111 | — | — |
| 4 | CHO-K1 hIL-2Rα 2B8 | 99.80 | 19018 | 0.04 | 80.70 |

B. Construction of Stably Transfected Cell Lines Overexpressing Human IL-2 Receptor β

Figure 2:
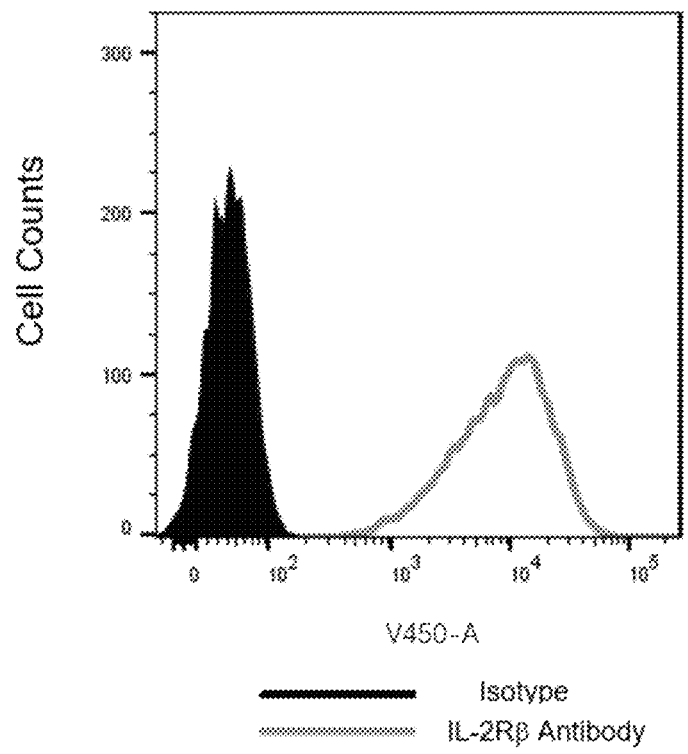
FIG. 2 shows the expression level of human IL-2 receptor β protein in the CHO-K1 hIL-2Rβ recombinant cell line (clone 2A5) detected by flow cytometry (FACS), wherein the IL-2 receptor β antibody is purchased from BioLegend; and the negative control refers to isotype control.

The amino acid sequence of the human IL-2 receptor β subunit (gene accession number in NCBI is P14784, the specific sequence is as shown in SEQ ID NO: 58) was cloned into a pLVX-IRES-Puro vector (purchased from YouBio, Cat NO. VT1464) for lentiviral packaging. The CHO-K1 cell line (purchased from the Cell Bank of the Chinese Academy of Sciences) was then transfected with lentivirus. After transfected with the virus for 72 hours, the CHO-K1 cells were detected by flow cytometry with a known IL-2 receptor β subunit antibody (Cat NO. 339010, purchased from BioLegend). When the transfected cells were detected to begin to express human IL-2 receptor β subunit, Puromycin (purchased from Gibco) was then added for screening. After the cells were recovered, they were subcloned into 96-well culture plates by limiting dilution, and cultured at 37° C. with 5% (v/v) $CO_2$. After about 2 weeks, some monoclonal cells were selected and expanded into 6-well plates. The expanded clones were further screened by flow cytometry with the known IL-2 receptor β subunit antibody. The monoclonal cell lines with better growth and higher fluorescence intensity were selected for further expansion, re-detected by flow cytometry and then frozen in liquid nitrogen to obtain stably transfected cell lines expressing human IL-2 receptor β subunit. Specific selection results are shown in Table 8 and FIG. 2. Positive cells (%) in Table 8 refer to the percentage of positive cells in the total number of cells. Table 8 shows that a series of CHO-K1 cell lines overexpressing IL-2 receptor β subunit have been prepared.

TABLE 8

FACS characterization of CHO-K1 cells expressing human IL-2 receptor β

| | | IL-2 receptor β antibody | | IgG subtype control | |
|---|---|---|---|---|---|
| Serial Number | Transfected cell clone | Positive cells (%) | Average fluorescence intensity | Positive cells (%) | Average fluorescence intensity |
| 1 | CHO-K1 hIL-2Rβ 2A5 | 100.00 | 7905 | — | — |
| 2 | CHO-K1 hIL-2Rβ 2B3 | 99.40 | 5081 | 0.03 | 41.50 |
| 3 | CHO-K1 hIL-2Rβ 2H4 | 99.40 | 1226 | — | — |

C. Construction of Stably Transfected Cell Lines Overexpressing Human IL-2 Receptor βγ

Figure 3A:
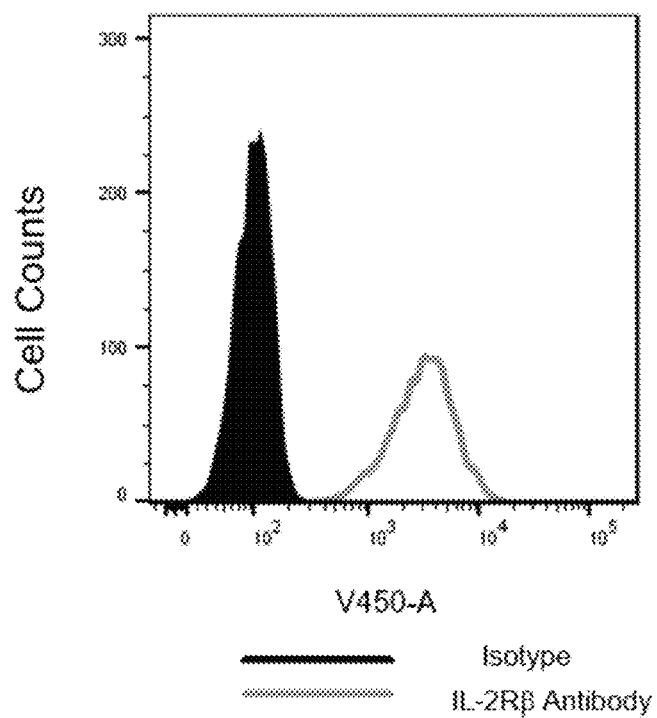
FIG. 3A shows the expression level of human IL-2 receptor β protein.
Figure 3B:
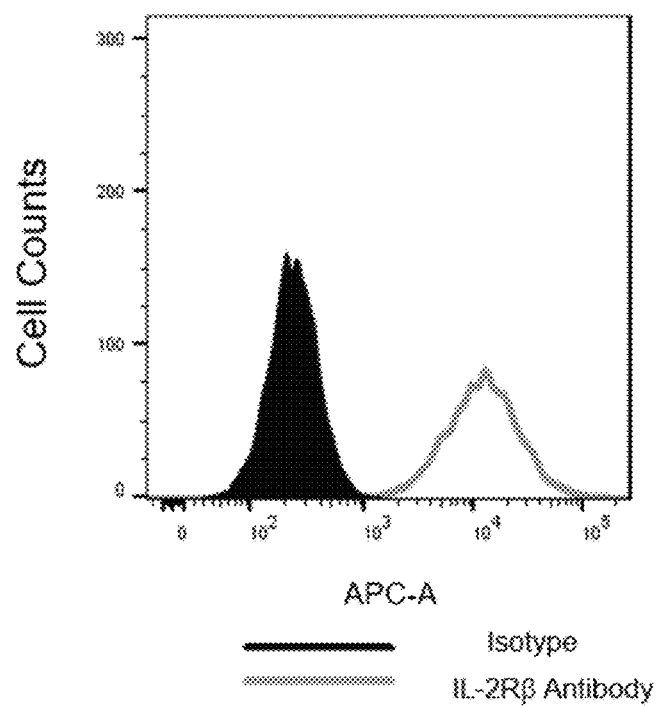
FIG. 3B shows the expression level of human IL-2 receptor γ protein.

The amino acid sequence of the human IL-2 receptor γ subunit (gene accession number in NCBI is P31785, the specific sequence is SEQ ID NO: 59) was cloned into a pLVX-IRES-Hygro vector for lentiviral packaging. The CHO-K1 cell line overexpressing human IL-2 receptor β subunit (CHO-K1 hIL-2R β, clone 2A5) was then transfected with lentivirus. After transfected with the virus for 72 hours, the CHO-K1 cells were detected by flow cytometry with known IL-2 receptor β and γ□ subunit antibodies (Cat NOs. 339010 and 338608, purchased from BioLegend). When the transfected cells were detected to begin to express human IL-2 receptor βγ subunits, Puromycin and Hygromycin (purchased from Gibco, Thermo) were then added for screening. After the cells were recovered, they were subcloned into 96-well culture plates by limiting dilution, and cultured at 37° C. with 5% (v/v) $CO_2$. After about 2 weeks, some monoclonal cells were selected and expanded into 6-well plates. The expanded clones were screened by flow cytometry with the known IL-2 receptor β and γ subunit antibodies. The monoclonal cell lines with better growth and higher fluorescence intensity were selected for further expansion, re-detected by flow cytometry and then frozen in liquid nitrogen to obtain stably transfected cell lines expressing human IL-2 receptor βγ subunits. Specific selection results are shown in Table 9 and FIG. 3A-FIG. 3B. Positive cells (%) in Table 9 refer to the percentage of positive cells in the total number of cells. Table 9 shows that a series of CHO-K1 cell lines overexpressing IL-2 receptor βγ subunits have been prepared.

TABLE 9

FACS characterization of CHO-K1 cells expressing human IL-2 receptor βγ

| | | IL-2 receptor β antibody | | IgG subtype control | | IL-2 receptor γ antibody | | IgG subtype control | |
|---|---|---|---|---|---|---|---|---|---|
| Serial Number | Transfected cell clone | Positive cells (%) | Average fluorescence intensity | Positive cells (%) | Average fluorescence intensity | Positive cells (%) | Average fluorescence intensity | Positive cells (%) | Average fluorescence intensity |
| 1 | CHO-K1 IL-2Rβγ 2D3 | 100.00 | 4569 | 0.65 | 115 | 98.90 | 8932 | 23.30 | 1070 |
| 2 | CHO-K1 hIL-2Rβγ 2C11 | 99.70 | 2111 | — | — | 99.00 | 31664 | — | — |
| 3 | CHO-K1 IL-2Rβγ 2E6 | 100.00 | 2909 | — | — | 98.80 | 11764 | — | — |

D. Construction of Stably Transfected Cell Lines Overexpressing Human IL-2 Receptor αβγ

Figure 4A:
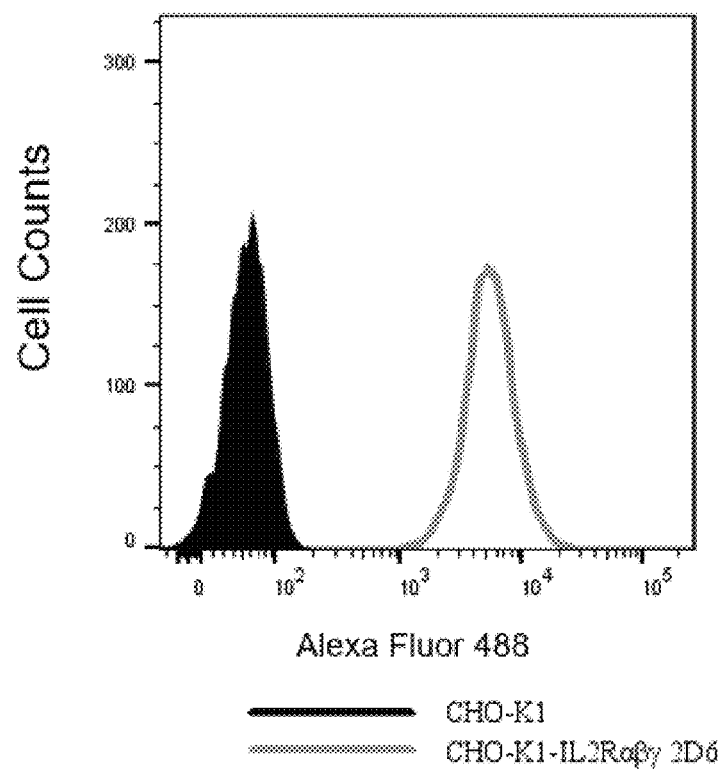
FIG. 4A shows the expression level of human IL-2 receptor α protein.
Figure 4B:
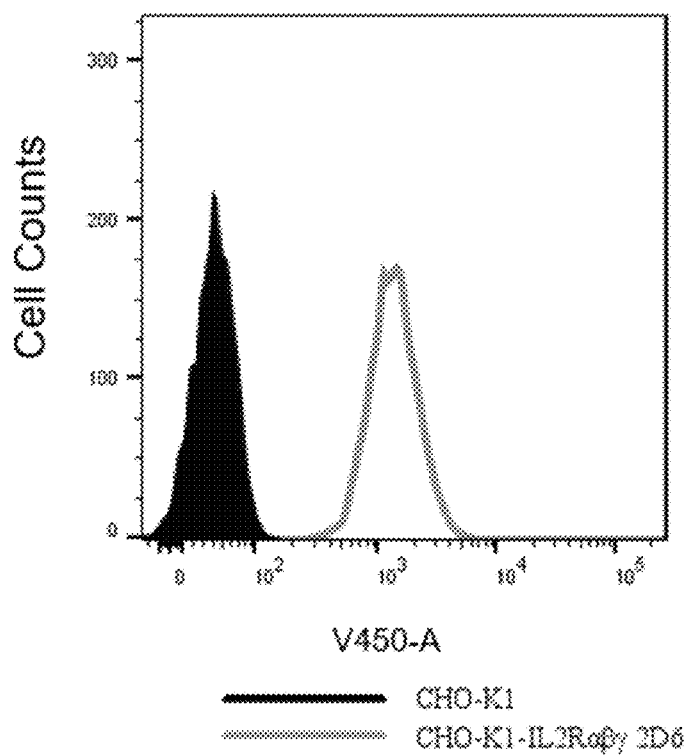
FIG. 4B shows the expression level of human IL-2 receptor β protein.
Figure 4C:
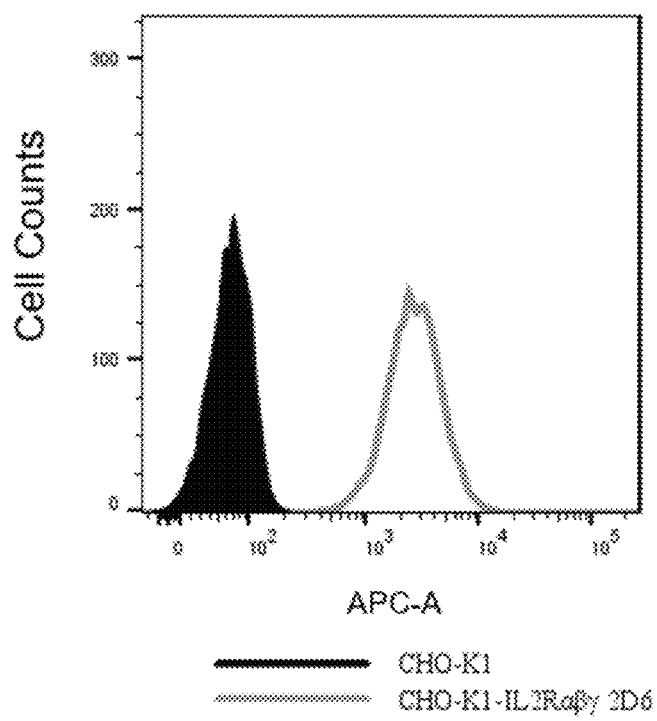
FIG. 4C shows the expression level of human IL-2 receptor γ protein.
Figure 5A:
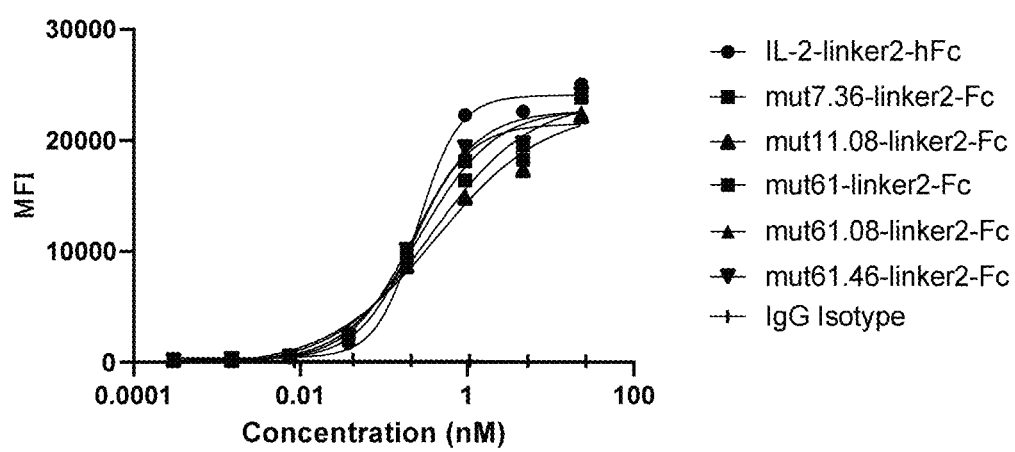
FIG. 5A shows the binding activity of mut7.36-linker2-hFc, mut11.08-linker2-hFc, mut61-linker2-hFc, mut61.08-linker2-hFc or mut61.46-linker2-hFc to CHO-K1 IL-2 receptor αβγ recombinant cells.
Figure 5B:
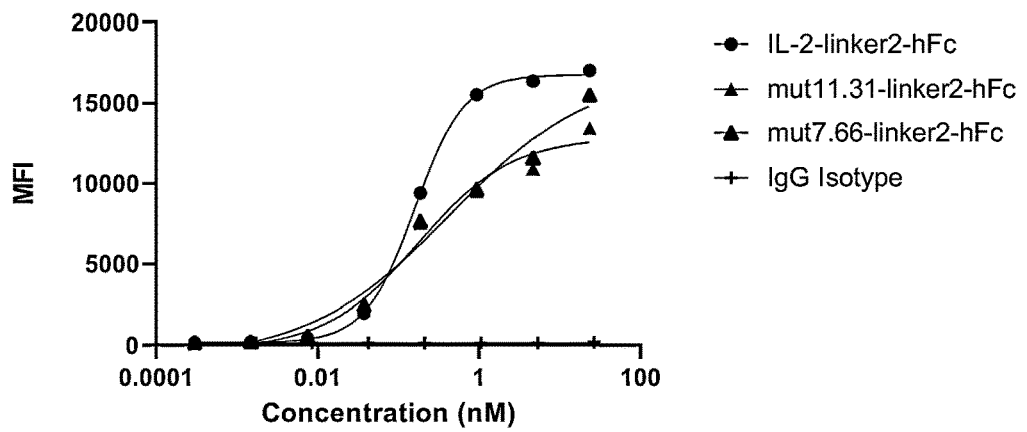
FIG. 5B shows the binding activity of mut11.31-linker2-hFc or mut7.66-linker2-hFc to CHO-K1 IL-2 receptor αβγ recombinant cells.
Figure 5C:
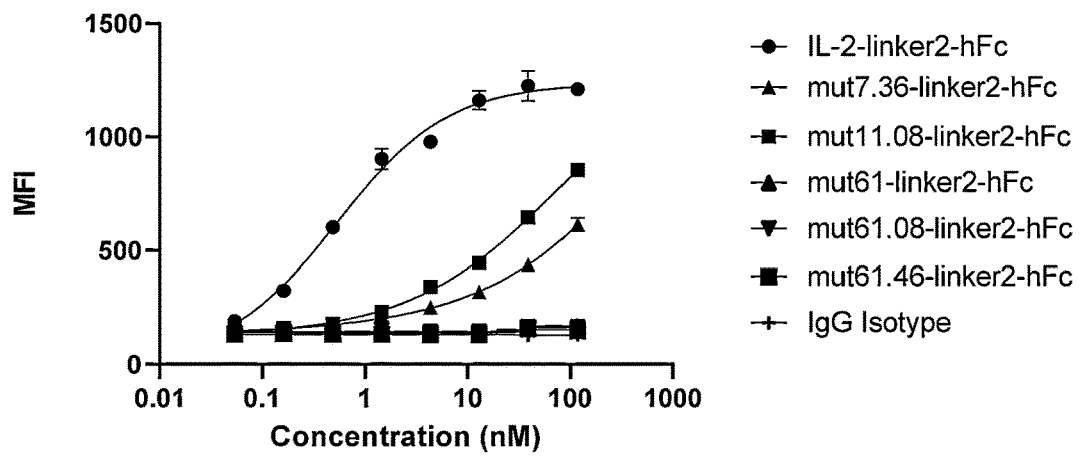
FIG. 5C shows the binding activity of mut7.36-linker2-hFc, mut11.08-linker2-hFc, mut61-linker2-hFc, mut61.08-linker2-hFc or mut61.46-linker2-hFc to CHO-K1 IL-2 receptor βγ recombinant cells.
Figure 5D:
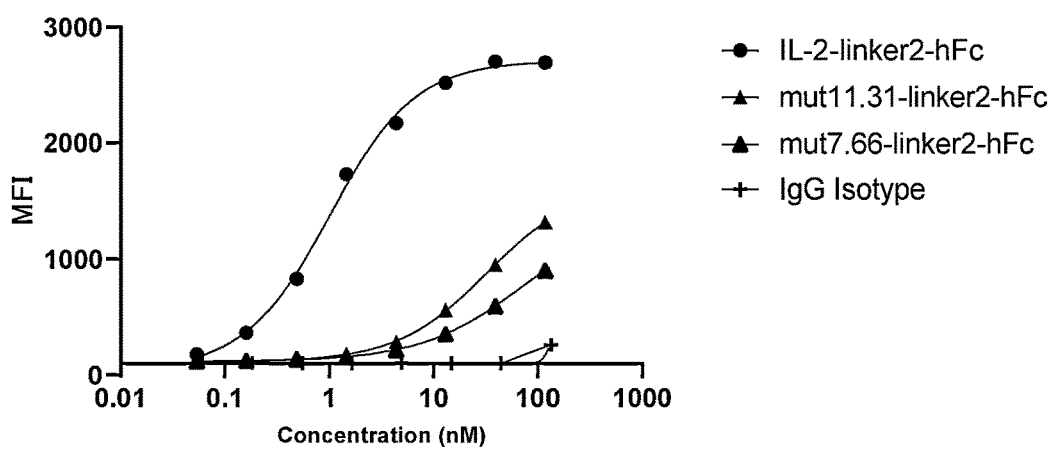
FIG. 5D shows the binding activity of mut11.31-linker2-hFc or mut7.66-linker2-hFc to CHO-K1 IL-2 receptor βγ recombinant cells.
Figure 6A:
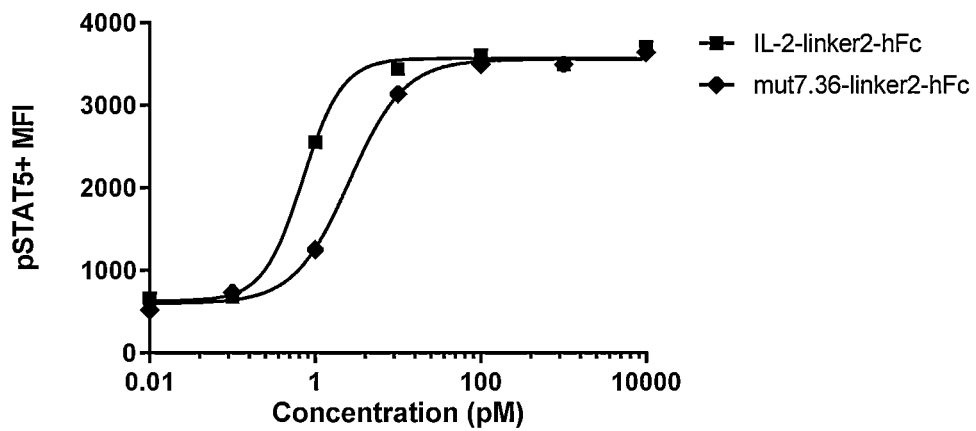
FIG. 6A shows the effect of mut7.36-linker2-hFc on the level of STAT5 phosphorylation in Tregs.
Figure 6B:
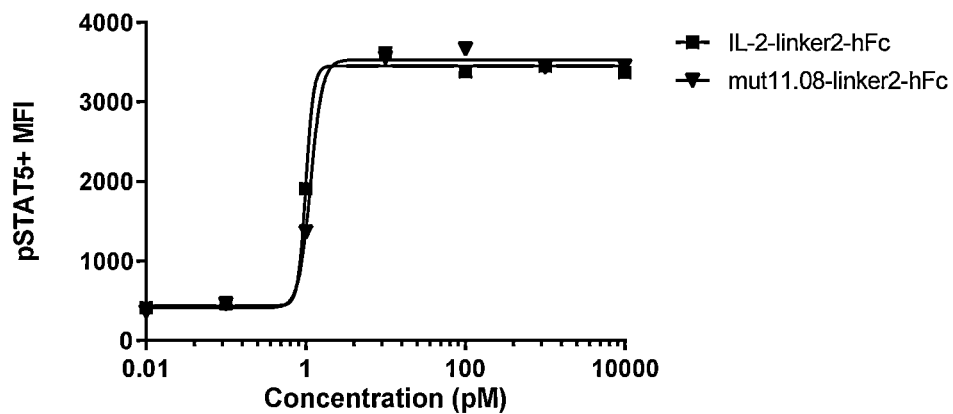
FIG. 6B shows the effect of mut11.08-linker2-hFc on the level of STAT5 phosphorylation in Tregs.
Figure 6C:
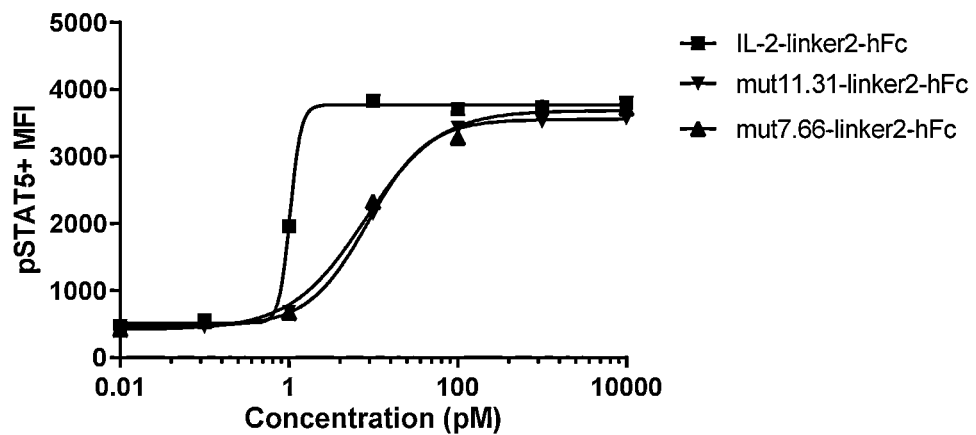
FIG. 6C shows the effect of mut11.31-linker2-hFc or mut7.66-linker2-hFc on the level of STAT5 phosphorylation in Tregs.
Figure 6D:
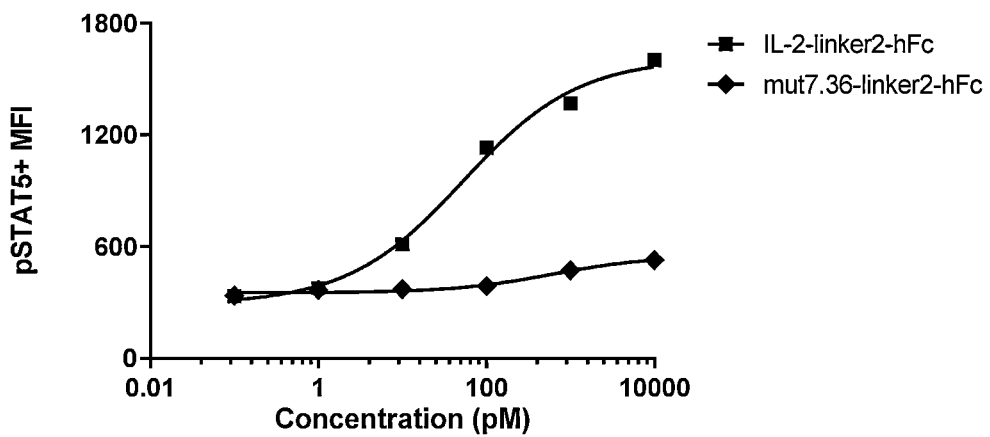
FIG. 6D shows the effect of mut7.36-linker2-hFc on the level of phosphorylation in CD4$^+$CD25$^-$FoxP3$^-$ T cells.
Figure 6E:
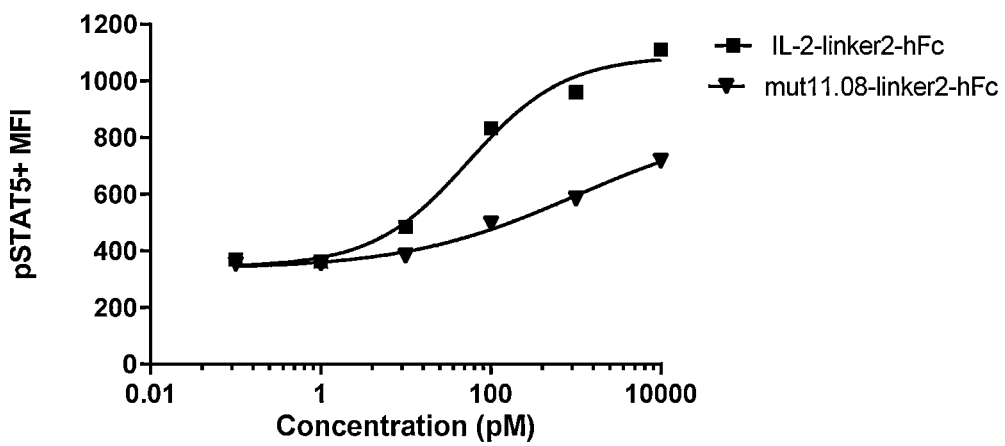
FIG. 6E shows the effect of mut11.08-linker2-hFc on the level of phosphorylation in CD4$^+$CD25$^-$FoxP3$^-$ T cells.
Figure 6F:
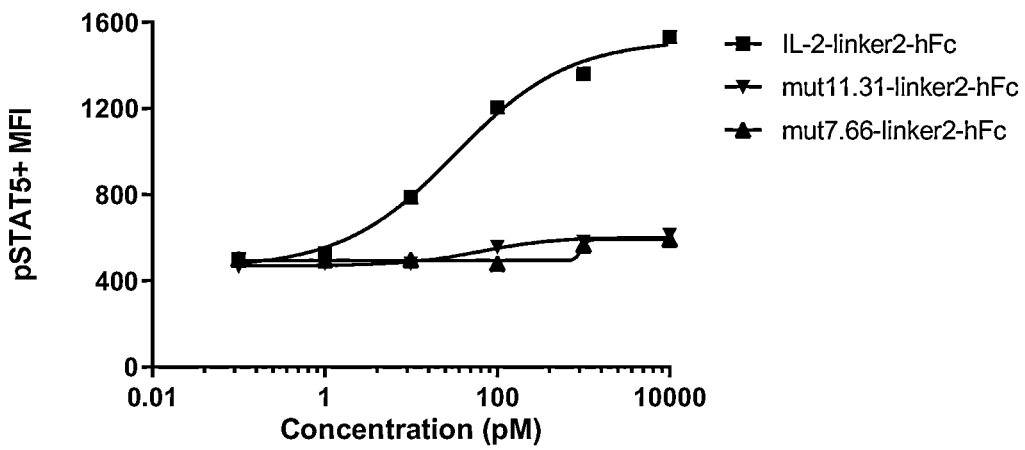
FIG. 6F shows the effect of mut11.31-linker2-hFc or mut7.66-linker2-hFc on the level of phosphorylation in CD4$^+$CD25$^-$FoxP3$^-$ T cells.
Figure 6G:
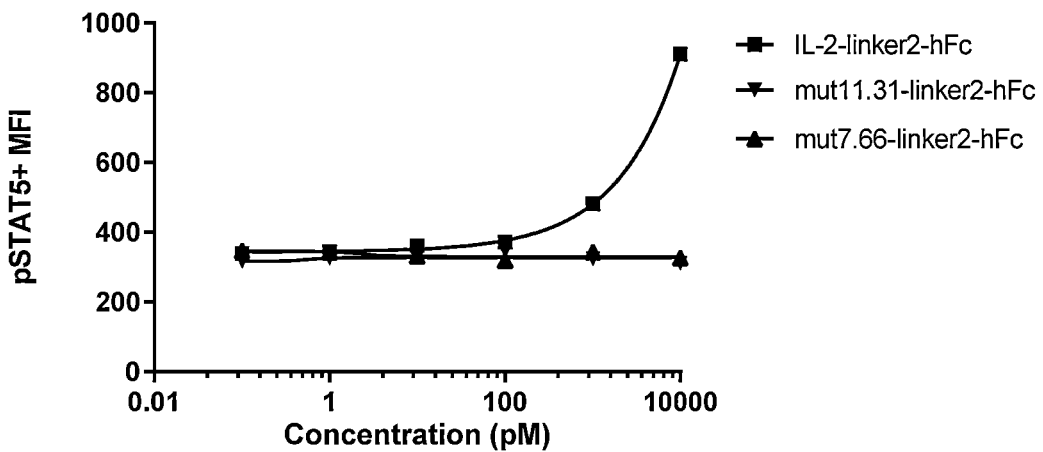
FIG. 6G shows the effect of mut7.36-linker2-hFc on the level of phosphorylation in CD8$^+$ T cells.
Figure 6H:
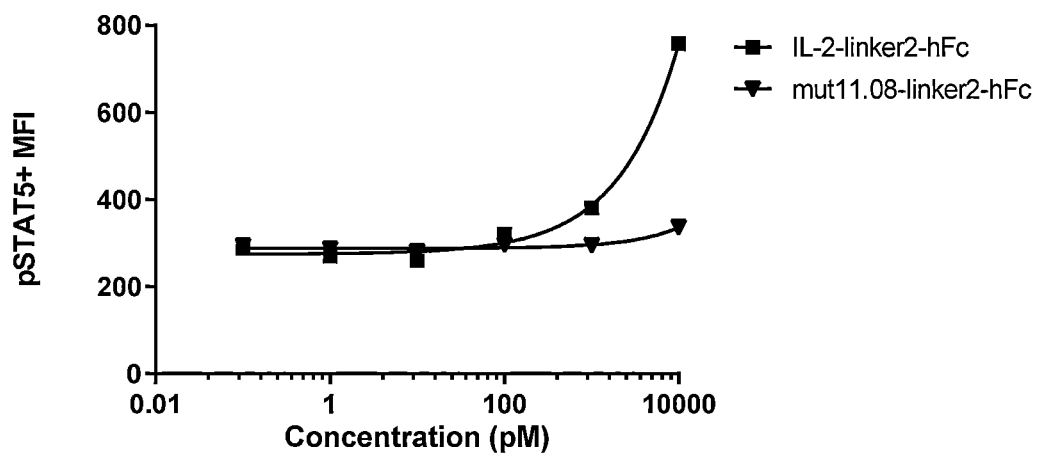
FIG. 6H shows the effect of mut11.08-linker2-hFc on the level of phosphorylation in CD8$^+$ T cells.
Figure 6I:
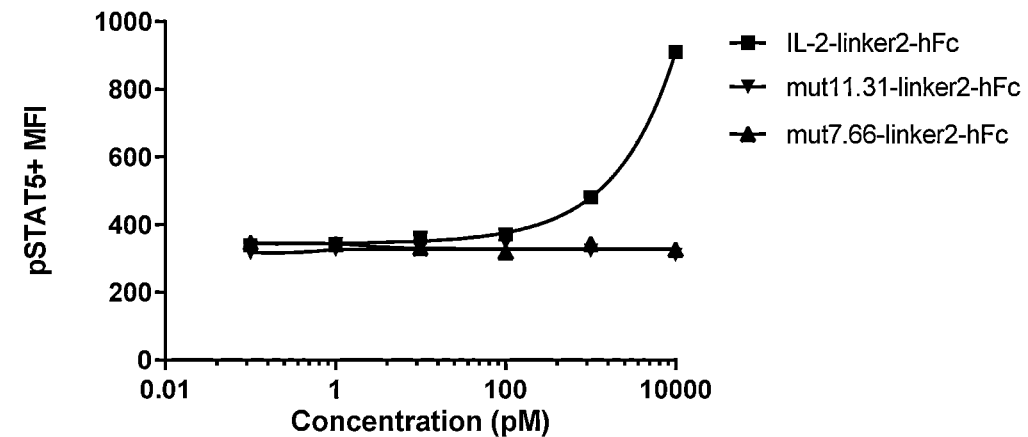
FIG. 6I shows the effect of mut11.31-linker2-hFc or mut7.66-linker2-hFc on the level of phosphorylation in CD8$^+$ T cells.
Figure 7A:
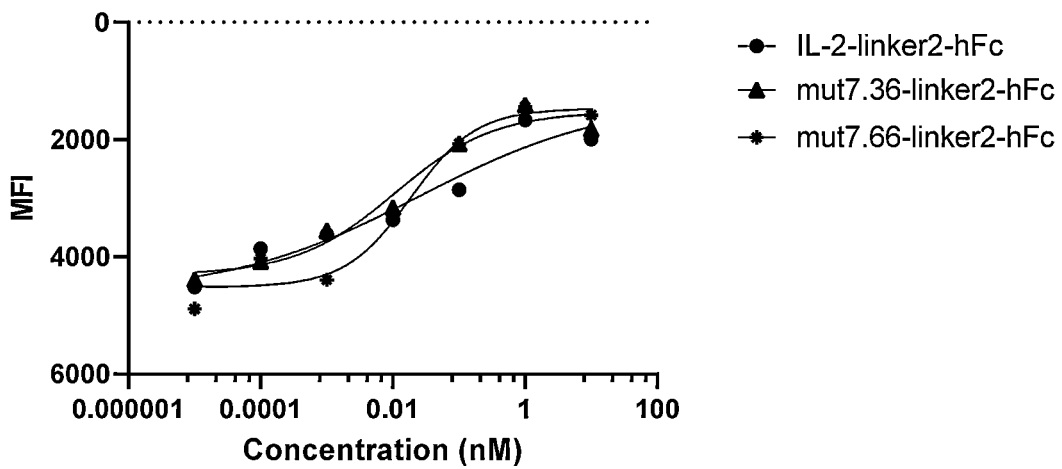
FIG. 7A shows the effect of mut7.36-linker2-hFc or mut7.66-linker2-hFc on the level of proliferation of Tregs.
Figure 7B:
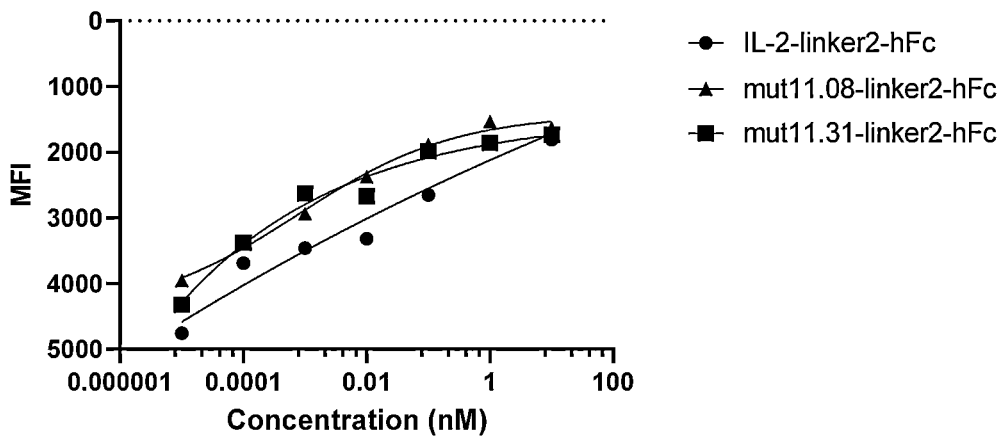
FIG. 7B shows the effect of mut11.08-linker2-hFc or mut11.31-linker2-hFc on the level of proliferation of Tregs.
Figure 7C:
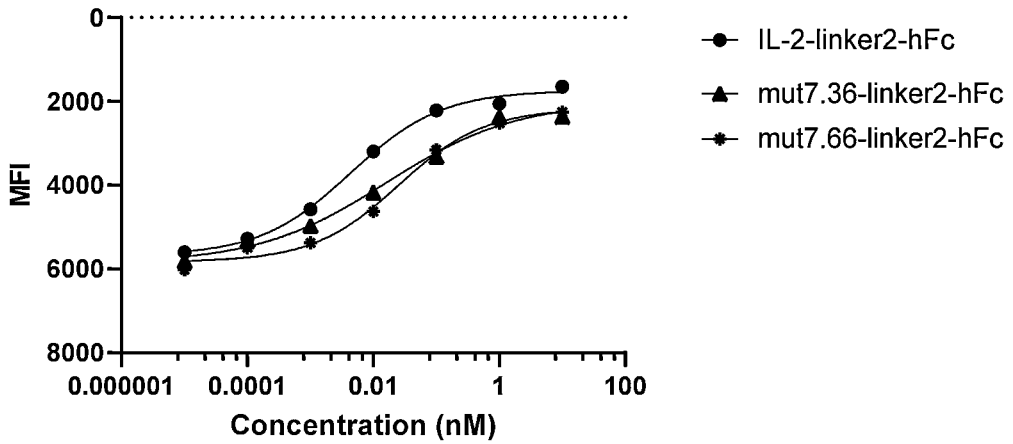
FIG. 7C shows the effect of mut7.36-linker2-hFc or mut7.66-linker2-hFc on the level of proliferation of CD4$^+$CD25$^-$FoxP3$^-$T cells.
Figure 7D:
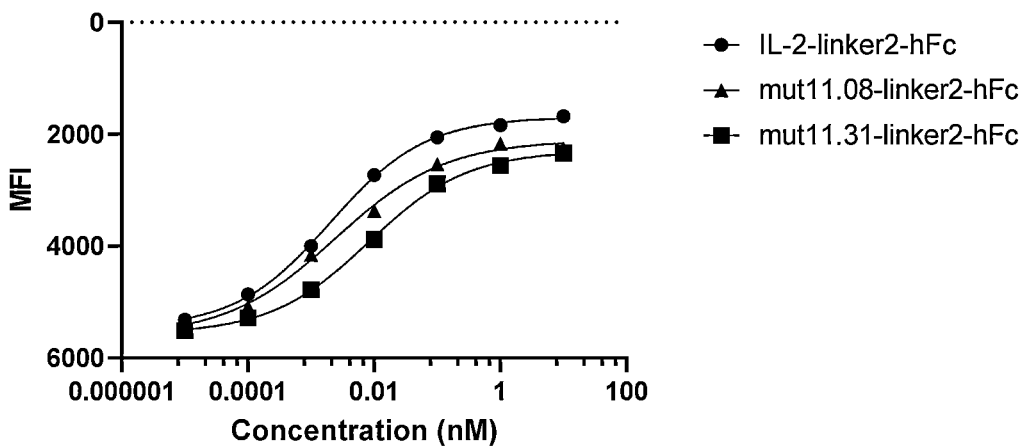
FIG. 7D shows the effect of mut11.08-linker2-hFc or mut11.31-linker2-hFc on the level of proliferation of CD4$^+$CD25$^-$FoxP3$^-$T cells.
Figure 7E:
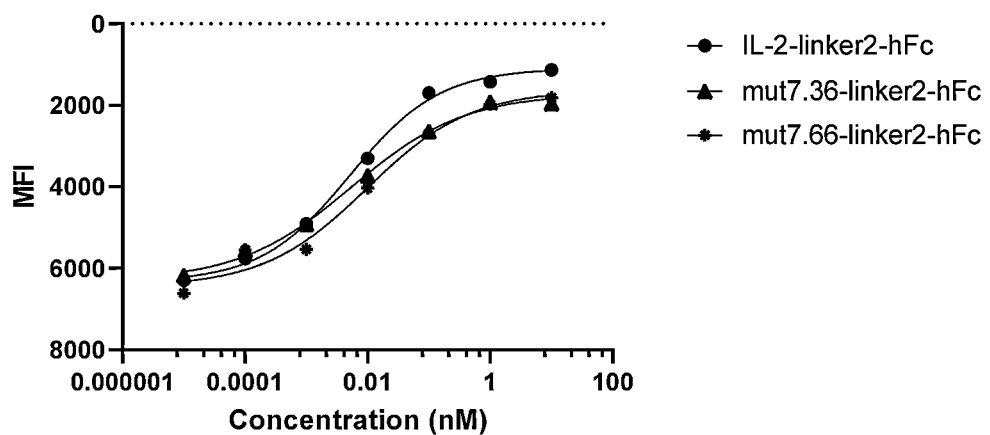
FIG. 7E shows the effect of mut7.36-linker2-hFc or mut7.66-linker2-hFc on the level of proliferation of CD8$^+$CD25$^-$T cells.
Figure 7F:
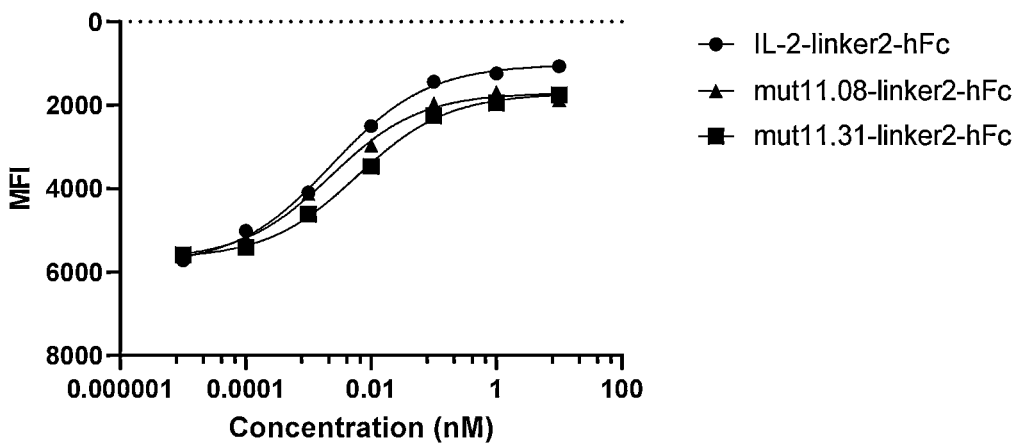
FIG. 7F shows the effect of mut11.08-linker2-hFc or mut11.31-linker2-hFc on the level of proliferation of CD8$^+$CD25$^-$T cells.

The amino acid sequence of the human IL-2 receptor α subunit was cloned into a pLVX-IRES-zsGreen vector for lentiviral packaging. The CHO-K1 cell line overexpressing human IL-2 receptor βγ subunits were transfected with ventivirus. After transfected with the virus for 72 hours, the CHO-K1 cells were detected by flow cytometry with the known IL-2 receptor α, β and γ subunit antibodies (ibid., purchased from BioLegend). When the transfected cells were detected to begin to express human IL-2 receptor αβγ subunits, Puromycin, Hygromycin (purchased from Gibco, Thermo) and GFP (for fluorescent expression) were added for screening. After the cells were recovered, they were subcloned into 96-well culture plates by limiting dilution, and cultured at 37° C. with 5% (v/v) $CO_2$. After about 2 weeks, some monoclonal cells were selected and expanded into 6-well plates. The expanded clones were screened by flow cytometry with the known IL-2 receptor α, β and γ subunit antibodies. The monoclonal cell lines with better growth and higher fluorescence intensity were selected for further expansion, re-detected by flow cytometry and then frozen in liquid nitrogen to obtain stably transfected cell lines expressing human IL-2 receptor αβγ subunits. Specific selection results are shown in Table 10 and FIG. 4A-FIG. 4B. Positive cells (%) in Table 10 refer to the percentage of positive cells in the total number of cells. Table 10 shows that a series of CHO-K1 cell lines overexpressing IL-2 receptor αβγ subunits have been prepared.

TABLE 10

FACS characterization of CHO-K1 cells expressing human IL-2 receptor αβγ

| | | IL-2 receptor α antibody | | IL-2 receptor β antibody | | IL-2 receptor γ antibody | |
|---|---|---|---|---|---|---|---|
| Serial Number | Transfected cell clone | Positive cells (%) | Average fluorescence intensity | Positive cells (%) | Average fluorescence intensity | Positive cells (%) | Average fluorescence intensity |
| 1 | CHO-K1 hIL-2R αβγ 1E3 | 99.90 | 10667 | 100.00 | 3002 | 99.90 | 14863 |
| 2 | CHO-K1 hIL-2R αβγ 2D6 | 99.90 | 5265 | 99.90 | 1324 | 99.80 | 2575 |
| 3 | CHO-K1 hIL-2R αβγ 1A10 | 100.00 | 12255 | 88.60 | 465 | 99.60 | 4106 |

TABLE 11

Genes used in the construction of stably transfected cell lines in Example 7 (A-D) and sequence information of encoded proteins thereof

| Gene | SEQ ID NO | Sequence information |
|---|---|---|
| hIL2Rα | SEQ ID NO: 57 | MDSYLLMWGLLTFIMVPGCQAELCDDDPPEIPHATFKAMAYKEGTMLNCEC KRGFRRIKSGSLYMLCTGNSSHSSWDNQCQCTSSATRNTTKQVTPQPEEQKE RKTTEMQSPMQPVDQASLPGHCREPPPWENEATERIYHFVVGQMVYYQCVQ GYRALHRGPAESVCKMTHGKTRWTQPQLICTGEMETSQFPGEEKPQASPEG RPESETSCLVTTTDFQIQTEMAATMETSIFTTEYQVAVAGCVFLLISVLLLSGL TWQRRQRKSRRTI |
| hIL2Rβ | SEQ ID NO: 58 | MAAPALSWRLPLLILLLPLATSWASAAVNGTSQFTCFYNSRANISCVWSQDG ALQDTSCQVHAWPDRRRWNQTCELLPVSQASWACNLILGAPDSQKLTTVDI VTLRVLCREGVRWRVMAIQDFKPFENLRLMAPISLQVVHVETHRCNISWEIS QASHYFERHLEFEARTLSPGHTWEEAPLLTLKQKQEWICLETLTPDTQYEFQ VRVKPLQGEFTTWSPWSQPLAFRTKPAALGKDTIPWLGHLLVGLSGAFGFIIL VYLLINCRNTGPWLKKVLKCNTPDPSKFFSQLSSEHGGDVQKWLSSPFPSSSF SPGGLAPEISPLEVLERDKVTQLLLQQDKVPEPASLSSNHSLTSCFTNQGYFFF HLPDALEIEACQVYFTYDPYSEEDPDEGVAGAPTGSSPQPLQPLSGEDDAYCT FPSRDDLLLFSPSLLGGPSPPSTAPGGSGAGEERMPPSLQERVPRDWDPQPLG PPTPGVPDLVDFQPPPELVLREAGEEVPDAGPREGVSFPWSRPPGQGEFRALN ARLPLNTDAYLSLQELQGQDPTHLV |
| hIL2Rγ | SEQ ID NO: 59 | MLKPSLPFTSLLFLQLPLLGVGLNTTILTPNGNEDTTADFFLTTMPTDSLSVST LPLPEVQCFVFNVEYMNCTWNSSSEPQPTNLTLHYWYKNSDNDKVQKCSHY LFSEEITSGCQLQKKEIHLYQTFVVQLQDPREPRRQATQMLKLQNLVIPWAPE NLTLHKLSESQLELNWNNRFLNHCLEHLVQYRTDWDHSWTEQSVDYRHKFS LPSVDGQKRYTFRVRSRFNPLCGSAQHWSEWSHPIHWGSNTSKENPFLFALE AVVISVGSMGLIISLLCVYFWLERTMPRIPTLKNLEDLVTEYHGNFSAWSGVS KGLAESLQPDYSERLCLVSEIPPKGGALGEGPGASPCNQHSPYWAPPCYTLKP ET |

Example 8—Detection of the Binding Activity of IL-2 Mutant to Receptor-Expressing Cells by Flow Cytometry (FACS)

CHO-K1 cells expressing IL-2 receptor αβγ (CHO-K1 hIL-2R αβγ 2D6) or CHO-K1 cells expressing IL-2 receptor βγ (CHO-K1 hIL-2R βγ 2E6) were expanded to 90% confluency in T-75 cell culture flasks. The medium was removed, followed by washing of the flask once with PBS buffer (purchased from Hyclone, Cat NO. SH30256.01). The cells were treated with 2 mL of trypsin containing 0.25% EDTA (purchased from Invitrogen, Cat NO. 25200072) for 2-3 minutes, neutralized with 8 mL of DMEM/F-12 (purchased from Gibco, Cat NO. 12634-010) containing 10% (w/w) fetal bovine serum (purchased from Gibco, Cat NO. 10099-141C), pipetted for 3-4 times, then collected into a 15 ml centrifuge tube, counted, and centrifuged at 1000 rpm for 5 minutes at room temperature. After the culture medium was discarded, the cells were re-suspended with RPMI-1640 containing 2% (w/w) fetal bovine serum (purchased from Gibco, Cat NO. A10491-01) and then diluted to $1.43 \times 10^6$ cells/ml. The cells were added into a U-shaped bottom 96-well FACS reaction plate at 70 μL per well and placed at 4° C. or on ice for later use. The IL-2 mutants to be detected were diluted with RPMI-1640 containing 2% (w/w) fetal bovine serum, added into the cells at 30 μL per well, mixed well, and incubated on ice for 1 hour. The plate was then washed twice with FACS buffer (PBS buffer containing 2% (w/w) bovine serum albumin). Fluorescence-labeled secondary antibody (purchased from Biolegend, Cat NO. 409306) was added into the plate at 100 μL per well and incubated on ice for 30 minutes. The plate was then washed twice with FACS buffer. Detection and analysis were performed by FACS (FACS Canto II, purchased from BD Company). Alternatively, the cells were suspended with 100 μL FACS buffer containing 2% (w/w) paraformaldehyde (purchased from DingGuo, Cat NO. AR-0211) and then stored at 4° C. until further FACS detection. 100 μL PBS buffer was added to each well before FACS detection. Detection and analysis was performed by FACS. The results are shown in FIG. 5A-FIG. 5D and Table 12-Table 13. The results show that IL-2 mutants could bind to human IL-2 receptor αβγ trimer on the cell surface. The binding activity of IL-2 mutants to human IL-2 receptor βγ dimer on the cell surface was weaker than that of wild type IL-2. The binding activity of mut6-linker2-hFc, mut67.08-linker2-hFc and mut61.46-linker2-hFc to CHO-K1 IL-2R βγ dimer was greatly inhibited. The MFI in the following tables is the average fluorescence intensity value of the detected cell populations.

TABLE 12

Binding Activity of IL-2 mutants to CHO-K1 IL2 receptor αβγ recombinant cell line (CHO-K1 IL2R αβγ) detected by FACS

| | Protein concentration (nM) | | | | | | | |
|---|---|---|---|---|---|---|---|---|
| | 23.529 | 4.7059 | 0.9412 | 0.1882 | 0.0376 | 0.0075 | 0.0015 | 0.0003 |
| IL-2-linker2-hFc(MFI) | 25072 | 22623 | 22295 | 9026 | 1728 | 457 | 161 | 251 |
| Mut7.36-linker2-hFc(MFI) | 23892 | 19565 | 18132 | 9608 | 2416 | 570 | 272 | 171 |
| Mut11.08-linker2-hFc(MFI) | 22230 | 17370 | 14857 | 8713 | 2736 | 621 | 268 | 251 |
| Mut61-linker2-hFc(MFI) | 23858 | 18259 | 16403 | 9188 | 2307 | 544 | 224 | 194 |
| Mut61.08-linker2-hFc(MFI) | 22558 | 19652 | 18992 | 9557 | 2131 | 575 | 303 | 190 |
| Mut61.46-linker2-hFc(MFI) | 24244 | 19701 | 19386 | 10124 | 2384 | 521 | 280 | 186 |
| Protein concentration (nM) | 26.667 | 5.3333 | 1.0667 | 0.2133 | 0.0427 | 0.0085 | 0.0017 | 0.0003 |
| Human IgG control | 118 | 124 | 157 | 181 | 274 | 119 | 120 | 146 |

| | Protein concentration (nM) | | | | | | | |
|---|---|---|---|---|---|---|---|---|
| | 23.529 | 4.7059 | 0.9412 | 0.1882 | 0.0376 | 0.0075 | 0.0015 | 0.0003 |
| IL-2-linker2-hFc(MFI) | 17021 | 16362 | 15503 | 9402 | 1983 | 423 | 188 | 156 |
| Mut7.66-linker2-hFc(MFI) | 15503 | 11604 | 9659 | 7683 | 2485 | 568 | 227 | 177 |
| Mut11.31-linker2-hFc(MFI) | 13449 | 10906 | 9502 | 7521 | 2181 | 553 | 214 | 172 |
| Protein concentration (nM) | 26.667 | 5.3333 | 1.0667 | 0.2133 | 0.0427 | 0.0085 | 0.0017 | 0.0003 |
| Human IgG control | 187 | 136 | 138 | 139 | 144 | 145 | 140 | 146 |

TABLE 13

Binding Activity of IL-2 mutants to CHO-K1 IL2 receptor βγ recombinant cell line (CHO-K1 IL2R βγ) detected by FACS

| | Protein concentration (nM) | | | | | | | |
|---|---|---|---|---|---|---|---|---|
| | 117.65 | 39.216 | 13.072 | 4.357 | 1.452 | 0.484 | 0.161 | 0.054 |
| IL-2-linker2-hFc(MFI) | 1210 | 1226 | 1162 | 980 | 904 | 603 | 325 | 191 |
| Mut7.36-linker2-hFc(MFI) | 615 | 438 | 318 | 250 | 210 | 165 | 156 | 153 |
| Mut11.08-linker2-hFc(MFI) | 854 | 645 | 447 | 342 | 232 | 178 | 160 | 144 |
| Mut61-linker2-hFc(MFI) | 169 | 155 | 142 | 142 | 145 | 146 | 148 | 142 |
| Mut61.08-linker2-hFc(MFI) | 164 | 163 | 144 | 144 | 157 | 144 | 146 | 141 |
| Mut61.46-linker2-hFc(MFI) | 148 | 159 | 132 | 131 | 134 | 133 | 136 | 134 |
| Protein concentration (nM) | 133.33 | 44.444 | 14.815 | 4.938 | 1.646 | 0.549 | 0.183 | 0.061 |
| Human IgG control | 130 | 130 | 136 | 134 | 139 | 141 | 141 | 146 |

TABLE 13-continued

Binding Activity of IL-2 mutants to CHO-K1 IL2 receptor βγ recombinant
cell line (CHO-K1 IL2R βγ) detected by FACS

| | Protein concentration (nM) | | | | | | | |
|---|---|---|---|---|---|---|---|---|
| | 117.65 | 39.216 | 13.072 | 4.357 | 1.452 | 0.484 | 0.161 | 0.054 |
| IL-2-linker2-hFc(MFI) | 2694 | 2703 | 2518 | 2170 | 1729 | 831 | 363 | 177 |
| Mut7.66-linker2-hFc(MFI) | 905 | 597 | 357 | 216 | 157 | 136 | 124 | 118 |
| Mut11.31-linker2-hFc(MFI) | 1320 | 950 | 560 | 285 | 180 | 134 | 121 | 115 |
| Protein concentration (nM) | 133.33 | 44.444 | 14.815 | 4.938 | 1.646 | 0.549 | 0.183 | 0.061 |
| Human IgG control | 259 | 100 | 101 | 107 | 101 | 102 | 104 | 109 |

Example 9—Activation of Signaling Pathways in Different Cells by IL-2 Mutants Detected by STAT5 Phosphorylation Assay Frozen Peripheral Blood Mononuclear Cells (PBMCs) (purchased from Allcells) were thawed. 50 μL of 5×10$^5$ PBMCs and 50 μL of an IL-2 mutant were added to each well, and allowed to react in a carbon dioxide incubator for 15 minutes. After the reaction, 100 μL precooled DPBS was added to each well to stop the reaction. After centrifugation, PBMCs were stained with Livedead Violet (Invitrogen-L 34964), fixed with Fix I (BD-557870) at 37° C. for 10 minutes, and permeabilized with PermIII (BD-558050) on ice for 30 minutes. PBMCs were then stained with CD3-AF700 (BD-557943), CD4-PerCP Cy5.5 (BD-560650), CD8-FTIC (BD-555366), CD25-PE (BD-557138), FoxP3-AF647 (BD-560045), and pSTAT5-PE Cy7 (Invitrogen-25-9010-42) at room temperature for 1 hour and washed twice before detection. The results are shown in FIG. 6A-FIG. 6I and Table 14-Table 16. The results show that, compared to wild-type IL-2, the STAT5 phosphorylation level activated by IL-2 mutants was similar in Treg cells, but was significantly reduced in CD4$^+$CD25$^-$FoxP3$^-$ T cells or CD8$^+$ T cells. The MFI in the following tables is the average fluorescence intensity value of STAT5 phosphorylation in the detected cell populations.

TABLE 14

STAT5 phosphorylation signal activated by
IL-2 mutants in Tregs detected by FACS

| Protein concentration (pM) | 10000 | 1000 | 100 | 10 | 1 | 0.1 | 0.01 |
|---|---|---|---|---|---|---|---|
| IL-2-linker2-hFc(MFI) | 3706 | 3498 | 3607 | 3440 | 2554 | 680 | 662 |
| Mut7.36-linker2-hFc(MFI) | 3463 | 3498 | 3498 | 3139 | 1250 | 735 | 522 |
| IL-2-linker2-hFc(MFI) | 3371 | 3451 | 3382 | 3619 | 1909 | 464 | 415 |
| Mut11.08-linker2-hFc(MFI) | 3451 | 3440 | 3668 | 3558 | 1365 | 462 | 366 |
| IL-2-linker2-hFc(MFI) | 3807 | 3731 | 3706 | 3833 | 1955 | 561 | 467 |
| Mut7.66-linker2-hFc(MFI) | 3718 | 3743 | 3280 | 2323 | 668 | 544 | 419 |
| Mut11.31-linker2-hFc(MFI) | 3570 | 3522 | 3428 | 2149 | 680 | 465 | 473 |

TABLE 15

STAT5 phosphorylation signal activated by IL-2 mutants in
CD4$^+$CD25$^-$FoxP3$^-$T cells detected by FACS

| Protein concentration (pM) | 10000 | 1000 | 100 | 10 | 1 | 0.1 |
|---|---|---|---|---|---|---|
| IL-2-linker2-hFc(MFI) | 1601 | 1370 | 1130 | 612 | 377 | 333 |
| Mut7.36-linker2-hFc(MFI) | 527 | 473 | 388 | 371 | 368 | 336 |

TABLE 15-continued

STAT5 phosphorylation signal activated by IL-2 mutants in
CD4$^+$CD25$^-$FoxP3$^-$T cells detected by FACS

| Protein concentration (pM) | 10000 | 1000 | 100 | 10 | 1 | 0.1 |
|---|---|---|---|---|---|---|
| IL-2-linker2-hFc(MFI) | 1111 | 960 | 833 | 485 | 362 | 370 |
| Mut11.08-linker2-hFc(MFI) | 718 | 584 | 496 | 382 | 355 | 354 |
| IL-2-linker2-hFc(MFI) | 1532 | 1361 | 1205 | 789 | 529 | 501 |
| Mut7.66-linker2-hFc(MFI) | 592 | 564 | 481 | 496 | 496 | 501 |
| Mut11.31-linker2-hFc(MFI) | 612 | 582 | 557 | 481 | 481 | 467 |

TABLE 16

STAT5 phosphorylation signal activated by IL-2
mutants in CD8$^+$ T cell detected by FACS

| Protein concentration (pM) | 10000 | 1000 | 100 | 10 | 1 | 0.1 |
|---|---|---|---|---|---|---|
| IL-2-linker2-hFc(MFI) | 973 | 413 | 274 | 221 | 233 | 239 |
| Mut7.36-linker2-hFc(MFI) | 270 | 264 | 245 | 247 | 259 | 236 |
| IL-2-linker2-hFc(MFI) | 758 | 381 | 321 | 260 | 270 | 288 |
| Mut11.08-linker2-hFc(MFI) | 336 | 295 | 296 | 281 | 286 | 294 |
| IL-2-linker2-hFc(MFI) | 910 | 481 | 372 | 361 | 344 | 339 |
| Mut7.66-linker2-hFc(MFI) | 326 | 344 | 319 | 331 | 343 | 346 |
| Mut11.31-linker2-hFc(MFI) | 311 | 324 | 346 | 327 | 326 | 317 |

Example 10—Regulatory Effect of IL-2 Mutants on T Cell Proliferation

The frozen PBMCs were thawed, re-suspended in RPMI-1640 (purchased from Gibco, Cat NO. A10491-01) containing 10% FBS (purchased from Gibco, Cat NO. 10099-141C), and cultured in a six-well plate pre-coated with 100 ng/ml CD3 antibody (purchased from BD, Cat NO. 566685) for two days. The cells were collected, washed three times with PBS buffer (purchased from Hyclone, Cat NO. SH30256.01), re-suspended in RPMI-1640 containing 10% FBS, and then cultured in a six-well plate for five days. The cells were then collected, washed once with PBS buffer, stained with Celltrace Violet (purchased from Invitrogen, Cat NO. C34557), washed once with culture medium, re-suspended with culture medium, added into a 24-well plate (900 μL cell per well), added with 100 μL of the IL-2 mutant protein samples and then cultured for seven days. The cells were then collected, re-suspended with PBS (purchased from Sangon Biotech, Cat NO. B548117-0500) containing 1% BSA (purchased from Sangon Biotech Cat NO. A500023-0100), and added into a 96-well plate.

The cells were stained with BV605-CD8 (purchased from Biolengend, Cat NO. 344742) at room temperature for 30 min, washed with PBS containing 1% BSA, fixed with 200 μL/well of fixing solution (purchased from eBioscience, Cat NO. 00-5523-00) at 4° C. for half an hour, and washed with PBS containing 1% BSA. The cells were then permeabilized with 200 μL/well of permeabilizing solution (purchased from eBioscience, Cat NO. 00-5523-00) at 4° C. for 30 minutes, and washed with PBS containing 1% BSA. The cells were further stained with APC-CY7-CD3 antibody (purchased from Biolengend, Cat NO. 344818), CD25 antibody (purchased from Biolengend, Cat NO. 302606) and Foxp3 antibody (purchased from ThermoFisher #17-4777-42) at room temperature for 30 minutes, washed with PBS containing 1% BSA, re-suspended in 200 μL PBS containing 1% BSA, and detected and analyzed by FACS (FACS Canto II, purchased from BD). The results are shown in FIG. 7A-FIG. 7F and Table 17-Table 19. The results show that, compared to wild-type IL-2, IL-2 mutants had similar effects on proliferation of Tregs, but slightly less effects on proliferation of $CD4^+CD25^-FoxP3^-T$ cells or $CD8^+T\ CD25^-T$ cells. The MFI in the following tables is the average fluorescence intensity value of Celltrace Violet in the detected cells, which was decreased in proliferated cells. That is, in the same detection time, the faster the cells proliferated, the lower the average fluorescence intensity was detected.

TABLE 17

Treg proliferation activated by IL-2 mutants detected by FACS

| Protein concentration (nM) | 10 | 1 | 0.1 | 0.01 | 0.001 | 0.0001 | 0.00001 |
|---|---|---|---|---|---|---|---|
| IL-2-linker2-hFc(MFI) | 1995 | 1670 | 2857 | 3362 | 3624 | 3863 | 4518 |
| Mut7.36-linker2-hFc(MFI) | 1823 | 1407 | 2070 | 3162 | 3555 | 4077 | 4389 |
| Mut7.66-linker2-hFc(MFI) | 1583 | 1437 | 2068 | 3384 | 4392 | 4027 | 4887 |
| IL-2-linker2-hFc(MFI) | 1807 | 1838 | 2651 | 3319 | 3459 | 3691 | 4758 |
| Mut11.08-linker2-hFc(MFI) | 1633 | 1536 | 1884 | 2371 | 2930 | 3369 | 3953 |
| Mut11.31-linker2-hFc(MFI) | 1735 | 1855 | 1985 | 2669 | 2626 | 3379 | 4323 |

TABLE 18

$CD4^+CD25^-FoxP3^-T$ cell proliferation activated by IL-2 mutants detected by FACS

| Protein concentration (nM) | 10 | 1 | 0.1 | 0.01 | 0.001 | 0.0001 | 0.00001 |
|---|---|---|---|---|---|---|---|
| IL-2-linker2-hFc(MFI) | 1653 | 2058 | 2216 | 3198 | 4578 | 5274 | 5602 |
| Mut7.36-linker2-hFc(MFI) | 2361 | 2372 | 3317 | 4169 | 4971 | 5319 | 5815 |
| Mut7.66-linker2-hFc(MFI) | 2258 | 2524 | 3160 | 4633 | 5374 | 5495 | 6022 |
| IL-2-linker2-hFc(MFI) | 1679 | 1838 | 2055 | 2728 | 3997 | 4826 | 5314 |
| Mut11.08-linker2-hFc(MFI) | 2254 | 2166 | 2538 | 3372 | 4154 | 5072 | 5391 |
| Mut11.31-linker2-hFc(MFI) | 2332 | 2559 | 2885 | 3878 | 4779 | 5284 | 5509 |

TABLE 19

$CD8^+T\ CD25^-T$ cell proliferation activated by IL-2 mutants detected by FACS

| Protein concentration (nM) | 10 | 1 | 0.1 | 0.01 | 0.001 | 0.0001 | 0.00001 |
|---|---|---|---|---|---|---|---|
| IL-2-linker2-hFc(MFI) | 1128 | 1422 | 1696 | 3303 | 4907 | 5767 | 6303 |
| Mut7.36-linker2-hFc(MFI) | 1955 | 1921 | 2640 | 3732 | 4917 | 5562 | 6179 |
| Mut7.66-linker2-hFc(MFI) | 1820 | 1983 | 2683 | 4038 | 5539 | 5553 | 6617 |
| IL-2-linker2-hFc(MFI) | 1064 | 1236 | 1435 | 2497 | 4087 | 5010 | 5715 |
| Mut11.08-linker2-hFc(MFI) | 1876 | 1682 | 1956 | 2965 | 4124 | 5195 | 5567 |
| Mut11.31-linker2-hFc(MFI) | 1750 | 1945 | 2252 | 3463 | 4610 | 5406 | 5583 |

Example 11. Regulatory Effect of IL-2 Mutants on NK Cell Proliferation

Figure 8:
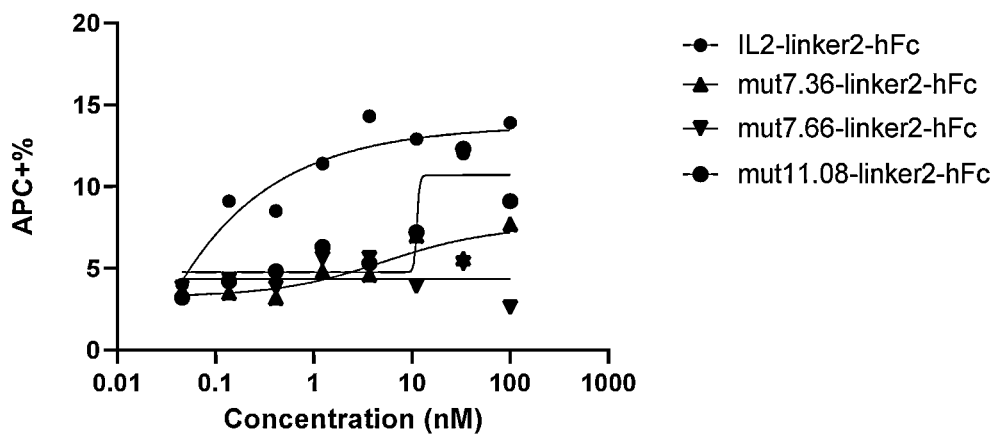
FIG. 8 shows the effect of IL-2 mutant protein on the level of proliferation of NK cells.
Figure 9A:
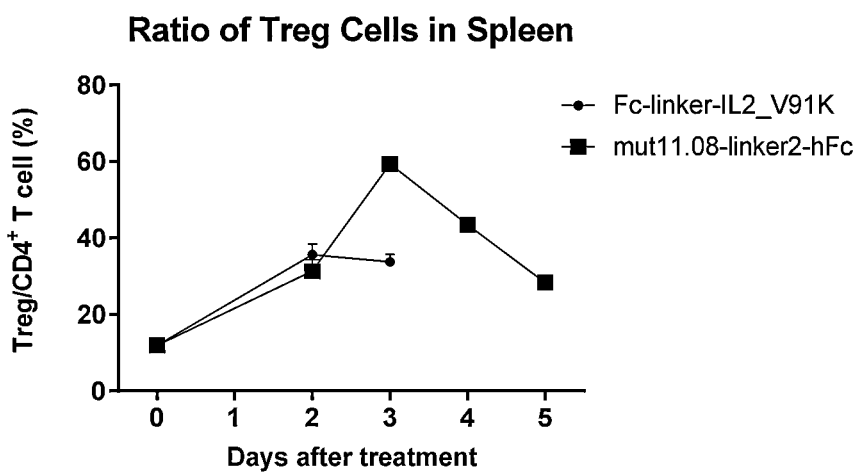
FIG. 9A shows the percentage of Tregs in CD4$^+$ T cells in the spleen.
Figure 9B:
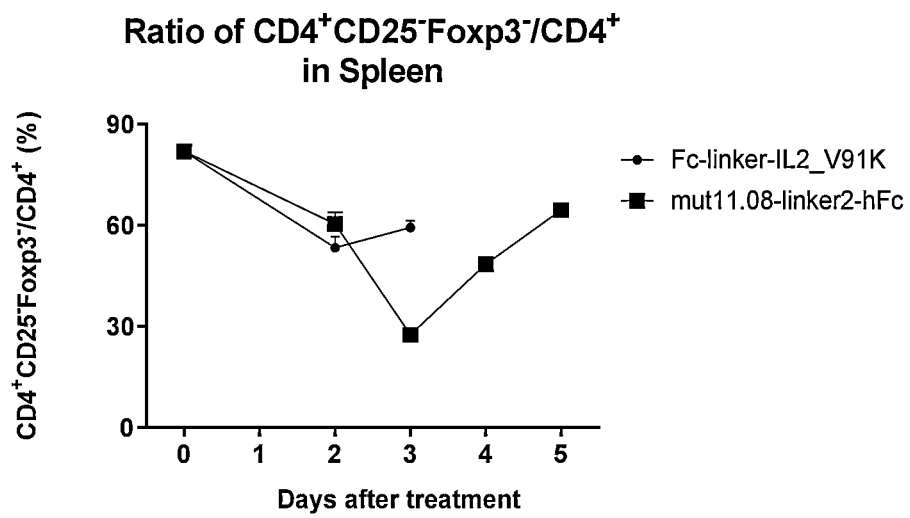
FIG. 9B shows the percentage of CD4$^+$CD25$^-$Foxop3$^-$ cells in CD4$^+$ cells in the spleen.
Figure 9C:
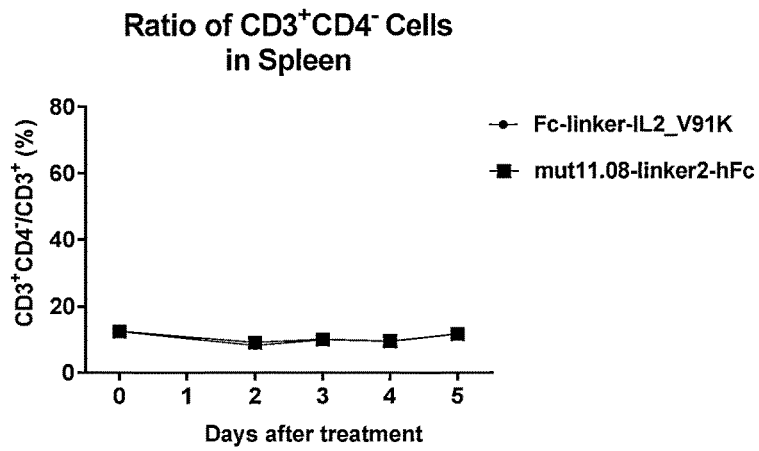
FIG. 9C shows the percentage of CD3$^+$CD4$^-$ cells in CD3$^+$ cells in the spleen.
Figure 10A:
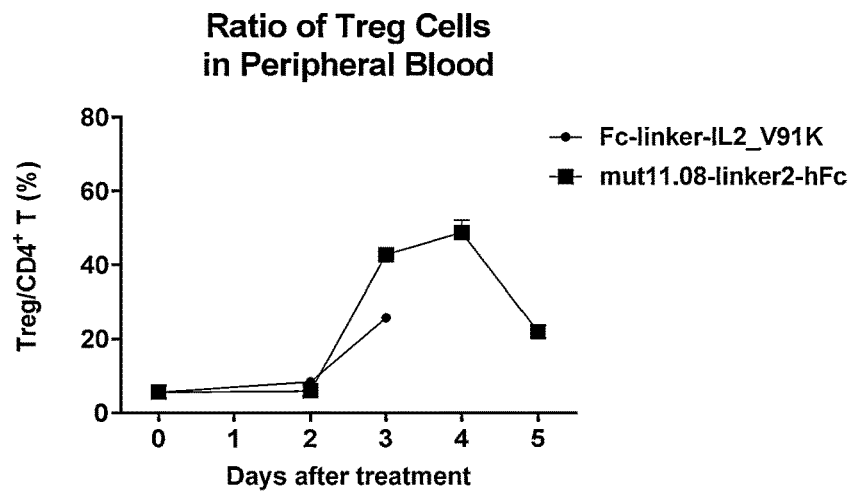
FIG. 10A shows the percentage of Tregs in CD4$^+$ cells in peripheral blood.
Figure 10B:
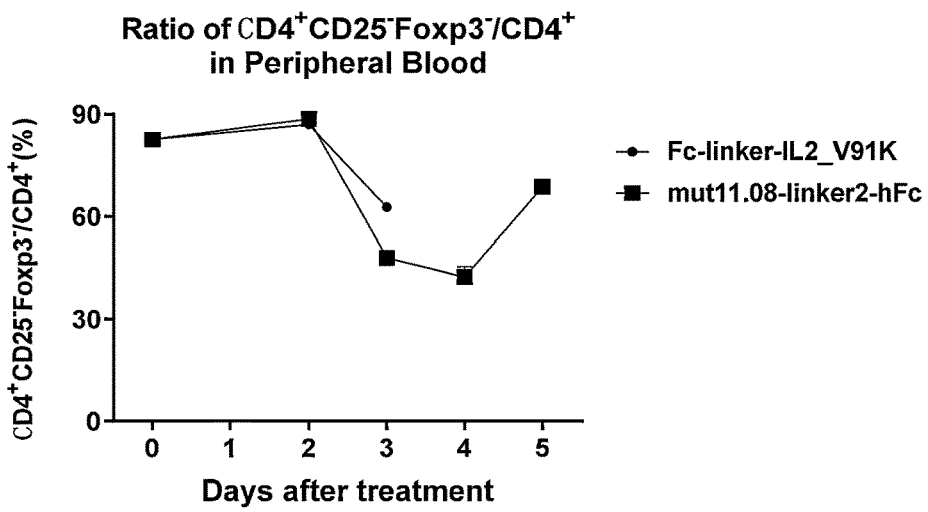
FIG. 10B shows the percentage of CD4$^+$CD25$^-$Foxop3$^-$ cells in CD4$^+$ cells in peripheral blood.
Figure 10C:
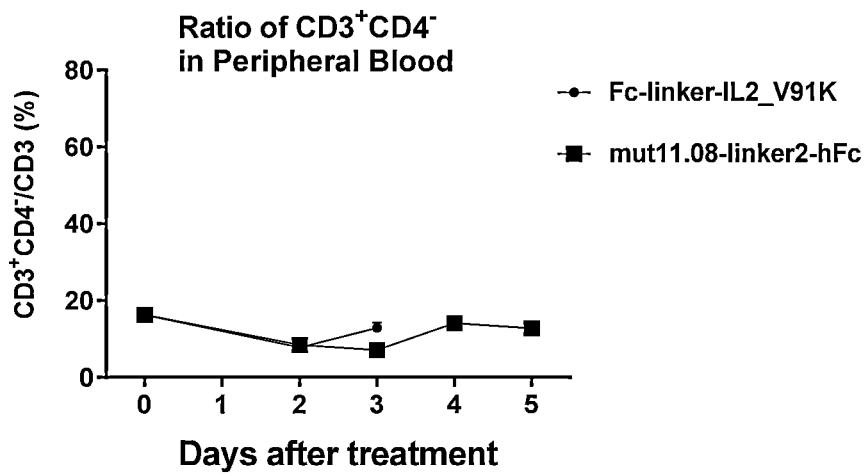
FIG. 10C shows the percentage of CD3$^+$CD4$^-$ cells in CD3$^+$ cells in peripheral blood.

NK cells were sorted and counted using an NIK sorting kit (purchased from Miltenyi Biotec, Cat NO. 130-092-657), and then re-suspended in MEM medium (purchased from Gibco, Cat NO. 12634-010) comprising 25% bovine serum (purchased from Gibco, Cat NO. 10099-141C), 0.2 mM inositol (purchased from Sigma Aldrich, Cat NO. I7508-50G), 0.1 mM β-mercaptoethanol (purchased from Sigma Aldrich, Cat NO. M3148-100ML), and 0.02 mM folic acid (purchased from Sigma Aldrich, Cat NO. F8758-5G). The cells were seeded into a 96-well plate added with Fc blocker (purchased from Biolengend, Cat NO. 422302) and an IL-2 mutant in each well, and cultured for three days. BrdU (purchased from Biolengend, Cat NO. 423401) was added at the last 18 hours. The cells were collected, washed and re-suspended with PBS containing 1% BSA, fixed with an equal volume of 4% paraformaldehyde (purchased from DingGuo, Cat NO. AR-0211) at room temperature for 30 minutes, and washed with PBS containing 1% BSA. The cells were permeabilized with 0.5% Triton-X 100 (purchased from Thermo Fisher, Cat NO. HFH10) at room temperature for 15 minutes, washed with PBS containing 1% BSA, and digested with Dnase I (purchased from Sigma Aldrich, Cat NO. D4513-1VL) at 37° C. for one hour. The cells were washed and re-suspended with PBS containing 1% BSA, stained with APC anti-BrdU antibody (purchased from Biolengend, Cat NO. 339808) at room temperature for 20 minutes, and washed with PBS containing 1% BSA. The samples were re-suspended in 200 μL of PBS containing 1% BSA, detected and analyzed by FACS (FACS Canto II, purchased from BD). The results are shown in FIG. 8 and Table 20. The results show that, compared to wild-type IL-2, the effect of IL-2 mutants on NK cell proliferation was significantly reduced. The data in Table 20 is the proportion of BrdU positive cells in the NK cell population.

```
CLVKGFYPSDIAVEWESNGQPENNYKTTPPVLDSDGSFFLYSKLTVDKSR

WQQGNVFSCSVMHEALHNHYTQKSLSLSPGGGGGSAPTSSSTKKTQLQLE

HLLLDLQMILNGINNYKNPKLTRMLTFKFYMPKKATELKHLQCLEEELKP

LEEVLNLAQSKNFHLRPRDLISNINKIVLELKGSETTFMCEYADETATIV

EFLNRWITFAQSIISTLT
```

The whole blood of mice was collected in a 2 mL EDTA/2K anticoagulant tube (Xinkang Medical, Cat. No. X424), and well mixed with the anticoagulant by upside down tilting the tube for full contact. 300 μL of whole blood was transferred to a FACS tube, which was added with a mixed solution of staining antibodies and incubated at room temperature in the dark for 20 min. The sample was then added with red blood cell lysis buffer (1 mL per sample) (Hybri-Max Cat. No. R7757-100 mL) and allowed to stand at room temperature in the dark for 5 min, and floccules were observed. The sample was then centrifuged at 400 g for 6 min at 20° C. After the supernatant was discarded, the cells were dispersed. Red blood cell lysis was repeated. Cell washing: the cells were re-suspended in PBS (4 mL per sample) and centrifuged at 500 g for 6 min at 4° C.; the supernatant was discarded; and the cells were dispersed. Fixation buffer (500 μL per tube) was added into the tube drop by drop, while shaking the FACS tube intermittently after each addition. The sample was fixed at 4° C. for an hour or overnight.

The spleens of mice were milled on a 70 m cell strainer (Falcon Corning, Cat. No. 352350) and centrifuged at 500 g. Each spleen was added with 3 mL red blood cell lysis buffer and lysed for 5 min, and then added with 20 mL PBS to terminate the lysis. The mixture was centrifuged at 500 g for 5 min. The cells were re-suspended with 5 mL PBS and screened by a 70 m cell strainer. After cell counting, 1×10$^6$

TABLE 20

NK cell proliferation activated by IL-2 mutants detected by FACS

| Protein concentration (nM) | 100.00 | 33.33 | 11.11 | 3.70 | 1.23 | 0.41 | 0.14 | 0.05 |
|---|---|---|---|---|---|---|---|---|
| IL-2-linker2-hFc(APC+%) | 13.9 | 12.0 | 12.9 | 14.3 | 11.4 | 8.5 | 9.1 | 4.0 |
| Mut7.36-linker2-hFc(APC+%) | 7.7 | 5.6 | 7.0 | 4.6 | 4.8 | 3.2 | 3.5 | 3.6 |
| Mut7.66-linker2-hFc(APC+%) | 2.6 | 5.3 | 3.9 | 5.6 | 5.6 | 3.8 | 4.3 | 3.8 |
| Mut11.08-linker2-hFc(APC+%) | 9.1 | 12.3 | 7.2 | 5.3 | 6.3 | 4.8 | 4.2 | 3.2 |

Example 12. Pharmacodynamics (PD) Results in Wild-Type Mice after Subcutaneous Administration Balb/c mice, female, 6-8 weeks old, were purchased from Vital River. Fc-linker-IL2_V91K and mut11.08-linker2-hFc were diluted with PBS and administered subcutaneously to the back of mice at 200 μL per mouse. After administration, the whole blood and spleen samples of mice were collected at different time points for FACS analysis. The sequence of Fc-linker-IL2_V91K is as shown in SEQ ID NO: 60, which was purified as described in Example 2.

```
                                        (SEQ ID NO: 60)
PKSSDKTHTCPPCPAPELLGGPSVFLFPPKPKDTLMISRTPEVTCVVVDV

SHEDPEVKFNWYVDGVEVHNAKTKPCEEQYGSTYRCVSVLTVLHQDWLNG

KEYKCKVSNKALPAPIEKTISKAKGQPREPQVYTLPPSRDELTKNQVSLT
``` cells were added into each FACS tube. After Fc Blocker (5 μL per tube) (Biolengend, Cat. No. 156 603) was added, the cells were vortexed and incubated at 4° C. for 20 min (vortexed every 10 min). The cells were then added with FACS washing buffer (4 mL per tube) (PBS+1% BSA) and centrifuged at 400 g for 6 min at 4° C. The supernatant was discarded and the mouth of the tube was dried with absorbent paper. The cells were added with Anti-Mouse CD3e (BD Bioscience, Cat. No. 740014), Anti-Mouse CD4 (BD Bioscience, Cat. No. 553407) and Anti-mouse CD25 (Biolengend, Cat. No. 102008), vortexed and incubated at 4° C. for 20 min (vortexed every 10 min). The cells were then added with FACS washing buffer (4 mL per tube) and centrifuged at 400 g for 6 min at 4° C. The supernatant was discarded and the mouth of the tube was dried with absorbent paper. After vortexing once, fixation buffer (500 μL per tube) was added into the tube drop by drop, while shaking the tube intermittently after each addition. The sample was fixed at 4° C. for an hour or overnight.

Fixation buffer: Fixation/Permeabilization Concentrate and Fixation/Permeabilization Diluent in Set3901 (eBioscience, Cat. No. 00-5523-00) were mixed in a ratio of 1:3 to prepare the fixation buffer.

Permeabilization buffer and ddH$_2$O were mixed well in a ratio of 1:9 to prepare the permeabilization solution. The cells were added with the permeabilization solution (2 mL per tube) and centrifuged at 500 g for 6 min at 4° C. The supernatant was discarded and the mouth of the tube was dried with absorbent paper. The permeabilization process was repeated with permeabilization solution (3 mL per tube). The cells were added with Foxp3 antibodies (10 µL per tube) (eBioscience, Cat. No. 25-5773-82) and kept at 4° C. for 40 min (vortexed every 20 min). The cells were then added with FACS buffer (4 mL per tube) and centrifuged at 500 g for 6 min at 4° C. The supernatant was discarded and the mouth of the tube was dried with absorbent paper. After vortexing once, 100 µL FACS buffer was added into the tube to re-suspend the cells for detection. The percentages of Tregs (CD4$^+$ CD25$^+$ Foxp3$^+$), CD4$^+$ CD25$^-$ Foxp3$^-$ and CD3$^+$CD4$^-$ T cells in groups of animals were represented as mean±standard deviation (Mean±SEM), and graphed and analyzed by Graphpad Prism 5 software.

As shown in FIG. 9A-9C and FIG. 10A-10C, when being administered subcutaneously at a single dose of 1 mpk, mut11.08-linker2-hFc significantly increased the percentage of Tregs and decreased the percentage of CD4$^+$CD25$^-$ Foxp3$^-$ T cells in the spleen and peripheral blood of mice. The percentage of CD3$^+$CD4$^-$ T cells was not significantly changed. The efficacy of mut11.08-linker2-hFc was better than that of Fc-linker-IL2_V91K.

Example 13. Wild-Type Mice DTH (Delayed-Type Hypersensitivity) Model

Sensitization phase: Antigens were emulsified with 3 mg/mL KLH (Sigma, Cat. No. H7017, 50 mg), IFA (Sigma, Cat. No. F5506, 10 mL) and CFA (Sigma, Cat. No. F5581, 10 mL) in a volume ratio of 1:1:1 by using the Double-hubbed needle method. The antigens could be fully emulsified to form a viscous emulsion in about 1 hour. Each mouse was injected with 100 µL emulsifier, that is, 100 µg KLH. Each mouse was injected subcutaneously with emulsified KLH at two sites (50 µL at each site) in the middle part of scapula. At the same time, the mice were injected subcutaneously with WT IL-2-linker2-hFc (WT IL-2, SEQ ID NO: 12), Fc-linker-IL2_V91K or mut11.08-linker2-hFc at a dose of 1 mpk, 200 µL per mouse, once every 3 days, as WT IL-2-linker2-hFc, Fc-linker-IL2_V91K and mut11.08-linker2-hFc group, respectively; the mice were injected intraperitoneally with cyclosporin A (CsA, Sigma, Cat. No. F5581, 10 mL) at a dose of 10 mpk, 200 µL per mouse, once per day, as CsA group; the mice were injected intraperitoneally with PBS as vehicle control group.

Stimulation was performed on the 5th day after sensitization. 10 mg/mL KLH was diluted to 1 µg/µL by 10 times with PBS. Each mouse was injected intradermally with 10 µL KLH (i.e., g KLH) on right ear and 10 µL PBS on left ear as control.

Before sensitization, the left and right ears thickness of each mouse was measured by a spiral micrometer (0-25 mm, accuracy: 0.001, purchased from Nanjing SuCe Measuring Instruments Co., Ltd) and recorded. Before stimulation, the left and right ears thickness of each mouse was measured with the spiral micrometer as a baseline value. The ear thickness was measured at 24 h, 48 h, 72 h, and 96 h after stimulation. The changes of body weight and ear thickness in each group were represented as mean±standard deviation (Mean±SEM), and graphed and analyzed by Graphpad Prism 5 software.

Figure 11A:
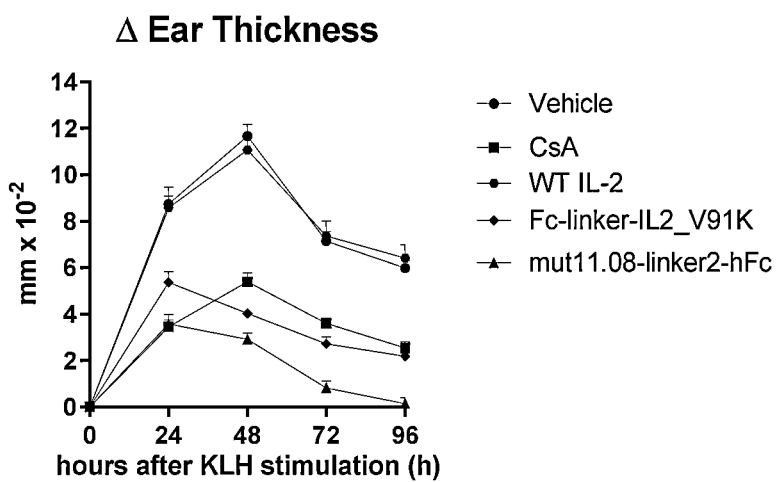
FIG. 11A shows the change of Δ ear thickness in different groups of wild-type mice DTH models, wherein Δ ear thickness refers to the change of thickness of the right ear before and after stimulation.
Figure 11B:
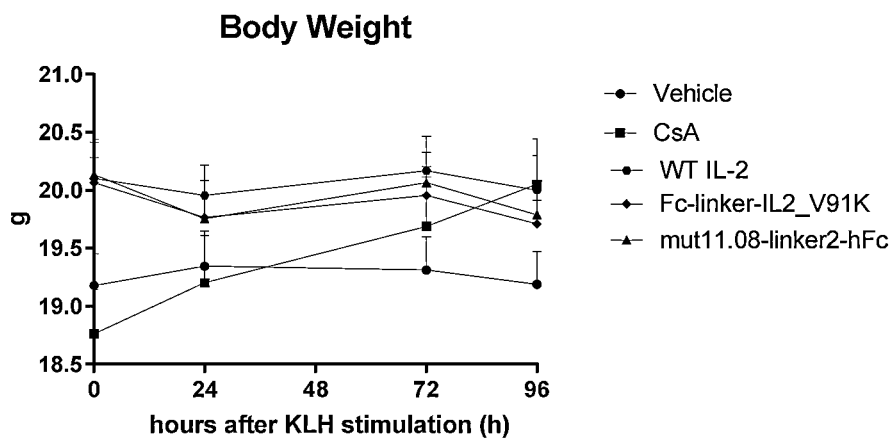
FIG. 11B shows the change of body weight in different groups of wild-type mice DTH models.

The result is shown in FIG. 11A. After a single subcutaneous administration of 1 mpk, compared to the vehicle control group, the change of Δ ear thickness in WT IL-2 group was not significant, while the Δ ear thickness of mice in mut11.08-linker2-hFc group became less, which suggests the anti-inflammatory effect of mut11.08-linker2-hFc, and the anti-inflammatory efficacy of mut11.08-linker2-hFc is better than that of Fc-linker-IL2_V91K and CsA. As shown in FIG. 11B, there was no significant change in the body weight of animals in the groups.

Figure 12A:
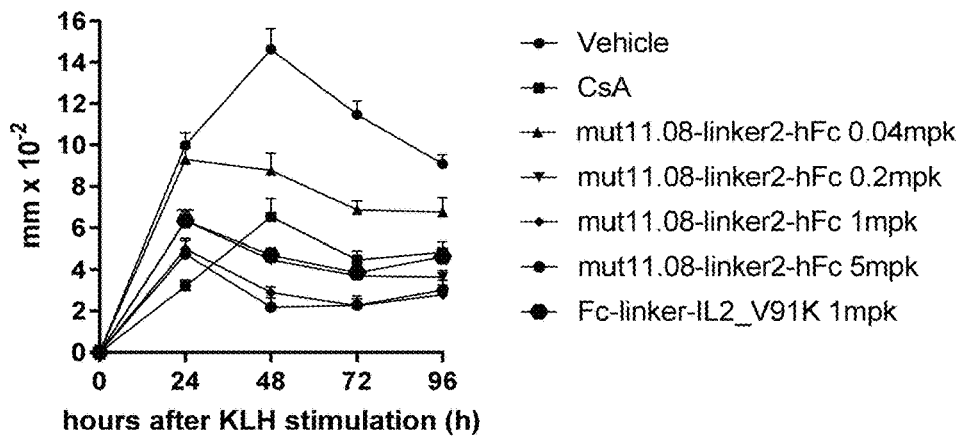
FIG. 12A shows the change of Δ ear thickness in different groups of wild-type mice DTH models, wherein Δ ear thickness refers to the change of thickness of the right ear before and after stimulation.
Figure 12B:
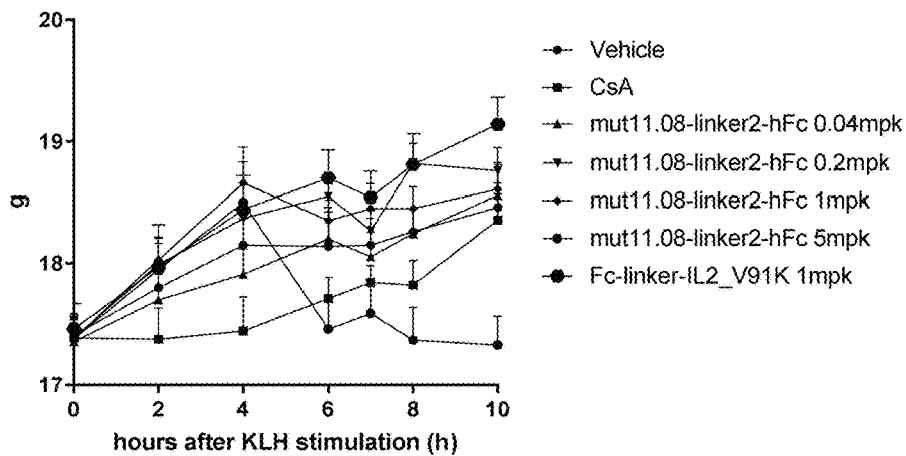
FIG. 12B shows the change of body weight in different groups of wild-type mice DTH models.
Figure 13A:
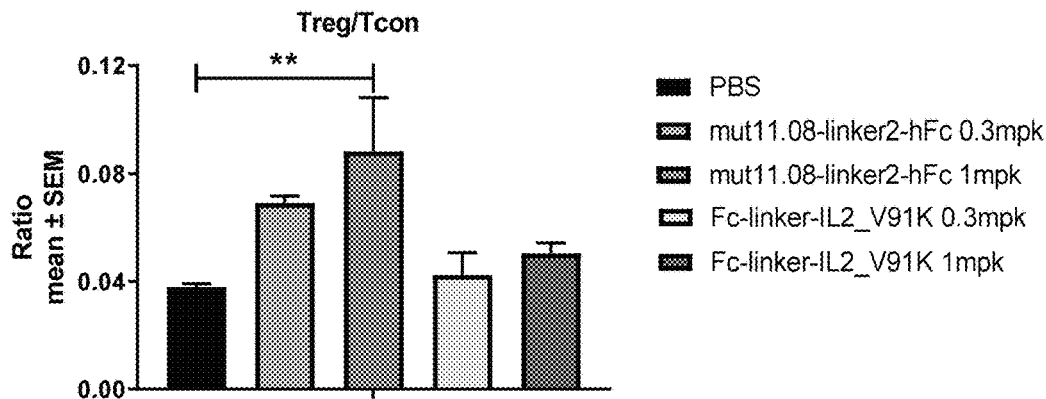
FIG. 13A shows Treg/Tcon in different groups of NOG mice.
Figure 13B:
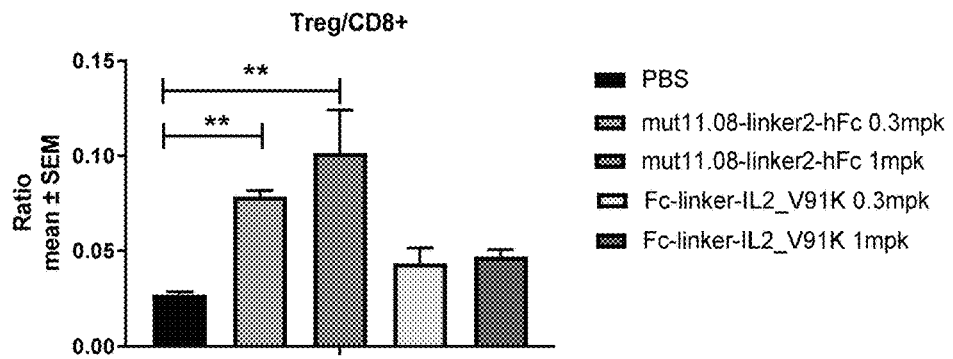
FIG. 13B shows Treg/CD8$^+$ in different groups of NOG mice.
Figure 14A:
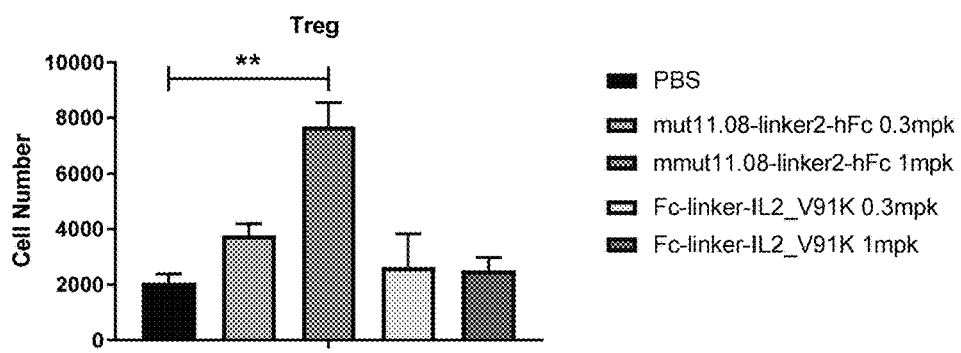
FIG. 14A shows the number of Tregs in different groups of NOG mice.
Figure 14B:
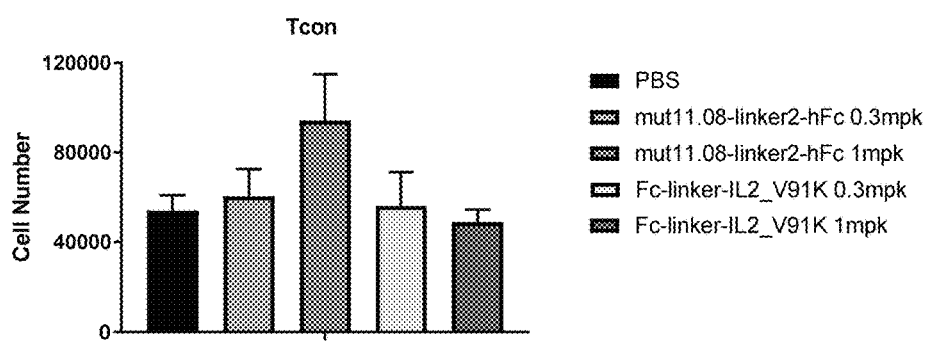
FIG. 14B shows the number of Tcons in different groups of NOG mice.
Figure 14C:
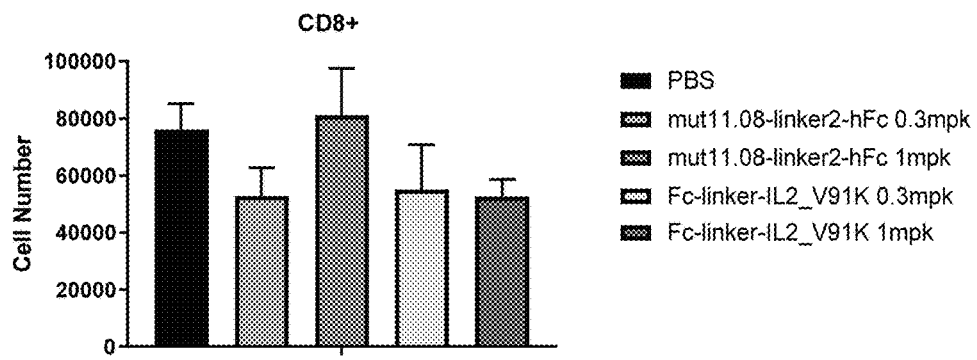
FIG. 14C shows the number of CD8$^+$ cells in different groups of NOG mice.

The results of the second round of experiments are shown in FIG. 12A. A single dose of Fc-linker-IL2_V91K (1 mpk) was administered subcutaneously, while mut11.08-linker2-hFc was administered subcutaneously at a single dose of 0.04, 0.2, 1 or 5 mpk. The anti-inflammatory effect of mut11.08-linker2-hFc was dose dependent. 0.2 mpk mut11.08-linker2-hFc had the same effect as 1 mpk Fc-linker-IL2_V91K, and no abnormality in body weight was observed under this condition. As shown in FIG. 12B, when 5 mpk mut11.08-linker2-hFc was administrated, the body weight of mice fluctuated and decreased, while the body weight of other groups was normal.

Example 14. PD Results in PBMC Mice after Subcutaneous Administration

NOG mice, female, 11-12 weeks old, were purchased from Vital River. On Day 1, PBMCs were thawed, activated by adding CD3 (purchased from eBioscience, Cat. No. 16-0037-85/2106800, with a final concentration of 12.5 ng/mL) and CD28 (purchased from eBioscience, Cat. No. 16-0289-85/2073954, with a final concentration of 25 ng/mL) and incubated overnight in a 5% CO$_2$ incubator at 37° C. for 16 hours. PBMCs (20×10$^6$ per mouse, 400 µL) were collected on Day 0 and inoculated into NOG mice by tail veins. The inoculated mice were randomly divided into five groups based on body weight, including PBS control group, mut11.08-linker2-hFc groups (0.3 mpk, 1 mpk) and Fc-linker-IL2_V91K groups (0.3 mpk, 1 mpk), with 3 mice in each group. The drug was then injected subcutaneously into the neck (Day 0) in a single dose. On Day 3 after administration, the spleen of euthanized mice was taken for FACS analysis, and data were recorded. The number and the fold change of Tregs (CD4$^+$ CD25$^+$ Foxp3$^+$), Tcons (CD4$^+$ CD25$^-$) and CD8$^+$ T cells in the groups of animals were graphed and analyzed by Graphpad Prism 8 software.

The experimental results are shown in FIG. 13A-13B and FIG. 14A-14C. After a single subcutaneous administration of 1 mpk, mut11.08-linker2-hFc increased the ratio of Treg/Tcon and the ratio of Treg/CD8$^+$T on day 3 in a dose-dependent manner and showed a better result than Fc-linker-IL2_V91K. On Day 3 after administration, except for the significant change in the number of Tregs, the number of Tcons increased but was not significant, and the number of CD8$^+$T cells did not change significantly.

Example 15. PBMC Mice Graft-Versus-Host Disease (GVHD) Model

NOG mice, females, 13-14 weeks old, were purchased from Vital River. The protocol was same as Example 14. The NOG mice were randomly divided into three groups based on body weight, including G1 group (PBS, no activated PBMCs were inoculated, 3 mice), G2 group (PBS, 10 mice)

and G3 group (0.2 mpk mut11.08-linker2-hFc was given, 10 mice), wherein G2 and G3 groups were inoculated with activated PBMCs according to Example 14. The drug was then injected subcutaneously into the neck (Day 0) in a single dose. The mice were weighed twice per week, and scored after the appearance of GVHD characteristics [Scoring System: weight loss (0: <10%, 1: 10%-20%, 2: >20%, 3: >30%); anemia (0: red or pink tail, 1: white tail); posture (0: normal, 1: hunchback); general activities (0: normal, 1: limited); shedding (0: without shedding, 1: shedding) and jaundice (0: white or red tail, 1: yellow tail); the maximum disease severity or death corresponds to 8]. The data were recorded. Note: 1. If a mouse gets the maximum disease severity score, other symptoms will not be scored; 2. After death, the dead mice were continually scored until the end of the experiment.

Figure 15A:
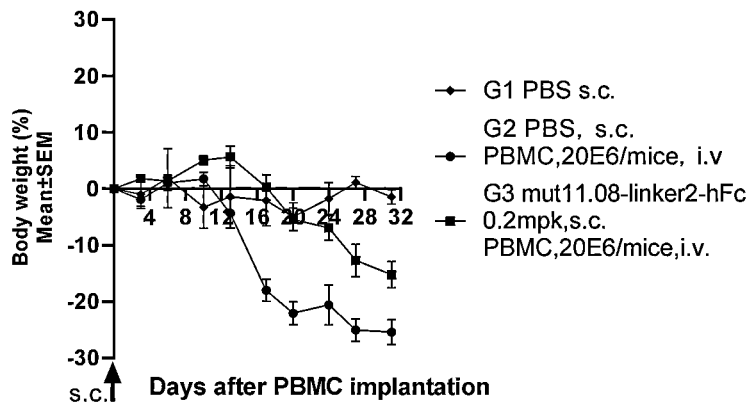
FIG. 15A shows the change of body weight in different groups of NOG mice.
Figure 15B:
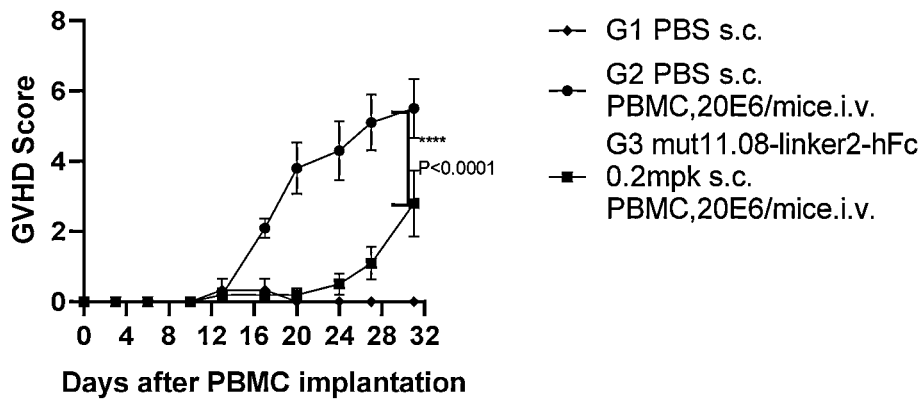
FIG. 15B shows the GVHD scores in different groups of NOG mice.

The experimental results are shown in FIG. 15A-15B.13 days after PBMCs inoculation, the body weight of the G2 group decreased, and GVHD symptoms occurred early in the G2 group. 17 days after PBMCs inoculation, the body weight of the G3 group decreased, and the overall weight loss of the G3 group was less than that of the G1 group, and the weight loss of the G3 group occurred later than that of the G2 group, which suggests mut11.08-linker2-hFc effectively inhibits the occurrence of GVHD in mice in accordance with pharmacological expectation. The mut11.08-linker2-hFc showed no toxic and side effects at 0.2 mpk, and good anti-GVHD ability, according to the body weight assessment. In addition, the animal mortality and GVHD score of the G3 group were lower than those of the G2 group, and there were significant differences.

Example 16. Pharmacokinetics in Mice

The method for determining the plasma drug concentration in mice in this example was as follows: The plate was coated with 1 μg/mL hIL2R alpha protein (ACROBiosystems, Cat. No. ILA-H52H9-100 μg). A standard curve formed with drugs in blank serum at concentrations ranging from 500 to 3.90625 ng/mL. Quality controls with high/medium/low concentrations were prepared, and all samples to be detected, standards and the quality controls were diluted 40 times with diluents and then added into a plate in duplicate (100 μl/well) (samples can be diluted additionally, according to the actual situation). The detection antibody Peroxidase AffiniPure Mouse Anti-Human IgG, Fc γ fragment specific (Jackson, Cat. No. 209-035-098) was diluted 10000 times and then added into the plate. The TMB chromogenic solution was added into the plate (100 μl/well) for color development, which was then stopped by using 1 M sulfuric acid (50 μl/well).

Figure 16A:
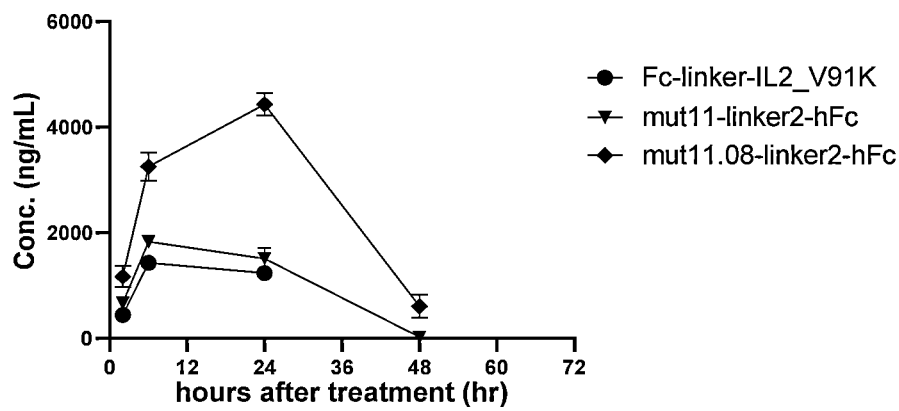
FIG. 16A shows the plasma drug concentration in wild-type mice after subcutaneous administration.
Figure 16B:
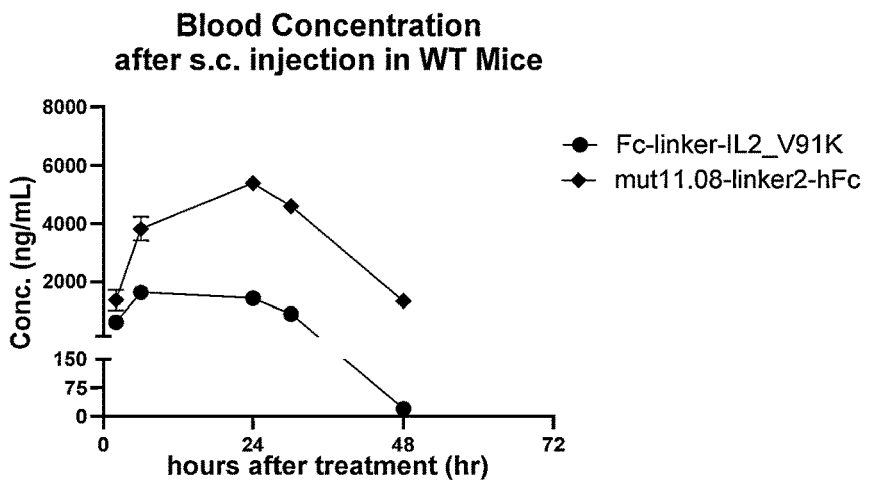
FIG. 16B shows the plasma drug concentration in wild-type mice after subcutaneous administration.

The plasma drug concentration in wild-type mice was determined after subcutaneous administration (1 mpk). The two experimental results are shown in FIG. 16A-16B and Table 21-22. In both experiments, the exposure amount of mut11.08-linker2-hFc was 4-6 times higher than that of Fc-linker-IL2_V91K (control group), and the $T_{max}$ was delayed compared to Fc-linker-IL2_V91K. The exposure amount of mut11.08-linker2-hFc was higher than that of mut11-linker2-hFc after a single subcutaneous administration (1 mpk).

TABLE 21

Pharmacokinetic parameters in wild-type mice after a single subcutaneous administration

| Mean | $T_{1/2}$ (h) | $T_{max}$ (h) | $C_{max}$ (ng/mL) | AUClast (h*ng/mL) |
|---|---|---|---|---|
| Fc-linker-IL2_V91K | NA* | 6.00 | 1,430.94 | 28,208.77 |
| mut11-linker2-hFc | NA* | 12.00 | 1843.32 | 43,254.14 |
| mut11.08-linker2-hFc | NA* | 24.00 | 4,433.17 | 139,652.97 |

TABLE 22

Pharmacokinetic parameters in wild-type mice after a single subcutaneous administration

| Mean | $T_{1/2}$ (h) | $T_{max}$ (h) | $C_{max}$ (ng/mL) | AUClast (h*ng/mL) |
|---|---|---|---|---|
| Fc-linker-IL2_V91K | NA* | 6.00 | 1628.30 | 42,874.91 |
| mut11.08-linker2-hFc | 11.51 | 24.00 | 5,391.62 | 177,902.19 |

Figure 17:
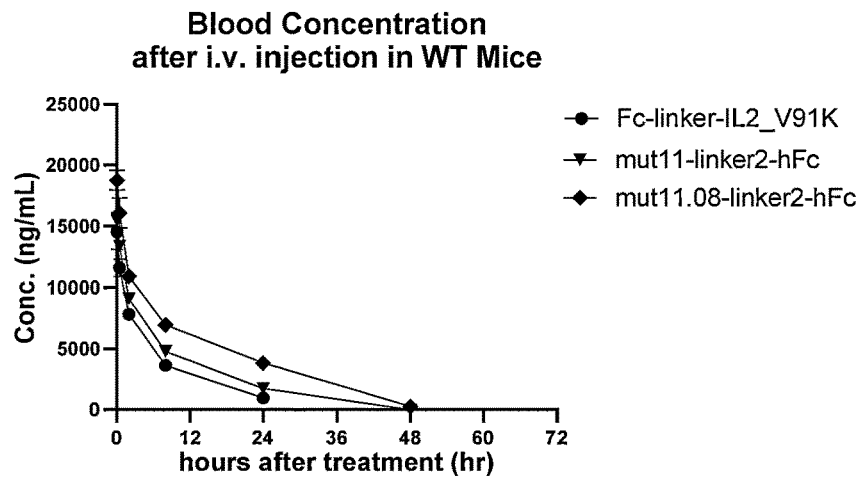
FIG. 17 shows the plasma drug concentration in wild-type mice after intravenous administration.

The plasma drug concentration in wild-type mice was determined after intravenous administration (1 mpk). The results are shown in FIG. 17 and Table 23. The exposure amount of mut11.08-linker2-hFc was higher than that of Fc-linker-IL2_V91K, but the difference became smaller ($C_{max}$: 3×→1.3×, AUC: 4×→2.4×) compared to subcutaneous administration. The exposure amount of mut11.08-linker2-hFc was higher than that of mut11-linker2-hFc, but the difference became smaller ($C_{max}$: 2.4×→1.2×, AUC: 3.2×→1.6×) compared to subcutaneous administration.

Therefore, the bioavailability of mut11.08-linker2-hFc administered subcutaneously was better than that of Fc-linker-IL2_V91K and mut11-linker2-hFc. Stability mutations increased drug exposure and bioavailability.

TABLE 23

Pharmacokinetic parameters in wild type mice after a single intravenous administration

| Mean | $T_{1/2}$ (h) | $T_{max}$ (h) | $C_{max}$ (ng/mL) | AUClast (h*ng/mL) |
|---|---|---|---|---|
| Fc-linker-IL2_V91K | 7.35 | 0.08 | 14,518.61 | 92,522.67 |
| mut11-linker2-hFc | 5.27 | 0.08 | 15,450.84 | 138,450.96 |
| mut11.08-linker2-hFc | 8.41 | 0.08 | 18,761.22 | 217851.01 |

Figure 18:
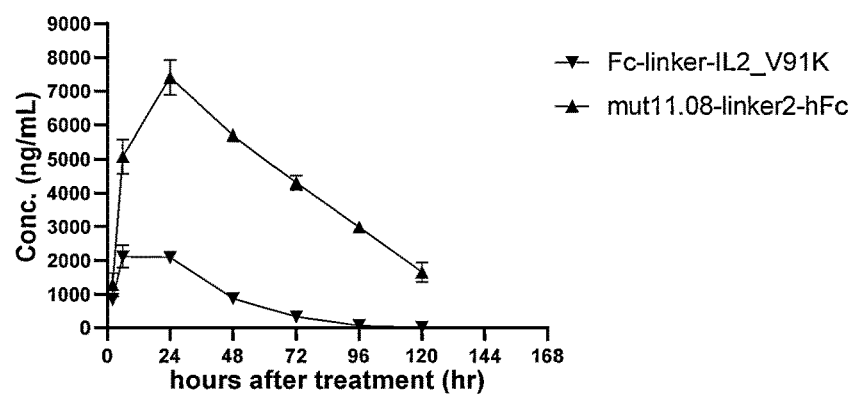
FIG. 18 shows the plasma drug concentration in mice inoculated with PBMCs after subcutaneous administration.

Mice were inoculated with PBMCs by the method described in Example 14. The plasma drug concentration in wild-type mice was determined after subcutaneous administration (1 mpk). The results are shown in FIG. 18 and Table 24. In PBMCs mice, after a single subcutaneous administration (1 mpk), the exposure amount of mut11.08-linker2-hFc showed an obvious advantage, which was 5-8 times higher than that of Fc-linker-IL2_V91K, and $T_{max}$ of mut11.08-linker2-hFc was later than that of Fc-linker-IL2_V91K.

TABLE 24

Pharmacokinetic parameters in PBMC mice after a single subcutaneous administration

| Mean | $T_{1/2}$ (h) | $T_{max}$ (h) | $C_{max}$ (ng/mL) | AUClast (h*ng/mL) |
|---|---|---|---|---|
| Fc-linker-IL2_V91K | 12.29 | 12.00 | 2,338.82 | 99848.69 |
| mut11.08-linker2-hFc | 43.06 | 24.00 | 7,405.26 | 546719.71 |

Example 17. Pharmacokinetics and PD Results in Cynomolgus Monkeys

The method for determining the plasma drug concentration of cynomolgus monkeys in this example was as follow: The plate was coated with 1 μg/mL hIL2R alpha protein (ACROBiosystems, Cat. No. ILA-H52H9-100 μg). A standard curve was formed with drugs in blank serum from cynomolgus monkey at concentrations ranging from 15-0.11718 ng/mL. Quality controls with high/medium/low concentrations were prepared, and all samples to be detected, standards and the quality controls were diluted to 5 times and then added into the plate in duplicate (100 μl/well). The detection antibody Goat Anti-Human IgG, Monkey ads-BIOT (SoutherBiotech, Cat. No. 2049-08) was diluted 1000 times and then added into the plate, and then Streptavidin-HRP (Thermo, Cat. No. 21126) diluted 5000 times was added into the plate. Finally, the TMB chromogenic solution (100 μl/well) was added for color development, which was then stopped by using 1M sulfuric acid (50 μl/well). Cynomolgus monkey blank serum was purchased from Shanghai HkeyBio Technology Co., Ltd.

Figure 19:
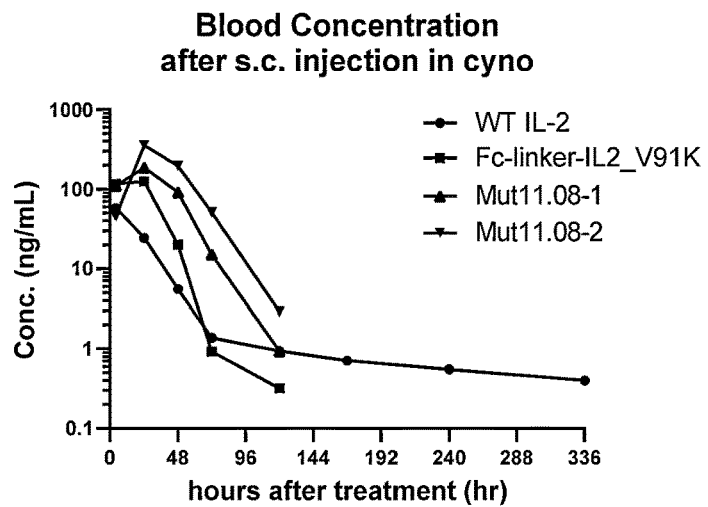
FIG. 19 shows the plasma drug concentration in cynomolgus monkey after subcutaneous administration.
Figure 20A:
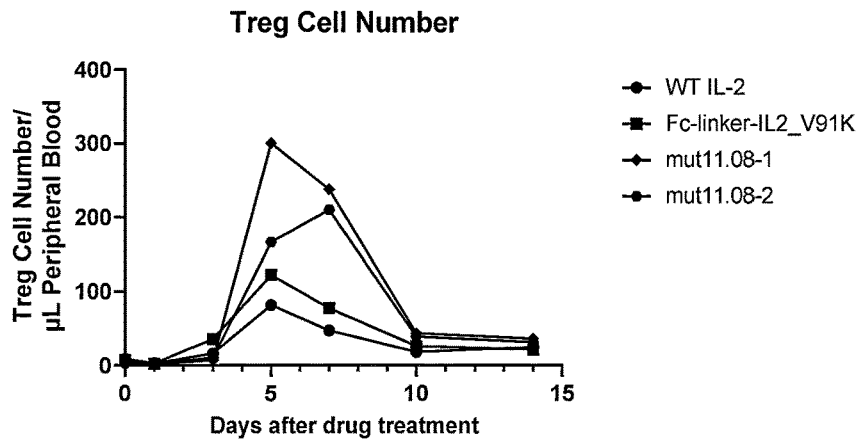
FIG. 20A shows the number of Tregs in cynomolgus monkeys after subcutaneous administration.
Figure 20B:
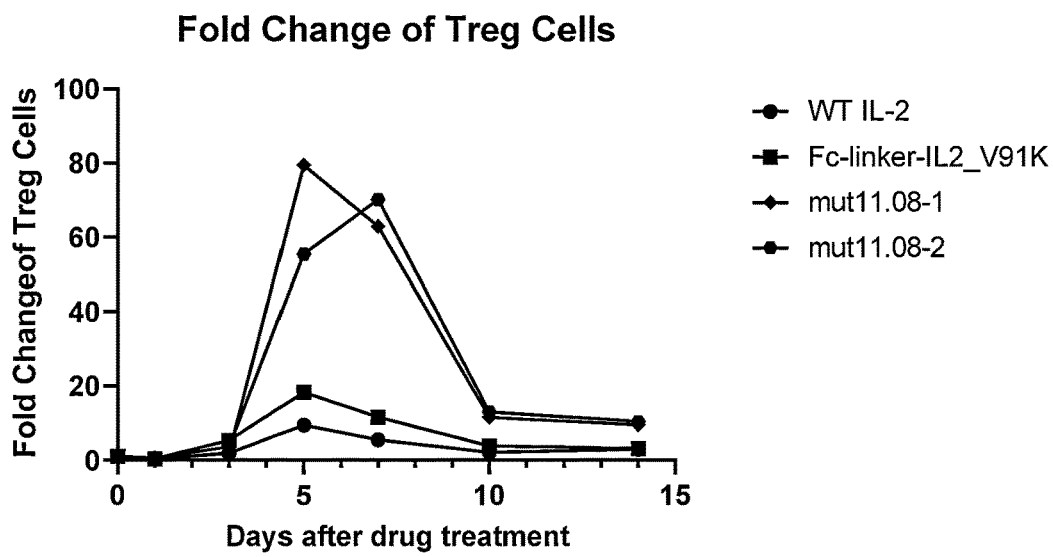
FIG. 20B shows the fold change of Treg number in cynomolgus monkeys after subcutaneous administration.
Figure 20C:
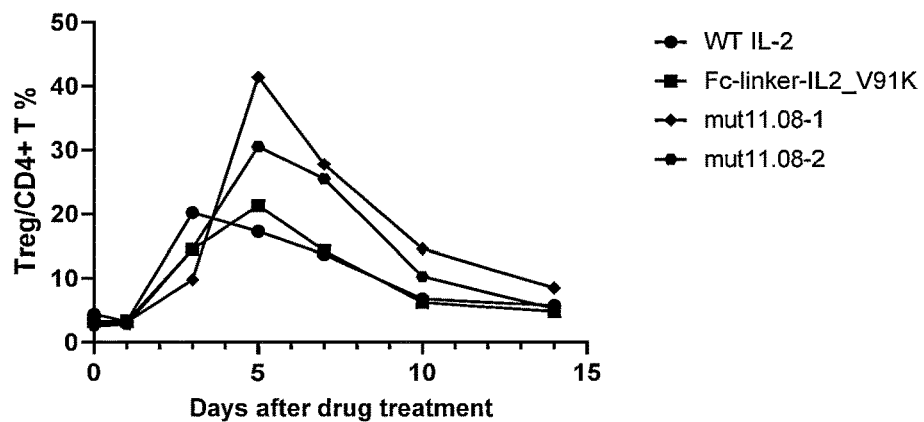
FIG. 20C shows the percentage of Tregs in CD4⁺ T cells in cynomolgus monkeys after subcutaneous administration.
Figure 20D:
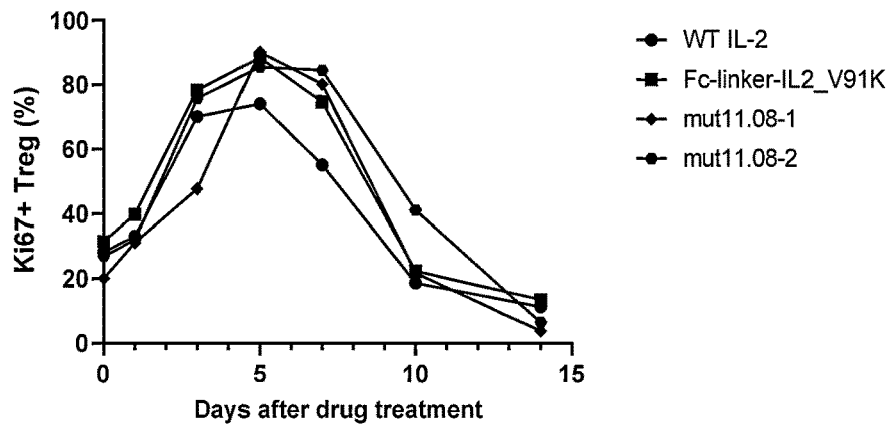
FIG. 20D shows the percentage of Ki67⁺ Tregs in cynomolgus monkeys after subcutaneous administration.
Figure 20E:
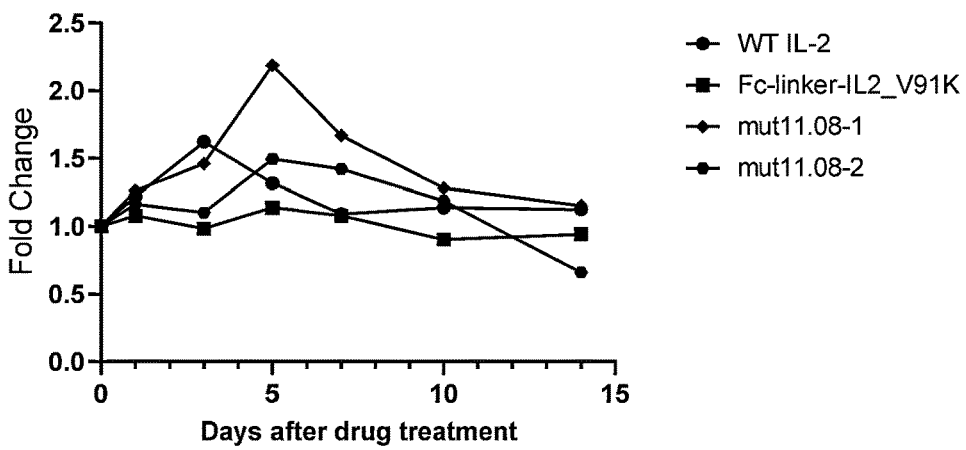
FIG. 20E shows the fold change of FoxP3 average fluorescence intensity in cynomolgus monkeys after subcutaneous administration.
Figure 20F:
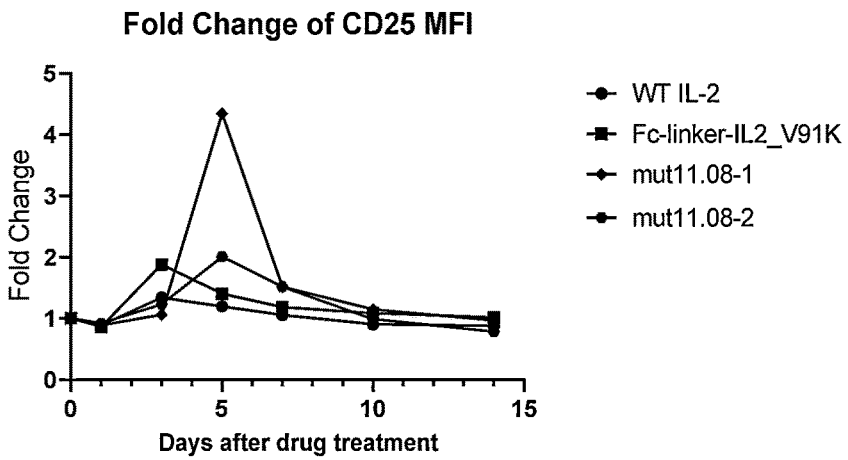
FIG. 20F shows the fold change of CD25 average fluorescence intensity in cynomolgus monkeys after subcutaneous administration.
Figure 21A:
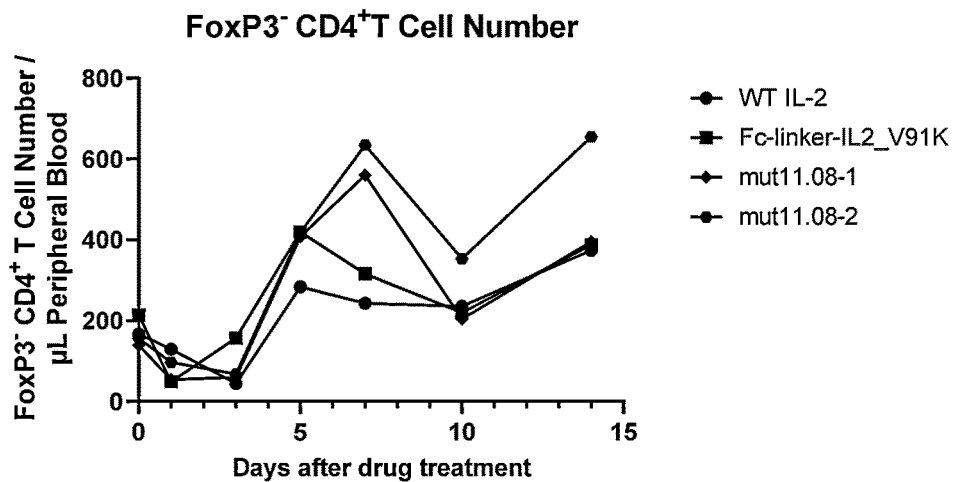
FIG. 21A shows the number of FoxP3⁻CD4⁺ cells in cynomolgus monkeys after subcutaneous administration.
Figure 21B:
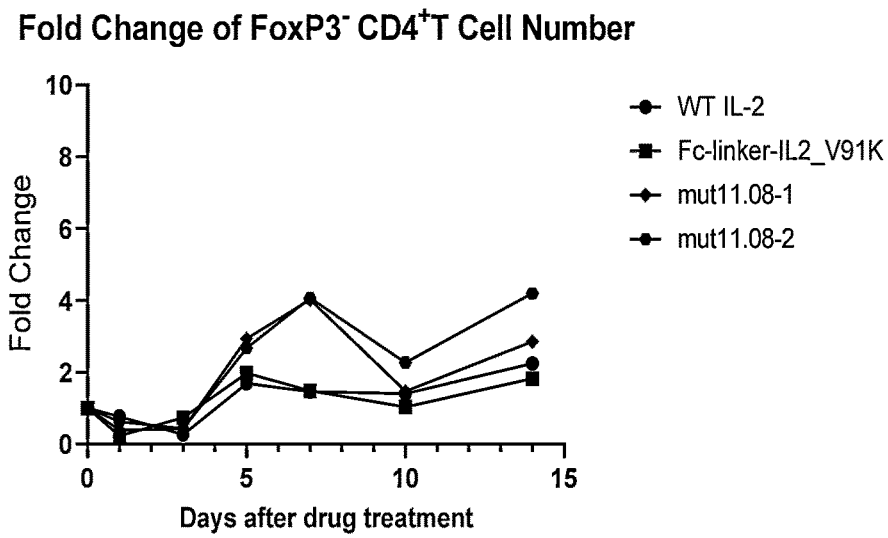
FIG. 21B shows the fold change of FoxP3⁻CD4⁺ cell number in cynomolgus monkeys after subcutaneous administration.
Figure 21C:
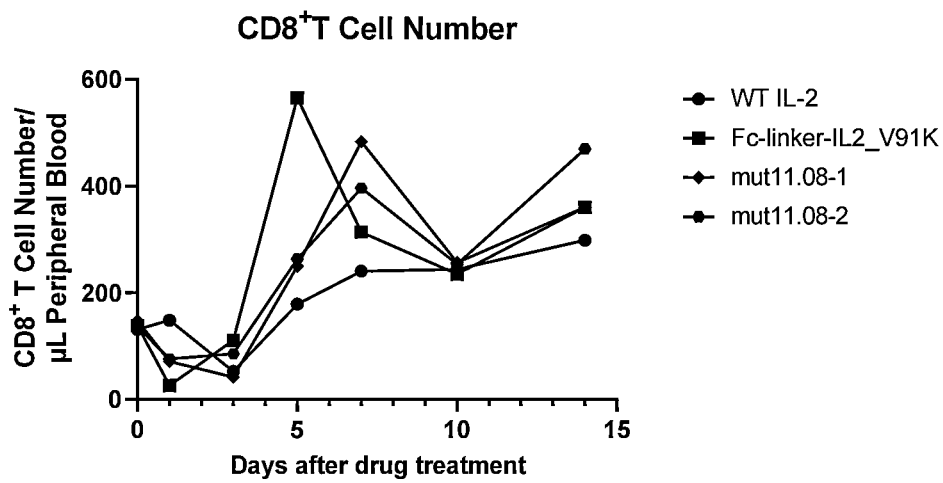
FIG. 21C shows the number of CD8⁺ T cells in cynomolgus monkeys after subcutaneous administration.
Figure 21D:
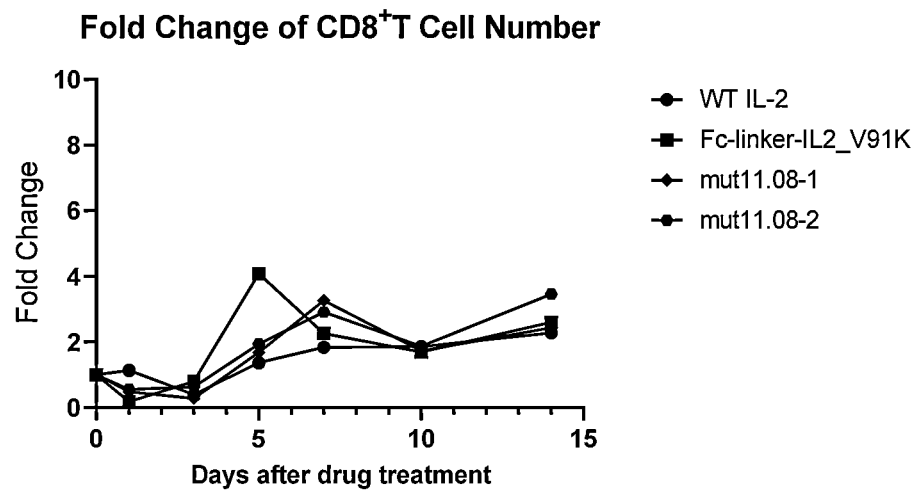
FIG. 21D shows the fold change of CD8⁺ T cell number in cynomolgus monkeys after subcutaneous administration.
Figure 21E:
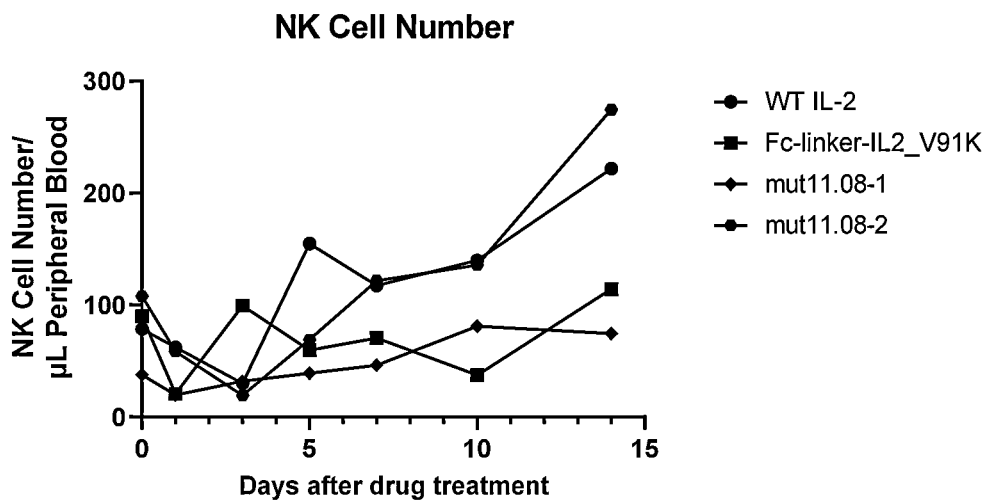
FIG. 21E shows the number of NK cells in cynomolgus monkeys after subcutaneous administration.
Figure 21F:
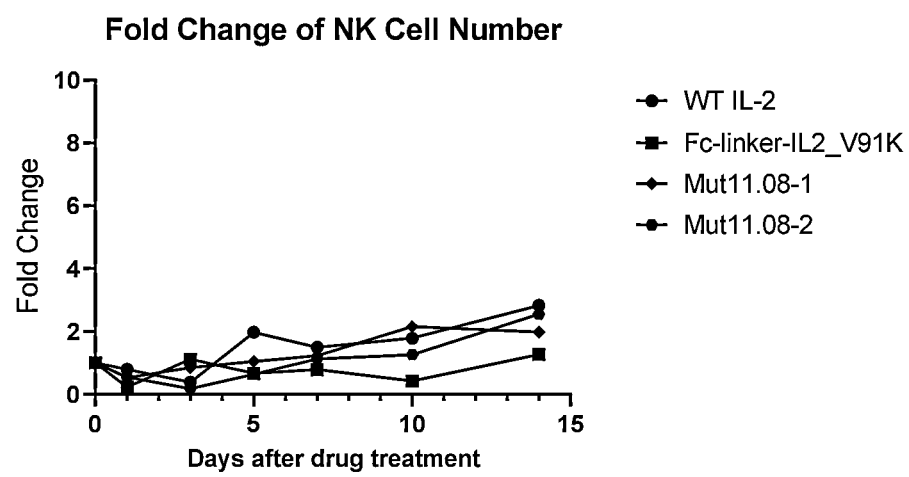
FIG. 21F shows the fold change of NK cell number in cynomolgus monkeys after subcutaneous administration.

4 cynomolgus monkeys were administered IL-2 subcutaneously at a dose of 0.05 mpk, of which 1 monkey was administered with WT IL-2-linker2-hFc (abbreviated as WT IL-2, as shown in SEQ ID NO: 12), 1 monkey was administered with Fc-linker-IL2_V91K, 2 monkeys were administered with mut11.08-linker2-hFc (abbreviated as Mut11.08-1 and Mut11.08-2, respectively), and the plasma drug concentration was detected after administration. The results are shown in FIG. 19 and Table 25. At the dose of 0.05 mpk, WT IL-2 molecule had a longer terminal half-life, and Fc-linker-IL2_V91K and mut11.08-linker2-hFc had a similar terminal half-life. The rank of $C_{max}$ and AUC was mut11.08-linker2-hFc>Fc-linker-IL2_V91K>WT IL-2.

TABLE 25

Pharmacokinetic parameters in cynomolgus monkey after a single subcutaneous administration

| Mean | T½ (h) | Tmax (h) | $C_{max}$ (ng/mL) | AUClast (h*ng/mL) |
|---|---|---|---|---|
| WT IL-2 | 204.97 | 4.00 | 57.70 | 1564.86 |
| Fc-linker-IL2_V91K | 13.20 | 24.00 | 125.07 | 4,669.24 |
| mut11.08-1 | 11.05 | 24.00 | 185.40 | 8,165.21 |
| mut11.08-2 | 11.80 | 24.00 | 355.50 | 15033.23 |

4 cynomolgus monkeys were used to determine the effect of a single subcutaneous administration of mut11.08-linker2-hFc on the expansion of Tregs from cynomolgus monkeys. 1 monkey was administered with WT IL-2-linker2-hFc, 1 monkey was administered with Fc-linker-IL2_V91K, and the other 2 monkeys were administered with mut11.08-linker2-hFc, at a dose of 0.05 mpk (by a single subcutaneous administration). The peripheral blood of cynomolgus monkeys was collected before administration and on Days 1, 3, 5, 7, 10 and 14 after administration. PBMCs were isolated from 2 mL blood sample of cynomolgus monkey collected at different time points and frozen. A vial of frozen PBMCs at each time point was taken and thawed for analysis together. The thawed PBMCs were re-suspended in 1 mL Staining Buffer (DPBS buffer containing 2% FBS), and then 200 μL each was transferred to two 96-well V-Bottom plates, which were labeled as Panel 1 and Panel 2. The two plates were washed once with PBS and then stained with Live/Dead Fixable Near-IR (Thermo, Cat. No. 134976) for 20 min. After staining was terminated by using Staining Buffer, Human TruStain FcX (Biolegend, Cat. No. 422302) was added into the plates and incubated for 20 min. Then the two plates were stained with mixtures of different fluorescent antibodies for 30 min. In panel 1, BV605 Mouse Anti-Human CD3 (BD, Cat. No. 562994), PerCP-Cy5.5 Mouse Anti-Human CD4 (BD, Cat. No. 552838), FITC Mouse Anti-Human CD8 (Biolegend, Cat. No. 301050) and BV421 Mouse Anti-Human CD25 (Biolegend, Cat. No. 302630) were diluted in Brilliant stain buffer (BD, Cat. No. 563794). In panel 2, BV605 Mouse Anti-Human CD3 (BD, Cat. No. 562994), PerCP-Cy5.5 Mouse Anti-Human CD4 (BD, Cat. No. 552838), FITC Mouse Anti-Human CD8 (Biolegend, Cat. No. 301050) and Brilliant Violet 421 anti-human CD16 (Biolegend, Cat. No. 302038) were diluted in Brilliant stain buffer. The cells were washed once after staining was terminated, and fixed and permeabilized by using Foxp3/Transcription Factor Staining Buffer Kit (eBioscience, Cat. No. 00-5523-00). Mixtures of different fluorescent antibodies were added into the two plates to stain cells for 45 min. In panel 1, PE anti-human FOXP3 (Biolegend, Cat. No. 320208) and Ki67 Monoclonal Antibody APC (eBioscience, Cat. No. 17-5698-82) were diluted in Permeabilization Buffer. In panel 2, Ki67 Monoclonal Antibody APC was diluted in Permeabilization Buffer. After staining, the cells were washed once with Permeabilization Buffer and re-suspended with 400 μL Staining Buffer, and 200 μL samples were then analyzed by FACS. The number and the fold change of Tregs, $CD4^+$ $Foxp3^-$ T cells, $CD8^+$ T cells and NK cells in the groups of animals were graphed and analyzed by Graphpad Prism 9 software.

The experimental results are shown in FIG. 20A-20F. After a single subcutaneous administration (0.05 mpk), mut11.08-linker2-hFc significantly increased the number and percentage of Tregs in peripheral blood of cynomolgus monkeys. According to the ratio of Tregs/$CD4^+$T, mut11.08-linker2-hFc favored Treg activation, and thus the percentage of Tregs was about 2 times that of Fc-linker-IL2_V91K. Compared to Fc-linker-IL2_V91K, mut11.08-linker2-hFc showed a greater effect on increasing the proliferation of Tregs (11.08 vs Fc-linker-IL2_V91K=79/55 vs 18), while Fc-linker-IL2_V91K was better than WT (18 vs 9.5) in this respect. According to the analysis of Treg activation markers, there was little difference among $Ki67^+$ Treg % after administration of different molecules. The expression of Treg activation markers (Foxp3 and CD25) increased significantly, which was positively correlated with the proliferation level of Tregs.

As shown in FIG. 21A-21F, after a single subcutaneous administration of Fc-linker-IL2_V91K (0.05 mpk), the maximum fold change of $FoxoP3^-CD4^+$T cells was about 2 times, and that of $CD8^+$T cells was slightly higher, about 4 times. The effect of mut11.08-linker2-hFc on proliferation of $FoxoP3^-CD4^+$T cells was about 2-3 times greater than that of Fc-linker-IL2_V91K, while the effect on the proliferation of $CD8^+$T cell was slightly weaker than or similar to that of Fc-linker-IL2_V91K and was about 1.5-2 times than that of WT. The number of NK cells had not changed significantly after the administration of Fc-linker-IL2_V91K. The effect of mut11.08-linker2-hFc on proliferation level of NK was similar to that of Fc-linker-IL2_V91K.

What is claimed is:

1. A method for treating an autoimmune disease in a subject in need thereof, the method comprising administering to the subject an effective amount of (1) an IL-2 mutant, or (2) a fusion protein comprising the IL-2 mutant, or (3) a pharmaceutical composition comprising the IL-2 mutant or the fusion protein comprising the IL-2 mutant;
   wherein the IL-2 mutant comprises mutations of Y31V, A73L, H79Q and V91R compared to wild-type IL-2; wherein the wild-type IL-2 has an amino acid sequence as shown in SEQ ID NO: 1;
   wherein the fusion protein comprising the IL-2 mutant comprises a first polypeptide and a second polypeptide, wherein the first polypeptide is the IL-2 mutant comprising mutations of Y31V, A73L, H79Q and V91R compared to wild-type IL-2; wherein the wild-type IL-2 has an amino acid sequence as shown in SEQ ID NO: 1, and wherein the second polypeptide is an Fc; and
   wherein the autoimmune disease comprises graft-versus-host disease.

2. The method of claim 1, wherein the IL-2 mutant comprises the amino acid sequence as shown in SEQ ID NO: 32.

3. The method of claim 1, wherein the Fc is a human IgG1 Fc.

4. The method of claim 1, wherein the human IgG1 Fc comprises mutations of C220S and N297G.

5. The method of claim 1, wherein C-terminus of the first polypeptide is linked to N-terminus of the second polypeptide with a linker, wherein the linker is selected from: (G4S)n, (GGNGT)n, or (YGNGT)n, and the n is selected from 1, 2, 3, 4, or 5.

6. The method of claim 1, wherein the fusion protein comprises an amino acid sequence as shown in SEQ ID NO: 50.

7. A method for stimulating STAT5 phosphorylation or cell proliferation of T regulatory cells in a subject, the method comprising administering to the subject an effective amount of (1) an IL-2 mutant, or (2) a fusion protein comprising the IL-2 mutant, or (3) a pharmaceutical composition comprising the IL-2 mutant or the fusion protein comprising the IL-2 mutant;
   wherein the IL-2 mutant comprises mutations of Y31V, A73L, H79Q and V91R compared to wild-type IL-2; wherein the wild-type IL-2 has an amino acid sequence as shown in SEQ ID NO: 1;
   wherein the fusion protein comprising the IL-2 mutant comprises a first polypeptide and a second polypeptide, wherein the first polypeptide is the IL-2 mutant comprising mutations of Y31V, A73L, H79Q and V91R compared to wild-type IL-2; wherein the wild-type IL-2 has an amino acid sequence as shown in SEQ ID NO: 1, and wherein the second polypeptide is an Fc.

8. The method of claim 7, wherein the subject has an autoimmune disease.

9. The method of claim 8, wherein the autoimmune disease comprises rheumatoid arthritis, ankylosing spondylitis, systemic lupus erythematosus, cutaneous lupus erythematosus, lupus nephritis, IgA nephropathy, Sjogren's syndrome, polymyositis, dermatomyositis, scleroderma, psoriasis, plaque psoriasis, alopecia areata, multiple sclerosis, amyotrophic lateral sclerosis, inflammatory bowel disease, ulcerative colitis, Crohn's disease, graft-versus-host disease, organ transplant rejection, autoimmune hepatitis, type I diabetes, autoimmune vasculitis, eczema or asthma.

10. The method of claim 7, wherein the IL-2 mutant comprises the amino acid sequence as shown in SEQ ID NO: 32.

11. The method of claim 7, wherein the Fc is a human IgG1 Fc.

12. The method of claim 11, wherein the human IgG1 Fc comprises mutations of C220S and N297G.

13. The method of claim 7, wherein C-terminus of the first polypeptide is linked to N-terminus of the second polypeptide with a linker, wherein the linker is selected from: (G4S)n, (GGNGT)n, or (YGNGT)n, and the n is selected from 1, 2, 3, 4, or 5.

14. The method of claim 7, wherein the fusion protein comprises an amino acid sequence as shown in SEQ ID NO: 50.

* * * * *